(12) United States Patent
Meutermans et al.

(10) Patent No.: US 7,737,287 B2
(45) Date of Patent: Jun. 15, 2010

(54) ANOMERIC DERIVATIVES OF MONOSACCHARIDES

(75) Inventors: Wim Meutermans, Toowong (AU);
Michael Leo West, Hemmant (AU);
Thanh Le Giang, Mt. Gravatt (AU);
George Adamson, Yateley Hampshire (GB); Karl Schafer, Carindale (AU);
Giovanni Abbenante, Sampsonvale (AU)

(73) Assignee: Alchemia Limited, Eight Mile Plains (AU)

( * ) Notice: Subject to any disclaimer, the term of this patent is extended or adjusted under 35 U.S.C. 154(b) by 1379 days.

(21) Appl. No.: 10/509,092

(22) PCT Filed: Mar. 28, 2003

(86) PCT No.: PCT/AU03/00384
§ 371 (c)(1),
(2), (4) Date: May 4, 2005

(87) PCT Pub. No.: WO03/082846
PCT Pub. Date: Oct. 9, 2003

(65) Prior Publication Data
US 2005/0245746 A1 Nov. 3, 2005

(30) Foreign Application Priority Data
Mar. 28, 2002 (AU) .................... PS1434

(51) Int. Cl.
*C07D 315/00* (2006.01)
(52) U.S. Cl. .................... 549/417; 549/418; 549/419
(58) Field of Classification Search ............ 549/416, 549/417, 419, 420, 424, 418
See application file for complete search history.

(56) References Cited

U.S. PATENT DOCUMENTS 5,719,291 A * 2/1998 Aoki et al. ............... 548/262.2

6,197,963 B1 * 3/2001 Hirschmann et al. ..... 546/282.1

FOREIGN PATENT DOCUMENTS

| WO | 98/08799 A1 | 3/1998 |
| WO | 02/32915 A1 | 4/2002 |
| WO | 02/32963 A1 | 4/2002 |

OTHER PUBLICATIONS

McGraw—Hill Dictionary of Chemical Terms(1990), p. 282.*
Concise Encyclopedia Chemistry (1993), p. 490.*
Hawley's Condensed Chemical Dictionary (1993), p. 594.*
Shaban et al, "The Synthesis of Antigenic Glycopeptides, 2-Acetamido-N-((β-L-aspartyl)-2-deoxy-4-O-β-(D-galactopyranosyl)-β-D-glucopyranosylamine. (N-Acetyl-lactosaminyl-L-asparagine)", Bull. Chem. Soc. Jpn 54(11):3570-3576 (1981).
Nicotra et al, "Stereospecific synthesis of ethyl (2-acetamido-2-deoxy-∀-D-glucopyranosyl)-acetate", Carbohydrate Research 124:C5-C7 (1983).
Yoshimura et al, "Studies On 2-Amino-2-Deoxy-D-Glucose Derivatives. Part XV. Synthesis of 1-N-Acyl-2-Acylamido-2-Deoxy-∃-D-Glucopyranosylamines", Carbohydrate Research 5:82-92 (1967).
Gruner et al; "Carbohydrate Based Mimetics in Drug Design: Sugar Amino Acids and Carbohydrate Scaffolds"; Chem. Reviews. Feb. 2002, 102, pp. 491-514.
Smith et al; "Synthesis of Oligomers of Tetrahydrofuran Amino Acids: Furanose Carbopeptides"; Chem. Commun., 1998, pp. 2039-2040.

* cited by examiner

*Primary Examiner*—Janet L. Andres
*Assistant Examiner*—Raymond Covington
(74) *Attorney, Agent, or Firm*—Nixon & Vanderhye PC

(57) ABSTRACT

This invention relates to combinatorial libraries of potentially biologically active mainly monosaccharide compounds and to methods of preparing same. These compounds are variously functionalized, with a view to varying lipid solubility, size, function and other properties, with the particular aim of discovering a drug or drug-like compound, or compounds with useful properties. The invention provides intermediates, processes and synthetic strategies for the solution or solid phase synthesis of monosaccharides, variously functionalized about the sugar ring, including the addition of aromaticity and charge, and the placement of amino acid and peptide side chain units of isosteres thereof.

24 Claims, No Drawings

ANOMERIC DERIVATIVES OF MONOSACCHARIDES

FIELD OF THE INVENTION

This application is the US national phase of international application PCT/AU03/00384 filed on 28 Mar. 2003, which designated the US and claims priority to AU Application No. PS 1434 filed 28 Mar. 2002. The entire contents of these applications are incorporated herein by reference.

This invention relates to methods for the preparation of combinatorial libraries of potentially biologically active mainly monosaccharide compounds. These compounds are variously functionalized, with a view to varying lipid solubility, size, function and other properties, with the particular aim of discovering novel drug or drug-like compounds, or compounds with useful properties. The invention provides intermediates, processes and synthetic strategies for the solution or solid phase synthesis of monosaccharides, variously functionalised about the sugar ring, including the addition of aromaticity and charge, and the placement of amino acid and peptide side chain units or isosteres thereof.

BACKGROUND OF THE INVENTION

From a drug discovery perspective, carbohydrate pyranose and furanose rings and their derivatives are well suited as templates. Each sugar represents a three-dimensional scaffold to which a variety of substituents can be attached, usually via a scaffold hydroxyl group, although occasionally a scaffold carboxyl or amino group may be present for substitution. By varying the substituents, their relative position on the sugar scaffold, and the type of sugar to which the substituents are coupled, numerous highly diverse structures are obtainable. An important feature to note with carbohydrates, is that molecular diversity is achieved not only in the type of substituents, but also in the three dimensional presentation. The different stereoisomers of carbohydrates that occur naturally (examples include glucose, galactose, mannose etc, FIG. 1), offer the inherent structural advantage of providing alternative presentation of substituents.

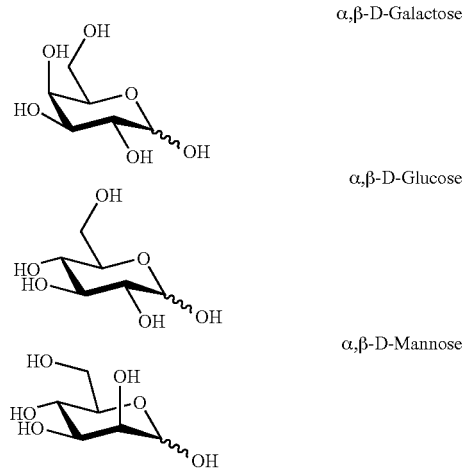

FIG. 1

The first example of a combinatorial approach employing carbohydrate chemistry, was a symposium report on the design and synthesis of a peptidomimetic using a glucose scaffold in the early 1990's[1]. The results, revealed that the glucose based structures designed as mimetics of a potent somatostatin (SRIF) agonist acted as agonists at low concentration, and at high concentration became the first known antagonists of SRIF. Although hardly the production of a library, the results were unique.

Continuing in part the work commenced in the early 1990's, Nicolaou and co-workers began developing carbohydrate based peptido-mimetics targeting integrins. Many integrins recognize an Arg-Gly-Asp (RGD) sequence in ligands such as fibronectin, vitronectin and fibrinogen, each binding with different affinities to the individual integrin receptors. Through a process of rational design a number of carbohydrate based RGD mimetics were synthesized. The chemical synthesis of nine different compounds by this group with very few common intermediates required a considerable amount of chemical effort. It was evident from such results, that in order to generate a number of different structures in a facile manner new chemistries needed to be developed to streamline and enable what at this stage was unfortunately a protracted and arduous methodology.

Since 1998 researchers in the group of Kunz[2] have been developing a number of carbohydrate building blocks with a similar purpose in mind. In general the building blocks that they have developed are coupled to a solid support to effect the desired chemical transformations. The chemistry developed can be employed to achieve, like the work of Hirschmann and co-workers[3], the introduction of peptidomimetic side chains to carbohydrate scaffolds in an effort to produce glyco-based mimetics of cyclic peptides. Admittedly, with the chemistry they have developed, there are inherent limitations in the types of functional groups that they are able to introduce and the range of stereoisomeric building blocks that they are able to employ.

It is now becoming reasonably established in the art that relates to the solid phase production of combinatorial carbohydrate based libraries, that one of five protecting groups on a carbohydrate scaffold is a protecting group modified as a linker, so as to allow coupling of the block to a solid support. The strategy that then follows is simple, remove a protecting group and effect coupling at the freed functionality with a peptidomimetic or other reagent. Remove another protecting group and couple with the next reagent, and so on.

Following this generally accepted principle, a system has been developed that allows the chemical synthesis of highly structurally and functionally diverse derivatised carbohydrate and tetrahydropyran structures, of both natural and unnatural origin. The diversity accessible is particularly augmented by the juxtaposition of both structural and functional aspects of the molecules. In order to access a wide range of diverse structures, stereo-center inversion chemistry is required, so as to achieve non-naturally occurring and hard to get sugars in a facile manner. Other chemistries are also required that provide unnatural deoxy or deoxy amino derivative which impart greater structural stability to the drug-like target molecules. With a suite of reagents to effect a suitable range of chemistries on a solid support, allowing such things as; wide functional diversity, highly conserved intermediates, a limited number of common building block to be required, and with suitable chemistry to allow access to unusual carbohydrate stereo-representations and including access to deoxy and deoxy amino analogues, a methodology is then established that can create focused libraries for a known target, or alternatively diversity libraries for unknown targets for random screening.

Many of the traditional methods of carbohydrate synthesis have proved to be unsuitable to a combinatorial approach, particularly because modem high-throughput synthetic systems require that procedures to be readily automatable. The compounds and processes described herein are particularly suited to the solid and solution phase combinatorial synthesis of carbohydrate-based libraries, and are amenable to automation. The methods of the invention yield common intermediates that are suitably functionalized to provide diversity in the structure of the compounds so generated. In this way the technology described can produce many and varied compounds around the basic structure shown in FIG. 1. Using this method, it is possible to introduce varied functionality in order to modulate both the biological activity and pharmacological properties of the compounds generated.

Thus the compounds and methods disclosed herein provide the ability to produce random or focused combinatorial-type libraries for the discovery of other novel drug or drug-like compounds, or compounds with other useful properties in an industrially practical manner.

It will be clearly understood that, although a number of prior art publications are referred to herein, this reference does not constitute an admission that any of these documents forms part of the common general knowledge in the art, in Australia or in any other country.

SUMMARY OF THE INVENTION

In a first aspect, the invention provides a compound of formula I

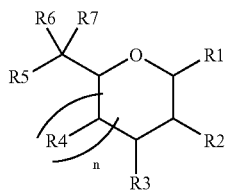

formula I

Wherein, n is 0 or 1; the ring may be of any configuration and the anomeric center may be of either the α or β configuration;

R6 and R7 are hydrogen, or together form a carbonyl oxygen;

R1 is selected from the group consisting of hydrogen; —N(Z)Y and —C(Z)Y wherein;

When R1 is —N(Z)Y, then:

Y is selected from hydrogen, or the following, where G denotes the point of connection to the nitrogen atom in N(Y)Z;

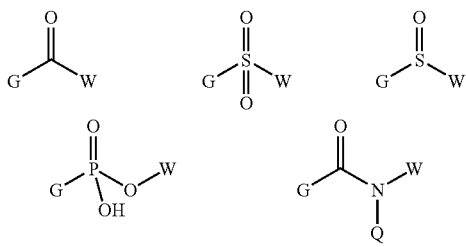

Z is selected from hydrogen or X1;

Q is selected from hydrogen or W;

The groups W are independently selected from alkyl, alkenyl, alkynyl, heteroalkyl, aryl, heteroaryl, arylalkyl or heteroarylalkyl of 1 to 20 atoms which is optionally substituted, branched and/or linear. Typical substituents include but are not limited to OH, NO, $NO_2$, $NH_2$, $N_3$, halogen, $CF_3$, $CHF_2$, $CH_2F$, nitrile, alkoxy, aryloxy, amidine, guanidiniums, carboxylic acid, carboxylic acid ester, carboxylic acid amide, aryl, cycloalkyl, heteroalkyl, heteroaryl, aminoalkyl, aminodialkyl, aminotrialkyl, aminoacyl, carbonyl, substituted or unsubstituted imine, sulfate, sulfonamide, phosphate, phosphoramide, hydrazide, hydroxamate, hydroxamic acid;

The groups X1 are independently selected from alkyl, alkenyl, alkynyl, heteroalkyl, acyl, arylacyl, heteroarylacyl, aryl, heteroaryl, arylalkyl or heteroarylalkyl of 1 to 20 atoms which is optionally substituted, branched and/or linear. Typical substituents include but are not limited to OH, NO, $NO_2$, $NH_2$, $N_3$, halogen, $CF_3$, $CHF_2$, $CH_2F$, nitrile, alkoxy, aryloxy, amidine, guanidiniums, carboxylic acid, carboxylic acid ester, carboxylic acid amide, aryl, cycloalkyl, heteroalkyl, heteroaryl, aminoalkyl, aminodialkyl, aminotrialkyl, aminoacyl, carbonyl, substituted or unsubstituted imine, sulfate, sulfonamide, phosphate, phosphoramide, hydrazide, hydroxamate, hydroxamic acid;

When R1 is —C(Z)Y, then:

Y is selected from hydrogen, double bond oxygen (═O) to form a carbonyl, or triple bond nitrogen to form a nitrile.

Z may be optionally absent, or is selected from hydrogen or U,

Wherein U is independently selected from alkyl, alkenyl, alkynyl, heteroalkyl, aminoalkyl, aminoaryl, aryloxy, alkoxy, heteroaryloxy, aminoaryl, aminoheteroaryl, thioalkyl, thioaryl or thioheteroaryl, acyl, arylacyl, heteroarylacyl, aryl, heteroaryl, arylalkyl or heteroarylalkyl of 1 to 20 atoms which is optionally substituted, branched and/or linear. Typical substituents include but are not limited to OH, NO, $NO_2$, $NH_2$, $N_3$, halogen, $CF_3$, $CHF_2$, $CH_2F$, nitrile, alkoxy, aryloxy, amidine, guanidiniums, carboxylic acid, carboxylic acid ester, carboxylic acid. amide, aryl, cycloalkyl, heteroalkyl, heteroaryl, aminoalkyl, aminodialkyl, aminotrialkyl, aminoacyl, carbonyl, substituted or unsubstituted imine, sulfate, sulfonamide, phosphate, phosphoramide, hydrazide, hydroxamate, hydroxamic acid;, heteroaryloxy, aminoalkyl, aminoaryl, aminoheteroaryl, thioalkyl, thioaryl or thioheteroaryl, which may optionally be further substituted.

Suitably, When R1 is H, at least two of the groups R2, R3, R4 and R5 are selected from the group consisting of —OX2 or —N(T)Y, and the others are independently selected from hydrogen, —OH, —OX2, —N(T)Y, wherein Y is as defined above, T is selected from hydrogen or X2; and X2 is independently selected from alkyl, alkenyl, alkynyl, heteroalkyl, aryl, heteroaryl, arylalkyl or heteroarylalkyl of 1 to 20 atoms, When R1 is N(Z)Y or C(Z)Y, at least one of the groups R2, R3, R4 and R5 are selected from the group consisting of —OX2 or —N(T)Y, and the others are independently selected from hydrogen, —OH, —OX2, —N(T)Y, wherein Y is as defined above, T is selected from hydrogen or X2; and X2 is independently selected from alkyl, alkenyl, alkynyl, heteroalkyl, aryl, heteroaryl, arylalkyl or heteroarylalkyl of 1 to 20 atoms, It is understood that the rules of molecular stoichiometry will be upheld by the default addition of hydrogens atoms as required.

The groups Z and Y may be combined to form a monocyclic or bicyclic ring structure of 4 to 10 atoms. This ring structure may be further substituted with X groups;

The groups R2, R3, R4 and R5 are independently selected from hydrogen, OH, NHDde, NHDTPM and other vinylogous amines, N(Z)Y, wherein N(Z)Y is as defined above, OX and X is independently selected from alkyl, alkenyl, alkynyl, heteroalkyl, aminoalkyl, aminoaryl, aryloxy, alkoxy, heteroaryloxy, aminoaryl, aminoheteroaryl, thioalkyl, thioaryl or thioheteroaryl, acyl, arylacyl, heteroarylacyl, aryl, heteroaryl, arylalkyl or heteroarylalkyl of 1 to 20 atoms which is optionally substituted, branched and/or linear. Typical substituents include but are not limited to OH, NO, $NO_2$, $NH_2$, $N_3$, halogen, $CF_3$, $CHF_2$, $CH_2F$, nitrile, alkoxy, aryloxy, amidine, guanidiniums, carboxylic acid, carboxylic acid ester, carboxylic acid amide, aryl, cycloalkyl, heteroalkyl, heteroaryl, aminoalkyl, aminodialkyl, aminotrialkyl, aminoacyl, carbonyl, substituted or unsubstituted imine, sulfate, sulfonamide, phosphate, phosphoramide, hydrazide, hydroxamate, hydroxamic acid;

With the proviso that when R2 is N(Z)Y, R6 and R7 are hydrogen, and R4 and R5 are OH or together form a benzylidene or substituted benzylidene, then R1 cannot be N(Z)Y.

A preferred embodiment of the first aspect provides for compounds of formula I in which R1 is H and R4 is N(Z)Y;

In a particularly preferred embodiment R1 is H and R4 is N(Z)Y wherein Z is hydrogen;

A further embodiment of the first aspect provides for compounds of formula I in which R1 and R4 are independently N(Z)Y;

Another embodiment provides for compounds of formula I in which R1 is H and both R2 and R4 are N(Z)Y;

In a preferred embodiment provides for compounds of formula I in which the ring is of the gluco, galacto or alto configuration;

A further embodiment provides for compounds of formula I in which R1 is N(Z)Y and R2 is N(Z)Y;

A further embodiment provides for compounds of formula I in which R1 is P(Z)Y and R2 is N(Z)Y, wherein P is carbon and Y is hydrogen.

A further embodiment provides for compounds of formula I in which R1 is P(Z)Y and R4 is N(Z)Y, wherein P is carbon and Y is hydrogen.

A further embodiment provides for compounds of formula I in which R1 is N(Z)Y and R5 is N(Z)Y and the ring is of the furan form.

In a second aspect, the invention provides for a method of synthesis of compounds of formula 1 in which R1 is hydrogen, comprising the step of reducing a synthetic intermediate of formula II, in which the substituent V is either bromine or chlorine, R6 and R7 are as defined in the first aspect, R5, R4, R3, and R2 are independently selected from OH, O-acyl, $N_3$, NHDde, NHDTPM, NHZ, NHBOC, phthalimide, O-protecting group or when R6 and R7 together for a carbonyl oxygen, R5 may additionally be optionally substituted O-alkyl, O-arylalkyl or O-aryl. Where the protecting groups may be chosen from any suitable oxygen protecting groups known in the art, including acetals and ketals which protect two adjacent oxygens.

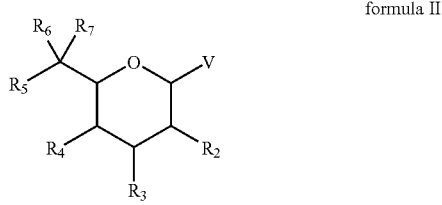

formula II

In a third aspect, the invention provides for a method of synthesis of compounds of formula I in which R1 is N(Z)Y comprising the step of reacting a compound of formula II with and azide nucleophile, in which the substituents for formula II are as described in the second aspect.

In a fourth aspect, the invention provides for a method of combinatorial synthesis of compounds of the formula I comprising the step of immobilizing a compound of formula III onto a support. Said support may be soluble or insoluble. Non-limiting examples of insoluble supports include derivatised polystyrene, tentagel, wang resin, MBHA resin, aminomethylpolystyrene, rink amide resin etc. Non-limiting examples of soluble supports include DOX-mpeg, polyethylene glycol etc.

formula III

Wherein R1 is as defined in the first aspect, R2, R3, R4, R5, R6 and R7 are as defined in the second aspect, and the linkage between the compound of formula III and the support is through any of positions R2, R3,R4 or R5.

In a fifth aspect, the invention provides for a method of synthesis of compounds of formula I in which R1 is N(Z)Y, comprising the step of reacting a compound of formula IV in the presence of a lewis acid with an azide source.

formula IV in which the substituent V is —OAcyl, R6 and R7 are as defined in the first aspect, R4, R3, and R2 are independently selected from OH, O-acyl, $N_3$, NHDde, NHDTPM, NHZ, NHBOC, phthalimide, O-protecting group or when R6 and R7 together for a carbonyl oxygen, R4 may additionally be optionally substituted O-alkyl, O-arylalkyl or O-aryl. Where the protecting groups may be chosen from any suitable oxygen protecting groups known in the art, including acetals and ketals which protect two adjacent oxygens.

In a sixth aspect, the invention provides for a method of synthesis of compounds of formula I in which RI is H, comprising the step of reducing a compound of formula IV in which the substituents for formula II are as described in the fifth aspect.

In a seventh aspect, the invention provides for a method of combinatorial synthesis of compounds of formula I comprising the step of immobilizing a compound of formula V onto an support. Said support may be soluble or insoluble. Non-limiting examples of insoluble supports include derivatised polystyrene, tentagel, wang resin, MBHA resin, aminomethylpolystyrene, rink amide resin etc., Non-limiting examples of soluble supports include DOX-mpeg, polyethylene glycol etc.

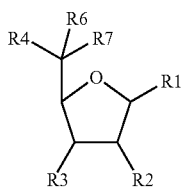

formula V

Wherein R1 is as defined in the first aspect, R2, R3, R4, R6 and R7 are as defined in the fifth aspect, and the linkage between the compound of formula V and the support is through any of positions R2, R3, or R4.

In a eighth aspect, the invention provides for a method of solution phase combinatorial synthesis of compounds of formula I comprising the step of alkylating a free hydroxyl on a compound of formula III, wherein R1 is as defined in the first aspect, R2, R3, R4, R5, R6 and R7 are as defined in the second aspect and any one of the protecting substituents may be removed prior to alkylation.

Compounds of the invention are useful in screening for biological activity.

For the purposes of this specification it will be clearly understood that the word "comprising" means "including but not limited to", and that the word "comprises" has a corresponding meaning.

General Solution and Solid Phase Methods for Examples 1-21

General Method 1: Formation of a Glycosyl Bromide

To a solution of the anomeric-acetate compound (100 mmol) in dichloromethane (250 mL) at 0° C., was added a solution of 33% HBr in acetic acid (100 mL). The solution was then stirred for 2 h at room temperature. At this time chloroform was added to the suspension and the resulting solution poured onto ice/water. The chloroform layer was then collected and washed with cold water, saturated sodium hydrogen carbonate, brine, dried (MgSO$_4$), and the solvent removed to leave a foam. This foam was trituated with ether (50 mL) for 30 min and the resulting solid filtered to give the glycosyl bromide as a white solid. Yield typically greater than 95%.

General Method 2: Reduction at the Anomeric Centre to Form a Glycitol

To a suspension of glycosyl bromide (100 mmol) in dry toluene 200 mL was added tributyltin hydride (110 mmol) and the whole refluxed under nitrogen for 3 h. The suspension was concentrated to dryness and the residue re-dissolved in a 2:1 dichloromethane/chloroform (250 mL) mixture. To the residue was then added potassium fluoride (20 g) in water (100 mL), and the heterogeneous solution stirred vigorously for 45 min. The resulting suspension was filtered through a pad of celite and washed several times with dichloromethane. The combined filtrates were then washed with water, brine, dried (MgSO$_4$), and solvent removed in vacuo to leave a solid in typically quantitative yield.

General Method 3: Solution Phase Zemplen

To a suspension of the acetylated compound (100 mmol) in dry methanol (125 mL) at 0° C. was added a solution of sodium methoxide (0.33 mmol) in dry methanol (125 mL) and the mixture was stirred under nitrogen for 2 h. Amberlite IR 120 H$^+$ was added until pH 5 was reached, the solution was filtered and the resin washed several times with a 2:1 methanol/dichloromethane mixture. The combined filtrates were then concentrated to dryness to leave a solid. Typically quantitave yield.

General Method 4: Solution Phase Benzylidene Protection

To a solution of the triol (~100 mmol) in dry N,N-dimethylformamide (325 mL)/acetonitrile (200 ml) was added 4-methoxybenzaldehyde dimethyl acetal (180 mmol) and p-toluene sulfonic acid (2.5 mmol). This solution was then heated at 60° C. on a rotary evaporator at 300 mmHg for 30 min and then over the course of 4 h the pressure was reduced to 80 mmHg and approximately 200 mL of solvent collected. After this time a second batch of reagent (70 mmol) and acetonitrile (125 mL) was added and the evaporation process repeated over 2 h. All solvent was then removed under reduced pressure and the residue re-dissolved in an 8:1 chloroform/triethylamine mixture, washed with dilute sodium hydrogen carbonate, dried (MgSO$_4$) and the solvent removed under reduced pressure to leave a oil. The oil was typically loaded onto a pad of silica and eluted with ~10% ethyl acetate in light petroleum (40-60° C.), to provide a white solid.

General Method 5: Solution Phase Benzoylation

The sugar (100 mmol) was partially suspended in pyridine (400 mL) and p-chlorobenzoyl chloride (46 mL, 120 mmol) added dropwise at 0° C. and the resulting reaction mixture stirred at room temperature for 2 h. After this time cold water (30 mL) was added and the solution stirred for a further 1 h at room temperature. All solvents were then removed under reduced pressure and any traces of pyridine azeotropically removed with toluene. The residue solid was then redissolved in chloroform and washed with water, 10% citric acid, saturated sodium hydrogen carbonate, brine, dried (MgSO$_4$) and concentrated under reduced pressure to leave a foam. This foam was trituated with ether and the resulting solid filtered to give the benzoylated compound as a solid, typical yield ~85%.

General Method 6: Solution Phase Nucleophilic Inversion of a Carbon Centre

To a solution of the sugar (100.0 mmol) in dry chloroform (300 mL) cooled to −20° C., was added pyridine (180.0 mmol) and trifluoromethane sulfonic anhydride (115 mmol) and the whole stirred for 1 h at this temperature. The reaction was then diluted with chloroform, and the resulting solution washed with cold water, cold 10% hydrochloric acid, cold water, dried (MgSO$_4$), and the solvent removed in vacuo. The resulting residue was then redissolved in N,N-dimethylformamide (600 mL), and sodium azide (500 mmol) was added at 0° C. in portions. The suspension stirred overnight at room temperature. The reaction was diluted with chloroform and the resulting solution then washed with water, 10% citric acid, saturated sodium hydrogen carbonate, brine, dried (MgSO$_4$), and the solvent removed in vacuo, followed by azeotroping with toluene to leave the product, typically 95% yield.

General Method 7: Solution Phase Alkylation

To a suspension of sodium hydride (100 mmol) in dry N,N,-dimethylformamide (360 mL) at 0° C. under nitrogen was added a solution of the sugar (63.2 mmol) in dry N.N-dimethylformamide (30 mL). The mixture was stirred at 0° C. for 15 min and then warmed to room temperature and stirred for a further 30 min. The suspension was again cooled to 0° C., the alkylating agent (85 mmol) added dropwise over a period of 5 min, after which the suspension was warmed to room temperature and stirred for 16 h. The suspension was then cooled to 0° C. and the reaction quenched with ammonium chloride solution, chloroform added, and the organic layer washed with saturated sodium hydrogen carbonate, water, dried (MgSO$_4$) and all solvent removed to leave an oil. Crude products were purified by column chromatography (typically: silica, 50% ethyl acetate in light petroleum (40-60° C.)) to give the desired product as a solid, in yields of 55-95%.

General Method 8: Solution Phase DTPM Removal

To a solution of the DTPM derivatised sugar (100 mmol) in a 3:1 mixture of dry methanol/N,N,-dimethylformamide (500 mL), was added hydrazine monohydrate (350 mmol) and the mixture stirred for 3 h. After this time the mixture was filtered and the filtrate was then concentrated under reduced pressure. The residue was redissolved in dichloromethane, washed with saturated sodium chloride, dried (MgSO$_4$) and all solvent removed under reduced pressure to leave a solid, typically in quantitative yield.

General Method 9: Solution Phase HBTU Coupling

To a solution of the acylating agent (10 mmol) and HBTU (12 mmol) in dry N,N,-dimethylformamide (60 mL) was added diisoproplyethylamine (25 mmol) and the mixture stirred for 10 min. A solution of the sugar building block (9.4 mmol) in dry N,N,-dimethylformamide (8 mL), was then added and the mixture further stirred for 16 h. Chloroform was then added and the reaction mixture was washed with water, 10% citric acid, saturated sodium hydrogen carbonate, brine, dried (MgSO$_4$) and the solvent removed under reduced pressure to leave an oil. Purification of the products was by column chromatography (typically, silica; 50% ethyl acetate in light petroleum (40-60° C.)), or alternatively by trituration with diethyl ether to give clean products in typical yields of 55-85%.

General Method 10: Solution Phase Reaction with an Isocyanate

To a solution of the sugar derivative (10 mmol) in dry dichloromethane (100 mL) was added dropwise ethyl isocyanatoacetate (10.7 mmol). The resulting solution stirred for 3 h. In the case of a precipitate occurring, the solid was filtered after 3 h and washed with dichloromethane to give a white solid. Alternatively if no precipitate formed, chloroform was added and the reaction mixture washed with water, dried (MgSO$_4$) and the solvent removed in vacuo to typically leave an oil. Purification of oils was achieved by column chromatography. Products were typically formed in yields of 65-90%.

General Method 11: Solution Phase Reaction with an Anhydride

To a solution of the sugar derivative (10 mmol) in dry dichloromethane (90 mL) was added dropwise acetic anhydride (11 mmol). The resulting solution stirred for 16 h. In the case of a precipitate occurring, the solid was filtered after and washed with dichloromethane to yield a white solid. Alternatively if no precipitate occurred, chloroform was added and reaction mixture washed with water, 10% citric acid, saturated sodium hydrogen carbonate, brine, dried (MgSO$_4$) and the solvent removed under reduced pressure to leave an oil. Oils were purified by column chromatography. Products were typically formed in yields of 50-99%.

General Method 12: Solution Phase Reaction with an Acid Chloride

To a solution of the sugar derivative (10 mmol) in dichloromethane (100 mL) was added diisopropylethylamine (12 mmol) and an acid chloride (11.6 mmol), and the solution then stirred for 16 h. Chloroform was then added and the reaction mixture washed with water, 10% citric acid, saturated sodium hydrogen carbonate, brine, dried (MgSO$_4$) and the solvent removed under reduced pressure to give an oil. Purification was by either column chromatography (typically: silica; 50% ethyl acetate in light petroleum (40-60° C.)), or by trituation with diethyl ether. Products were typically formed in yields of 70-80%.

General Method 13: Solution Phase Reduction of an Azide

To a stirred solution of the sugar derivative (10 mmol) in methanol (90 mL) was a solution of ammonium chloride (50 mmol) in water (18 mL). Added to the reaction mixture was zinc dust (300 mmol) and the resulting suspension stirred for 3 h. The reaction mixture was then filtered through a pad of celite and washed with ethyl acetate. The organic layer was then collected, washed with saturated sodium hydrogen carbonate, dried (MgSO$_4$) and all solvent removed under reduced pressure to leave a white solid. Products were typically formed in yields of 60-75%.

General Method 14: Solution Phase Removal of p-Methoxybenzyl Group

Sugar derivative (~2 mmol) was dissolved in a solution of 70% chloroform, 20% trifluoroacetic acid, 5% anisole, 5% water, and the resulting reaction mixture stirred for 6 h. All solvent was then removed under reduced pressure to leave a dark oil. Products were purified by HPLC-MS General Method 15: Solution Phase Base Catalysed Hydrolysis Sugar derivative (~2 mmol) was dissolved in methanol (~1.5 mL). To this solution was 1M sodium hydroxide (0.42 mL) and the resulting reaction mixture agitated for 16 h. Amberlite resin (400 mg) was added, the suspension was then stirred for 30 sec, filtered, and resin washed with methanol. The resulting solutions were collected and freeze dried, and the residues then purified by HPLC-MS.

General Method 16: Simultaneous Removal of Benzoate and DTPM

Sugar derivative (1 mmol) was stirred at room temperature in a 1 molar NaOH/methanol solution (6 mL, 1.5 mmol) in DMF (1.5 ml) until complete consumption for (12 hrs). Hydrazine monohydrate (0.3 ml) was added and the stirring continue for 2 hr. The volatile solvents were removed in vacuo and the residue was taken up in EtOAc and washed with saturated bicarbonate solution, dried over MgSO$_4$, and evaporated to dryness. Products were typically formed in yields of 85-90%.

General Method 17: Solution Phase Diazotransfer

To a solution of the sugar derivative (1 mmol) and CuSO$_4$.5H$_2$O (0.02 mmol) in methanol/water (5:1, 10 mL), was added drop-wise the TfN$_3$ solution (~4.5 mmol). The reaction mixture was stirred at room temperature for 20 hr and more TfN$_3$ (~1.4 mmol) was added. After additional 16 hr, concentrated NH$_4$OH solution was added to quench excess TfN$_3$ and the stirring continued for 72 hr. The phases were separated and the aqueous phase was extracted with dichloromethane. The combined organic layers were washed with saturated bicarbonate solution, dried over MgSO$_4$ and evaporated to dryness. The residue was evaporated to afford the desired product in quantitative yield.

General Method 18: Solution Phase Benzylidene Removal

To a solution of the sugar derivative (1 mmol) in acetonitrile/methanol/water (1:1:0.1), was added TsOH.H$_2$O (~100 micromol). The resulting reaction mixture was stirred at 50° C. for 1.5 hrs. The volatile solvents were then removed in vacuo and the residue purified by flash chromatography. The desired product was typically obtained in 70-80% yield.

General Method 19: Solution Phase Silyl Protection.

To a solution of the sugar derivative (1 mmol) in pyridine (1ml), was added DMAP (1 mmol) and TBDPSCL (1.5 mmol). The resulting reaction mixture was stirred at 120° C. for 45 min, then the solvent removed in vacuo. The residue was taken up in dichloromethane washed with 1 N HCl solution, dried over $MgSO_4$ and evaporated to dryness. The residue was chromatographed to afford the desired product in typically 85-95% yield.

General Method 20: Coupling of Building Block to Resin

The Trichloroacetimidate derivatised resin (IRORI Wang resin ~1 mmol) was weighed into the reaction vessel and washed with THF. The derivatised building block (1.86 mmol) was dissolved in anhydrous DCM (1.2 ml), added to the resin and shaken for 3 mins. $BF_3.Et_2O$ (~100 µl) was added and the reaction vessel shaken continuously for 10 mins. The reaction mixture was filtered under vacuum and the resin washed with THF, DCM, and dried.

General Method 21: Solid Phase Debenzoylation

The resin bound sugar was shaken in a solution of THF/MeOH (5:1) and NaOMe (0.02 Molar) overnight. The reaction was drained and washed with anhydrous THF and repeated as described above. The reaction solvent was drained and the resin washed with THF, a solution of THF: $CH_3COOH$: MeOH 8:1:1, THF, and DCM. The resin was dried overnight.

General Method 22: Solid Phase Alkylation

The resin was reacted with a 0.25 molar solution of tert-butoxide in DMF (5 min) and then the alkylating agent, (0.25 molar in DMF, 20 min) was reacted with the resin. The resin was washed with DMF and again treated with the two solutions, this procedure was repeated a further four times. The final wash of the resin was performed as above; with DMF, THF/MeOH/$CH_3CO_2H$ (8:1:1), THF, DCM and MeOH. The resin was then dried overnight.

General Method 23: Solid Phase Silyl Deprotection

A solution of PSHF (proton sponge hydrogen fluoride) (0.5 Molar in DMF/Acetic Acid, 95:5) was prepared. The resin was added to the solution and the reaction was stirred at 65° C. for 24 hours. The resin was then washed with DMF, MeOH/$CH_3COOH$/THF, 1:1:8, THF and DCM, and then dried under high vacuum General Method 24: Solid Phase Azide Reduction Resin was placed in a round bottom flask. A solution of tert-Butoxide (0.2 molar) in anhydrous DMF was prepared. DTT (0.2 molar) was added to the tert-Butoxide solution and stirring continued until all DTT dissolved. The solution was poured into the Buchner flask containing the Kans. The reactor was degassed by applying vacuum (15 mbar) and filled with nitrogen. This technique was repeated twice and the reactor shaken at room temperature for 6 hr, allowing the evolved $N_2$ gas to escape. The reaction solvent was removed from the flask and the Kans washed with DMF, THF, and MeOH before being dried under high vacuum for 12 hours.

General Method 25: Solid Phase N-Acylation

Method 1

Acids were weighed into round bottom flask and DIC (diisopropylcarbodiimide) (0.25 molar) in DMF was added to make a 0.5 molar solution of the acid. The resultant solution was stirred at room temperature for 1 hour and DMAP (to 0.05 molar) was added. The solution was poured into a reactor containing the Kans and shaken vigorously. The reactor was degassed by applying vacuum (15 mbar) and filled with nitrogen. This technique was repeated twice and the reactor shaken at room temperature over night. The reaction solvent was removed from the flask and the Kans washed with DMF, MeOH, THF, MeOH, DCM and MeOH.

Method 2:

Acids were weighed into round bottom flask and DMF was added to make a 0.5 M solution, followed by addition of DIPEA (to make 0.5 M). The solution was stirred until homogeneous and HBTU (to make 0.5 M) was added. Stirring was continued for additional 30 minutes and the solution was poured into a reactor containing the Kans and shaken vigorously. The reactor was degassed by applying vacuum (15 mbar) and filled with nitrogen. This technique was repeated twice and the reactor shaken at room temperature for overnight. The reaction solvent was removed from the flask and the Kans washed with DMF, MeOH, THF, MeOH, DCM and MeOH.

General Method 26: Solid Phase Nitro Group Reduction

A solution of tin(II) chloride (1 Molar) in a mixture of DMF and water was prepared, filtered, the solution was poured into a reactor containing the Kans and shaken vigorously. The reactor was degassed by applying vacuum (15 mbar) and filled with nitrogen. This technique was repeated twice and the reactor shaken at room temperature for 24 hour. The Kans were washed with DMF, THF, DCM, MeOH and DCM and dried under high vacuum.

General Method 27: Solid Phase Fmoc Removal

A 20% v/v solution of piperidine in DMF was prepared and the solution was poured into a reactor containing the Kans and shaken vigorously. The reactor was degassed by applying a vacuum (15 mbar) and then was filled with nitrogen. This technique was repeated twice and the reactor shaken at room temperature for one hours. After one hour the solvent was removed, the Kans were washed with DMF and the deprotection was repeated as above. The reaction solvent was removed, the Kans washed with DMF, MeOH, THF, MeOH, DCM and MeOH and dried under high vacuum.

General Method 28: Solid Phase Guanylation

A solution of 3,5-dimethylpyrazolyl formamidinium nitrate (0.2 molar) in anhydrous DMF was prepared, and DIPEA (to 1 molar) added. The resin in Kans were pooled, added to the solution, and the reaction was stirred at 65° C. for 24 hours. The reaction solvent was removed from the flask via a vacuum line and the flask shaken to release further solvent from the Kans. The Kans were washed with DMF, THF and DCM and dried under high vacuum.

General Method 29: Cleavage from Resin

Cleaving solutions were prepared from DCM (60%), triethylsilane (20%), TFA (20%). The Kans were opened and the resins poured into reactors in the MiniBlock, 0.7 ml of the above cleaving solution was added to each reactor and the reactors were shaken at room temperature for 3 hours. The solutions were collected into test tubes (12×75 mm). The resins were washed with DCM. The washings were combined with the cleavage in the test tubes and the volatile solvents were removed by beta RVC. The residues were dried in the vacuum oven for 48 hours. Analytical samples were obtained by washing the remaining resins with acetonitrile (0.5 ml), collected in 96-wells plate and evaporated in alpha RVC. The samples were re-dissolved in acetonitrile and analysed.

General Method 30: DTPM Protection of an Amine

To a stirred solution of the amino compound (20 mmol) dissolved in MeOH (150 mL) at room temperature was added a solution of DTPM reagent (20 mmol) in MeOH (50 mL). After 10 min the product started to crystallise and after 40 mins the reaction mixture was filtered. The crystalline residue was washed with ether and dried under vacuum to yield the DTPM protected product in typically 90% yield.

General Method 31: N-Acyl Formation using Diisoprolycarbodiimide

A solution of the starting material (0.62 mmol) in dry DCM was added to a solution of the acid (0.76 mmol) and DIC (0.76 mmol) in DCM (5 mL). The reaction was stirred for 3 h and the reaction mixture then diluted with DCM. The reaction mixture was washed with 10% citric acid, satd. sodium bicarbonate solution, filtered over cotton and the solvents evaporated. Column chromatography of the resulting residue provided the product, typically in 90% to near quantitative yields.

General Method 32: Solid Phase Cleavage of the DTPM Protecting Group.

A 5% solution of hydrazine hydrate in DMF was prepared. The cleavage solution was added to resin in a reactor (approx. 1 mL per 100 mg of resin) and left to react for four hours. The resin was filtered, and washed with DMF, MeOH, THF, MeOH, DCM and MeOH and then dried under high vacuum.

General Method 33: Selective Benzgyidene Ring Opening to the 6-Position.

The benzylidene protected compound (50 mmol) was dissolved in dry N,N-dimethylformamide (400 mL) and added to a flask containing pre-activated 3A molecular sieves (120 g). To this suspension was added sodium cyanoborohydride (300 mmol) and the resulting reaction mixture stirred for 30 min under nitrogen. The suspension was then cooled to 0° C., and a solution of TFA (650 mmol) in dry N,N-dimethylformamide (80 mL) added in portions, and the suspension then heated at 55° C. for 16 h. The suspension was then filtered through a bed of celite and washed several times with chloroform. These combined washings were then washed with water, 10% citric acid, saturated sodium hydrogen carbonate, brine, dried (MgSO$_4$), and the solvent removed in vacuo to leave a yellow foam, which was azeotropically dried with toluene. Typical yields were in the order of 85-95%.

General Method 34: Formation of a Glycosyl Azide.

From the anomeric acetate derivative the glycosyl bromide was prepared as described in General Method 1. To a solution of the bromosugar (50 mmol) in acetonitrile (200 mL) was added TMS-azide (100 mmol) followed by TBAF (100 mmol). The reaction mixture was left to stir for 2 hours at which time the solvent was removed in vacuo, the residue taken up in chloroform, and the resulting solution washed with saturated sodium hydrogen carbonate, brine, dried (MgSO$_4$), and the solvent removed in vacuo to leave a solid, typically in 85-95% yield.

EXAMPLE 1

Synthesis of 1,5-anhydro-4-azido-3-O-(4-chlorobenzoyl)-2,4-dideoxy-2-[(1,3-dimethyl-2,4,6-(1H,3H,5H)-trioxopyrimidin-5-ylidene)methylamino]-6-O-(4-methoxybenzyl)-D-galactitol

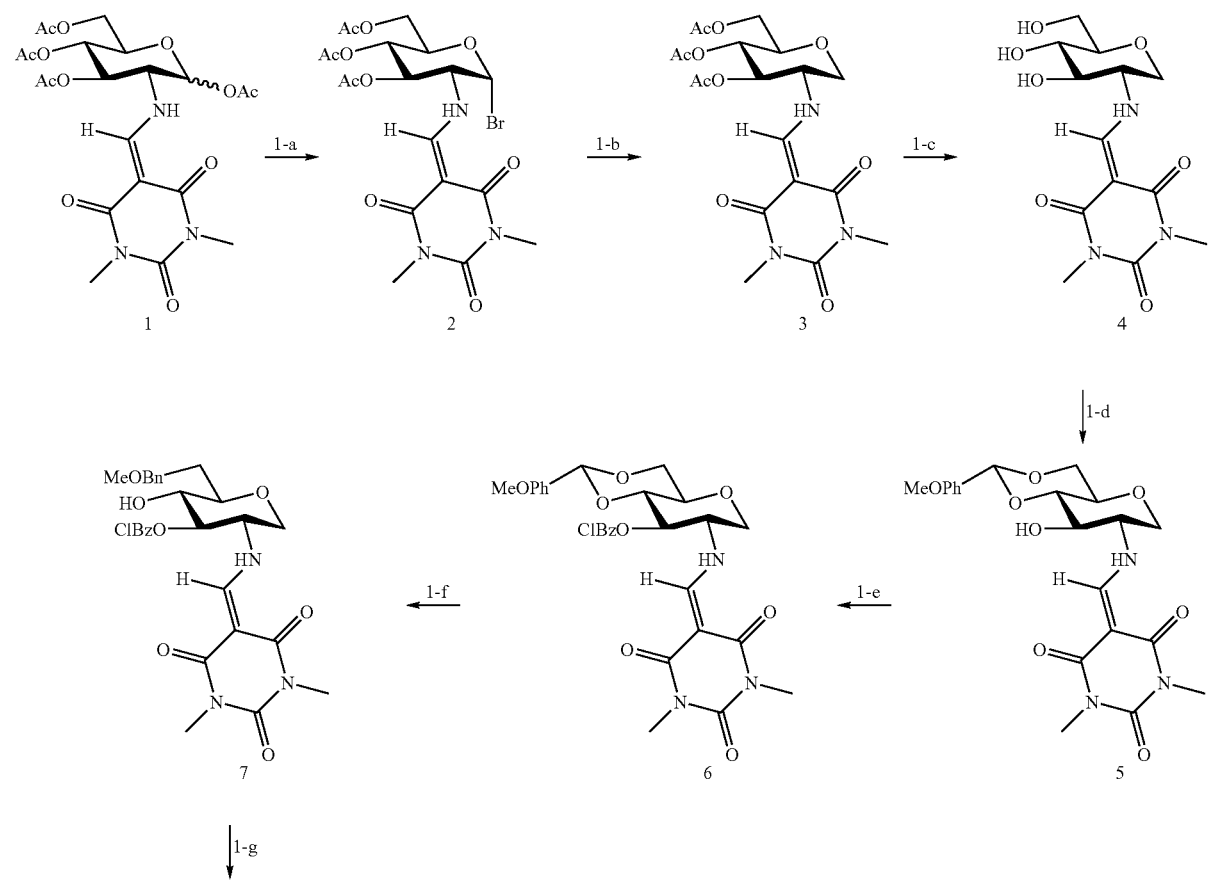

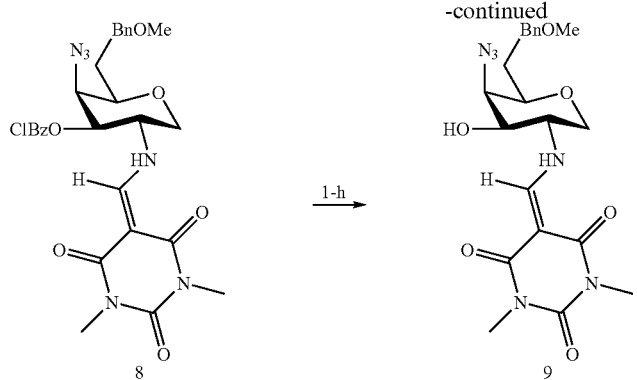

1-a. Synthesis of 2-deoxy-2-[(1,3-dimethyl-2,4,6-(1H,3H,5H)-trioxopyrimidin-5-yildene)methylamino]-3,4,6-O-triacetyl-α-D-glucopyranosyl bromide (2)

Compound 2 was synthesized according to the procedure described in General Method 1. Compound 2, (96%) as a white solid. $R_f$(product)≈0.75 in ethyl acetate; $\delta_H$ (400 MHz; CDCl$_3$) 2.00 (3 H, s), 2.05 (3 H, s), 2.09 (3 H, s), 3.29 (3 H, s), 3.30 (3 H, s), 3.78 (1 H, dt, J 9.9 Hz and J 3.6 Hz), 4.13 (1 H, dd, J 13.4 Hz and J 3.0 Hz), 4.35 (2 H, m), 5.19 (1 H, t, J 9.8 Hz), 5.46 (1 H, t, J 9.8 Hz), 6.50 (1 H, d, J 4.0 Hz), 8.13 (1 H, d, J 13.6 Hz) and 10.30 (1 H, br t, J 11.6 Hz); LCMS [M+H]$^+$=534.

1-b. Synthesis of 1,5-anhydro-2-deoxy-2-[(1,3-dimethyl-2,4,6-(1H,3H,5H)-trioxopyrimidin-5-ylidene)methylaminol]-3,4,6-O-triactyl-D-glucitol (3)

Compound 3 was synthesized according to the procedure described in General Method 2. Compound 3, quantitative yield; $R_f$ (product)≈0.65 in ethyl acetate, $\delta_H$ (400 MHz; CDCl$_3$) 2.03 (3 H, s), 2.04 (3 H, s), 2.09 (3 H, s), 3.28 (3 H, s), 3.30 (3 H, s), 3.53 (1 H, t, J 11.2 Hz), 3.68 (2 H, m), 4.14 (2 H, m), 4.25 (1 H, dd, J 12.6 Hz and J 5.0 Hz), 5.04 (1 H, t, J 9.4 Hz), 5.16 (1 H, t, J 9.6 Hz), 8.13 (1 H, d, J 13.6 Hz) and 10.10 (1 H, br t, J 11.4 Hz); $\delta_C$ (400 MHz; CDCl$_3$) 21.04 (CH$_3$×2), 21.17 (CH$_3$), 27.63 (CH$_3$), 28.33 (CH$_3$), 60.36 (CH), 62.32 (CH$_3$), 68.29 (CH), 68.62 (CH$_2$), 73.98 (CH), 76.97 (CH), 92.65 (C), 151.97 (C), 158.84 (CH), 162.65 (C), 164.91 (C), 169.57 (C), 170.36 (C) and 170.65 (C); LCMS [M+H]$^+$=456.

1-c. Synthesis of 1,5-anhydro-2-deoxy-2-[(1,3-dimethyl-2,4,6-(1H,3H,5H)-trioxopyrimidin-5-ylidene)methylaminol]-D-glucitol (4)

Compound 3 was treated as described by General Method 3 to provide 4; $R_f$ (product)≈0.00 in 1:1 ethyl acetate/light petroleum (40-60° C.), (S.M≈0.4). When system changed to 9:1 acetonitrile/methanol, $R_f$ (product)≈0.4. (S.M≈1.0); $\delta_H$ (400 MHz; DMSO) 3.13 (3 H, s), 3.14 (3 H, s), 3.47 (3 H, m), 3.65 (3 H, dd), 3.85 (1 H, d, J 6.0 Hz), 4.52 (1 H, t, J 5.8 Hz), 5.11 (1 H, d, J 4.8 Hz), 5.28 (1 H, d, J 5.6 Hz), 8.18 (1 H, d, J 14.4 Hz) and 10.03 (1 H, br t, J 8.4 Hz); $\delta_C$ (400 MHz; DMSO) 27.63 (CH$_3$), 28.29 (CH$_3$), 62.00 (CH$_2$), 62.90 (CH), 67.68 (CH$_2$), 71.37 (CH), 75.42 (CH), 82.22 (CH), 152.18 (C×2), 160.18 (CH), 162.71 (C) and 164.37 (C); LCMS [M+H]$^+$=330.

1-d. Synthesis of 1,5-anhydro-2-deoxy-2-[(1,3-dimethyl-2,4,6-(1H,3H,5H)-trioxopyrimidin-5-ylidene)methylamino]-4,6-O-(4-methoxybenzylidene)-D-glucitol (5)

Compound 4 was treated as described by General Method 4, to give the desired product 5 as a solid (86%); $R_f$ (product)≈0.1 in 1:1 ethyl acetate/light petroleum (40-60° C.), $\delta_H$ (400 MHz; CDCl$_3$) 3.29 (3 H, s), 3.30 (3 H, s), 3.48 (5 H, m), 3.70 (1 H, t, J 10.2 Hz), 3.81 (3 H, s), 3.83 (1 H, m), 4.11 (1 H, m), 4.32 (1 H, dd, J 10.4 Hz and J 4.8 Hz), 5.51 (1 H, s), 6.90 (2 H, d, J 8.8 Hz), 7.40 (2 H, d, J 8.4 Hz), 8.24 (1 H, d, J 13.6 Hz) and 10.20 (1 H, br t, J 11.5 Hz); LCMS [M+H]$^+$=448.

1-e. Synthesis of 1,5-anhydro-3-O-(4-chlorobenzoyl)-2-deoxy-2-[(1,3-dimethyl-2,4,6-(1H,3H,5H)-trioxopyrimidin-5-ylidene)methylaminol]-4,6-O-(4-methoxybenzylidene)-D-glucitol (6)

Compound 5 was treated according to General Method 5, to give the product 6 as a off-white solid (83%); $R_f$ (product)≈0.33 in 1:1 ethyl acetate/light petroleum (40-60° C.). (S.M≈0.17); $\delta_H$ (400 MHz; CDCl$_3$) 3.24 (3 H, s), 3.25 (3 H, s), 3.72 (8 H, m), 4.14 (1 H, t, J 5.5 Hz), 4.35 (1 H, t, J 5.4 Hz), 5.50 (1 H, s), 5.57 (1 H, t, J 9.6 Hz), 6.82 (2 H, dd, J 6.6 Hz and J 2.2 Hz), 7.30 (2 H, dd, J 6.8 Hz and J 2.0 Hz), 7.38 (2 H, dd, J 6.8 Hz and J 2.0 Hz), 7.93 (2 H, dd, J 6.6 Hz and J 2.2 Hz), 8.12 (1 H, d, J 13.6 Hz), and 10.20 (1 H, br t, J 11.6 Hz); LCMS [M+H]$^+$=586.

1-f. Synthesis of 1,5-anhydro-3-O-(4-chlorobenzoyl)-2-deoxy-2-[(1,3-dimethyl-2,4,6-(1H,3H,5H)-trioxopyrimidin-5-ylidene)methylaminol]-6-O-(4-methoxybenzyl)-D-glucitol (7)

Compound 6 was treated according to the procedure described in General Method 33 to give the product 7 as an off-white foam (93%); $R_f$(product)≈0.26 in 1:1 ethyl acetate/light petroleum (40-60° C.). (S.M≈0.33); $\delta_H$ (400 MHz; CDCl$_3$) 3.23 (3 H, s), 3.24 (3 H, s), 3.51 (2 H, m), 3.80 (8 H, m), 4.13 (1 H, dd, J 11.4 Hz and J 5.4 Hz), 4.52 (2 H, q, J 11.2 Hz), 5.27 (1 H, t, J 9.6 Hz), 6.87 (2 H, d, J 8.8 Hz), 7.26 (2 H, m), 7.40 (2 H, d, J 8.8 Hz), 7.93 (2 H, d, J 8.8 Hz), 8.11 (1 H, d, J 13.6 Hz), and 10.30 (1 H, br t, J 11.5 Hz); LCMS [M+H]$^+$=588.

EXAMPLE 2

Synthesis of a Galactitol Library—Preparation of Intermediates; General Procedures for Alkylation of the C-3 Position and Removal of the DTPM Group

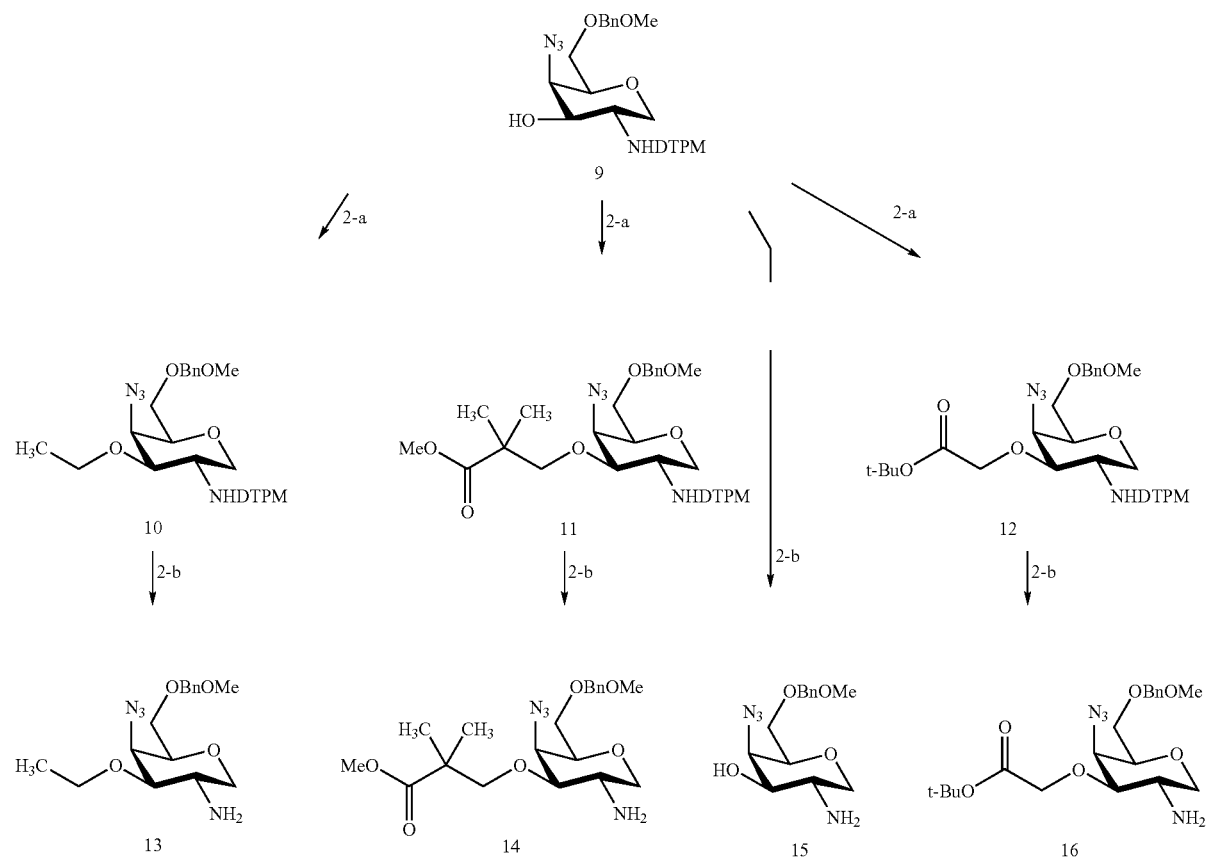

1 g. Synthesis of 1,5-anhydro-4-azido-3-O-(4-chlorobenzoyl)-2,4-dideoxy-2-[(1,3dimethyl-2,4,6-(1H, 3H,5H)-trioxopyrimidin-5-ylidene)methylamino]-6-O-(4-methoxybenzyl)-D-galactitol (8)

Compound 7 was treated according to the procedure described in General Method 6 to give compound 8, (93%) R$_f$ (product)≈0.62 in 1:1 ethyl acetate/light petroleum. Product recrystallised from isopropanol; LCMS [M+H]$^+$=613.

1-h. Synthesis of 1,5-anhydro-4-azido-3-O-(4-chlorobenzoyl)-2,4-dideoxy-2-[(1,3-dimethyl-2,4,6-(1H, 3H,5H)-trioxopyrimidin-5-ylidene)methylamino]-D-galactitol (9)

Compound 8 was reacted according to General Method 3, to give the desired product 9 (70%) as a white foam, δ$_H$ (400 MHz; CDCl$_3$) 3.25 (3 H, s), 3.26 (3 H, s), 3.65 (5 H, m), 3.80 (3 H, s), 4.09 (3 H, m), 4.50 (2 H, q, J 9.5 Hz and J 3.6 Hz), 6.89 (2 H, d, J 8.8 Hz), 7.26 (2 H, d, J 8.8 Hz), 8.21 (1 H, d, J 13.6 Hz), and 10.15 (1 H, br t, J 11.4 Hz); LCMS [M+H]$^+$=475.

2-a. Alkylation of the C-3 Position: Preparation of Compounds 10, 11 and 12

Compounds 10, 11, and 12 were prepared according to General Method 7.

| | Analytical Data | | |
|---|---|---|---|
| | Compound No. | | |
| | 10 | 11 | 12 |
| [M + H]$^+$ | 503 | 589 | 589 |

2-b. Removal of the DTPM Group at the C-2 Position. Preparation of Compounds 13, 14, 15 and 16

Compounds 13, 14, 15, and 16 were prepared according to General Method 8.

| Analytical Data. | | | | |
|---|---|---|---|---|
| | Compound | | | |
| | 13 | 14 | 15 | 16 |
| [M + H]$^+$ | 337 | 423 | 309 | 423 |

Data for 5-Azido-4-ethoxy-6-(4-methoxy-benzyloxymethyl)-tetrahydro-pyran-3-ylamine (13)

Yellow oil, yield (100%), $\delta_H$ (400 MHz; CDCl$_3$) 1.27 (3 H, t, J 7.0 Hz), 1.50 (2 H, br s), 3.06 (1 H, t, J 11.0 Hz), 3.21 (2 H, m), 3.52 (4 H, m), 3.78 (4 H, m), 3.93 (1 H, dd, J 10.8 Hz and J 4.6 Hz), 4.04 (1 H, d, J 3.2 Hz), 4.48 (2 H, q, J 14.8 Hz and J 11.6 Hz), 6.88 (2 H, d, J 8.4 Hz) and 7.26 (2 H, d, J 8.8 Hz); LCMS [M+H]$^+$=337.

2-c. Preparation of Intermediates: General Procedures from Preparation of Derivatives at the C-2 Position Compounds 17 to 51 were individually prepared according to one of General Methods 9,10, 11 and 12.

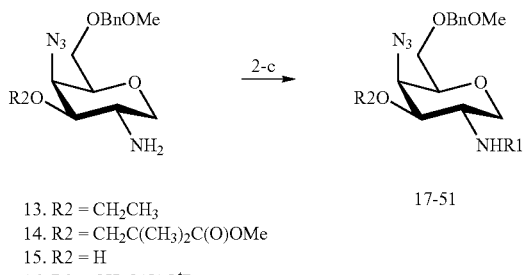

13. R2 = CH$_2$CH$_3$
14. R2 = CH$_2$C(CH$_3$)$_2$C(O)OMe
15. R2 = H
16. R2 = CH$_2$C(O)O$^t$Bu

Analytical Data: Example of a product of General Method 9: [3-Azido-5-(3-tert-butoxycarbonylamino-propionylamino)-2-(4-methoxy-benzyloxymethyl)-tetrahydro-pyran-4-yloxy]-acetic acid tert-butyl ester (33)

Sugar (16) (3.1 mmol) coupled to Boc-β-alanine (3.2 mmol) gave the title compound (33) as an off-white solid, in 69% yield after column chromatography (silica; 50% ethyl acetate in light petroleum (40-60° C.)), $\delta_H$ (400 MHz; CDCl$_3$) 1.42 (9 H, s), 1.49 (9 H, s), 2.43 (2 H, t, J 6.4 Hz), 2.95 (1 H, t, J 10.2 Hz), 3.48 (6 H, m), 3.81 (3 H, s), 4.07 (4 H, m), 4.47 (3 H, q, J 11.4 Hz and J 6.8 Hz), 5.24 (1 H, br. s.), 6.89 (2 H, d, J 8.8 Hz), 7.25 (2 H, d, J 8.4 Hz) and 7.51 (1 H, br. d, J 5.2 Hz); LCMS [M+H]$^+$=594.

Example of a Product of General Method 9: Acetic acid [5-azido-4-hydroxy-6-(4-methoxy-benzyloxymethyl)-tetrahydro-pyran-3-ylcarbamoyl]-methyl ester (45)

Sugar (15) (4.2 mmol), was coupled to acetoxyacetic acid (4.3 mmol) and after trituration with diethyl ether gave the title compound (45) as a white solid in 64%, $\delta_H$ (400 MHz; CDCl$_3$) 2.17 (3 H, s), 3.19 (1 H, t, J 10.8 Hz), 3.44 (1 H, d, J 7.2 Hz), 3.60 (3 H, m), 3.76 (1 H, m), 3.80 (3 H, s), 4.06 (3 H, m), 4.49 (2 H, q, J 10.2 Hz and J 2.4 Hz), 4.56 (2 H, s), 6.04 (1 H, d, J 6.8 Hz), 6.89 (2 H, d, J 6.8 Hz) and 7.26 (2 H, d, J 8.8 Hz); LCMS [M+H+Na]$^+$=431.

Example of a product of General Method 9: N-[5-Azido-4-hydroxy-6-(4-methoxy-benzyloxymethyl)-tetrahydro-pyran-3-yl]-succinamic acid methyl ester (18)

Sugar (15) (4.5 mmol), coupled to succinic acid mono methyl ester (4.8 mmol), after trituration with diethyl ether gave the title compound (18) (63%), as a white solid; $\delta_H$ (400 MHz; DMSO) 2.35 (2 H, dt, J 6.9 Hz and J 2.4 Hz), 2.47 (2 H, t, J 6.8 Hz), 2.89 (1 H, t, J 10.8 Hz), 3.43 (2 H, dd, J 5.8 Hz and 2.6 Hz), 3.56 (3 H, s), 3.64 (2 H, dd, J 11.0 Hz and J 5.0 Hz), 3.73 (3 H, s), 3.80 (3 H, m), 4.39 (2 H, q, J 10.9 Hz), 5.48 (1 H, d, J 4.4 Hz), 6.89 (2 H, dd, J 6.4 Hz and J 2.8 Hz), 7.23 (2 H, d, J 8.8 Hz) and 7.73 (1 H, d, J 8.0 Hz); $\delta_C$ (400 MHz; DMSO) 29.65 (CH$_3$), 30.80 (CH$_3$), 48.62 (CH$_2$), 52.12 (CH$_2$), 55.86 (CH$_2$), 63.92 (CH$_2$), 68.56 (CH), 69.85 (CH), 72.18 (CH), 72.76 (CH), 76.20 (CH$_2$), 114.30 (CH×2), 129.03 (CH×2), 130.68 (C), 159.32 (C), 171.73 (C) and 173.35 (C); LCMS [M+H+Na]$^+$=423.

Example of a product of General Method 10; {3-[5-Azido-4-hydroxy-6-(4-methoxy-benzyloxymethyl)-tetrahydro-pyran-3-yl]-ureido}-acetic acid ethyl ester (41)

Compound 41, white solid, yield 66%; $\delta_H$ (400 MHz; DMSO) 1.17 (3 H, t, J 6.8 Hz), 2.88 (1 H, t, J 10.6 Hz), 3.31 (2 H, s), 3.42 (2 H, m), 3.67 (9 H, m), 3.85 (1 H, dd, J 3.2 Hz and J 1.2 Hz), 4.06 (2 H, q, J 7.0 Hz), 4.39 (2 H, q, J 10.7 Hz), 5.56 (1 H, d, J 4.4 Hz), 6.09 (1 H, d, J 6.8 Hz), 6.28 (1 H, t, J 5.8 Hz), 6.89 (1 H, d, J 6.8 Hz) and 7.22 (1 H, d, J 6.8 Hz); $\delta_C$ (400 MHz; DMSO) 15.03 (CH$_3$), 42.28 (CH$_2$×2), 49.30 (CH$_3$), 55.88 (CH), 61.00 (CH$_2$), 64.13 (CH), 69.47 (CH$_2$), 69.84 (CH$_2$), 72.74 (CH), 76.06 (CH), 114.30 (CH×2), 129.03 (CH×2), 130.68 (C), 158.56 (C), 159.32 (C) and 171.57 (C); LCMS [M+H]$^+$=438.

Example of a product of General Method 11: [5-Acetylamino-3-azido-2-(4-methoxy-benzyloxymethyl)-tetrahydro-pyran-4yloxy]-acetic acid tert-butyl ester (36)

Derivatisation of the t-butyl sugar (16) (3.1 mmol) gave the title compound 36 as a yellow oil, 89%, $\delta_H$ (400 MHz; CDCl$_3$) 1.43 (9 H, s, C(CH$_3$)$_3$), 1.94 (3 H, s), 2.88 (1 H, t, J 10.0 Hz), 3.45 (4 H, m), 3.74 (3 H, s), 4.04 (4 H, m), 4.40 (3 H, m), 6.82 (2 H, d, J 8.8 Hz), 7.19 (2 H, d, J 8.8 Hz) and 7.41 (1 H, br d, J 5.2 Hz); LCMS [M+H]$^+$=465.

Example of a product of General Method 12: 3-[3-Azido-2-(4-methoxy-benzyloxymethyl)-5-(2-methoxycarbonyl-acetylamino)-tetrahydro-pyran-4-yloxy]-2,2-dimethyl-propionic acid methyl ester (51)

Derivatisation of the pivolate sugar (14) (3.6 mmol) gave the title compound as a brown oil (51) 75%; $\delta_H$ (400 MHz; CDCl$_3$) 1.16 (3 H, s), 1.24 (3 H, s), 3.35 (3 H, m), 3.57 (6 H, m), 3.68 (3 H, s), 3.73 (3 H, s), 3.81 (3 H, s), 4.28 (3 H, m), 4.46 (2 H, q, J 12.0 Hz and J 11.6 Hz), 6.89 (2 H, d, J 6.4 Hz) and 7.26 (2 H, d, J 6.0 Hz); LCMS [M+H]$^+$=523.

The table below represents all compounds made with derivatives at the 2-position.

TABLE 1

Intermediates for synthesis of Galactitol Library.

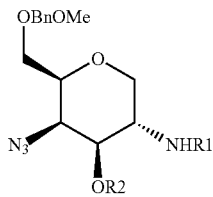

| No. | R1* | R2* | Molecular Ion | No. | R1 | R2 | Molecular Ion |
|---|---|---|---|---|---|---|---|
| 17 | R1a | R2d | $[M + H]^+ = 537$ | 35 | R1f | R2a | $[M + H]^+ = 508$ |
| 18 | R1a | R2c | $[M + Na]^+ = 423$ | 36 | R1g | R2d | $[M + H]^+ = 465$ |
| 19 | R1a | R2a | $[M + H]^+ = 451$ | 37 | R1g | R2c | $[M + H]^+ = 351$ |
| 20 | R1a | R2b | $[M + H]^+ = 537$ | 38 | R1g | R2a | $[M + H]^+ = 379$ |
| 21 | R1b | R2d | $[M + H]^+ = 565$ | 39 | R1g | R2b | $[M + H]^+ = 465$ |
| 22 | R1b | R2c | $[M + H]^+ = 451$ | 40 | R1h | R2d | $[M + H]^+ = 552$ |
| 23 | R1b | R2a | $[M + H]^+ = 479$ | 41 | R1h | R2c | $[M + H]^+ = 438$ |
| 24 | R1c | R2d | $[M + H]^+ = 656$ | 42 | R1h | R2a | $[M + H]^+ = 466$ |
| 25 | R1c | R2c | $[M + H]^+ = 542$ | 43 | R1h | R2b | $[M + H]^+ = 552$ |
| 26 | R1c | R2a | $[M + H]^+ = 570$ | 44 | R1i | R2d | $[M + H]^+ = 523$ |
| 26 | R1d | R2d | $[M + H]^+ = 656$ | 45 | R1i | R2c | $[M + Na]^+ = 431$ |
| 28 | R1d | R2c | $[M + H]^+ = 542$ | 46 | R1i | R2a | $[M + H]^+ = 437$ |
| 29 | R1d | R2a | $[M + H]^+ = 570$ | 47 | R1i | R2b | $[M + H]^+ = 523$ |
| 30 | R1e | R2d | $[M + H]^+ = 613$ | 48 | R1j | R2d | $[M + H]^+ = 523$ |
| 31 | R1e | R2c | $[M + H]^+ = 499$ | 49 | R1j | R2c | $[M + H]^+ = 409$ |
| 32 | R1e | R2a | $[M + H]^+ = 527$ | 50 | R1j | R2a | $[M + H]^+ = 437$ |
| 33 | R1f | R2d | $[M + H]^+ = 594$ | 51 | R1j | R2b | $[M + H]^+ = 523$ |
| 34 | R1f | R2c | $[M + H]^+ = 480$ | | | | |

*Sidearms for Tables 1 and 2 can be found at the end of Table 2.

2-d. Preparation of Derivatives Reduced at the C-4 Position

Compounds 52 to 86 were prepared according to General Method 13.

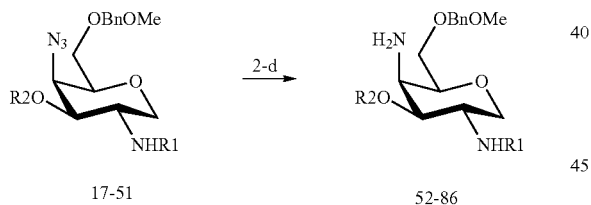

17-51 → 52-86

TABLE 1

Observed molecular ions of reduced azides

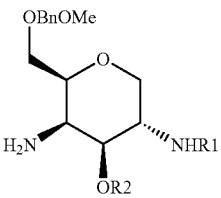

| No. | R1 | R2 | Molecular Ion | No. | R1 | R2 | Molecular Ion |
|---|---|---|---|---|---|---|---|
| 52 | R1a | R2d | $[M + H]^+ = 511$ | 70 | R1f | R2a | $[M + H]^+ = 482$ |
| 53 | R1a | R2c | $[M + H]^+ = 397$ | 71 | R1g | R2d | $[M + H]^+ = 439$ |
| 54 | R1a | R2a | $[M + H]^+ = 425$ | 72 | R1g | R2c | No Data |
| 55 | R1a | R2b | No Data | 73 | R1g | R2a | $[M + H]^+ = 353$ |

TABLE 1-continued

Observed molecular ions of reduced azides

| No. | R1 | R2 | Molecular Ion | No. | R1 | R2 | Molecular Ion |
|---|---|---|---|---|---|---|---|
| 56 | R1b | R2d | $[M + H]^+ = 539$ | 74 | R1g | R2b | $[M + H]^+ = 439$ |
| 57 | R1b | R2c | $[M + H]^+ = 425$ | 75 | R1h | R2d | $[M + H]^+ = 526$ |
| 58 | R1b | R2a | $[M + H]^+ = 453$ | 76 | R1h | R2c | $[M + H]^+ = 412$ |
| 59 | R1c | R2d | $[M + H]^+ = 588$ | 77 | R1h | R2a | $[M + H]^+ = 440$ |
| 60 | R1c | R2c | $[M + H]^+ = 474$ (loss of acetate) | 78 | R1h | R2b | $[M + H]^+ = 526$ |
| 61 | R1c | R2a | $[M + H]^+ = 502$ (loss of acetate) | 79 | R1i | R2d | $[M + H]^+ = 497$ |
| 62 | R1d | R2d | $[M + H]^+ = 588$ | 80 | R1i | R2c | $[M + H]^+ = 383$ |
| 63 | R1d | R2c | $[M + H]^+ = 474$ (loss of acetate) | 81 | R1i | R2a | $[M + H]^+ = 411$ |
| 64 | R1d | R2a | $[M + H]^+ = 544$ | 82 | R1i | R2b | $[M + H]^+ = 497$ |
| 65 | R1e | R2d | $[M + H]^+ = 587$ | 83 | R1j | R2d | $[M + H]^+ = 497$ |
| 66 | R1e | R2c | $[M + H]^+ = 431$ (loss of acetate) | 84 | R1j | R2c | $[M + H]^+ = 383$ |
| 67 | R1e | R2a | $[M + H]^+ = 501$ | 85 | R1j | R2a | $[M + H]^+ = 411$ |
| 68 | R1f | R2d | $[M + H]^+ = 568$ | 86 | R1j | R2b | $[M + H]^+ = 497$ |
| 69 | R1f | R2c | $[M + H]^+ = 454$ | | | | |

Sidearms for Example 2: Tables 1 and 2.

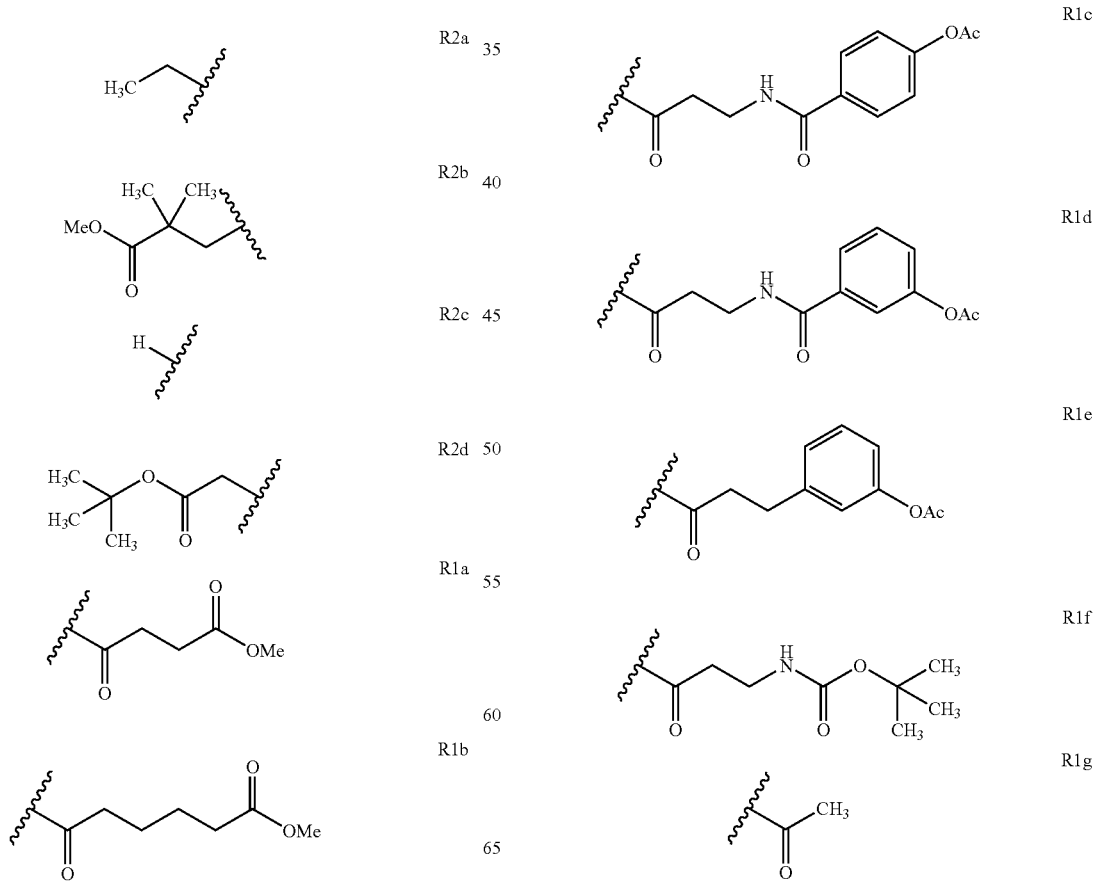

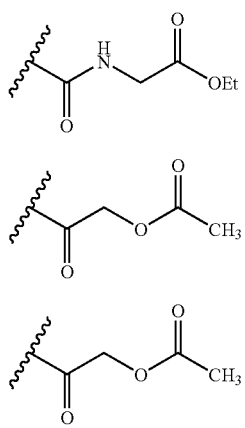

2-e. Final N-Acylation of Galactitol Derivatives in the C-4 Position

Compounds 87 to 416 were prepared in an automated fashion using chemistries according to General Method 9. As required, protecting groups on the sidearms, or the ring were hydrolytically cleaved in either a base or acid catalysed fashion, using either General Method 14 or 15.

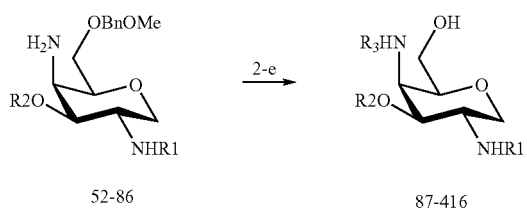

TABLE 3

Library of 1,5-Anhydro-galactitol Compounds

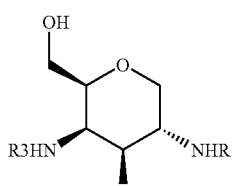

| Compound No. | R1 | R2 | R3 | Yield | Retention Time (mins) | HPLC Method |
|---|---|---|---|---|---|---|
| 87 | R1a | R2a | R3a | 70 | 4.72 | A |
| 88 | R1a | R2a | R3b | 83 | 4.28 | A |
| 89 | R1a | R2a | R3c | 74 | 4.90 | A |
| 90 | R1a | R2a | R3d | 38 | 4.44 | A |
| 91 | R1a | R2a | R3e | 10 | 4.73 | A |
| 92 | R1a | R2a | R3f | 44 | 4.53 | A |
| 92 | R1b | R2a | R3b | 64 | 4.73 | A |
| 94 | R1b | R2a | R3g | 77 | 4.35 | A |
| 95 | R1c | R2a | R3h | 82 | 5.33 | A |
| 96 | R1d | R2a | R3a | 50 | 4.28 | A |
| 97 | R1d | R2a | R3c | 42 | 4.00 | A |
| 98 | R1d | R2a | R3d | 85 | 4.46 | A |
| 99 | R1d | R2a | R3f | 21 | 4.62; | A |
| 100 | R1d | R2a | R3h | 84 | 4.55 | A |

TABLE 3-continued

Library of 1,5-Anhydro-galactitol Compounds

| Compound No. | R1 | R2 | R3 | Yield | Retention Time (mins) | HPLC Method |
|---|---|---|---|---|---|---|
| 101 | R1d | R2a | R3a | 100 | 4.56 | A |
| 102 | R1d | R2a | R3b | 91 | 4.72 | A |
| 103 | R1d | R2a | R3c | 70 | 4.64 | A |
| 104 | R1d | R2a | R3d | 92 | 5.27 | A |
| 105 | R1d | R2a | R3f | 50 | 4.73 | A |
| 106 | R1e | R2a | R3i | 100 | 3.54 | A |
| 107 | R1e | R2a | R3i | 61 | 4.53 | A |
| 108 | R1e | R2a | R3b | 97 | 5.74 | A |
| 109 | R1e | R2a | R3d | 93 | 6.02 | A |
| 110 | R1e | R2a | R3e | 10 | 6.18 | A |
| 111 | R1e | R2a | R3f | 62 | 5.74 | A |
| 112 | R1f | R2a | R3b | 80 | 4.55 | A |
| 113 | R1f | R2a | R3d | 36 | 5.17 | A |
| 114 | R1g | R2a | R3j | 100 | 4.55 | A |
| 115 | R1g | R2a | R3k | 96 | 5.36 | A |
| 116 | R1g | R2a | R3l | 100 | 6.66 | A |
| 117 | R1g | R2a | R3m | 100 | 7.01 | A |
| 118 | R1g | R2a | R3n | 100 | 6.39 | A |
| 119 | R1g | R2a | R3o | 97 | 4.44 | A |
| 120 | R1g | R2a | R3o | 95 | 4.37 | A |
| 121 | R1g | R2a | R3p | 90 | 5.40 | A |
| 122 | R1f | R2a | R3j | 90 | 4.92 | A |
| 123 | R1f | R2a | R3k | 93 | 5.14 | A |
| 124 | R1f | R2a | R3n | 96 | 6.84 | A |
| 125 | R1f | R2a | R3n | 95 | 7.19 | A |
| 126 | R1f | R2a | R3o | 72 | 6.48 | A |
| 127 | R1f | R2a | R3q | 63 | 2.60 | A |
| 128 | R1h | R2a | R3l | 79 | 4.07 | A |
| 129 | R1h | R2a | R3m | 77 | 3.52 | A |
| 130 | R1h | R2a | R3n | 100 | 4.09 | A |
| 131 | R1h | R2a | R3o | 54 | 5.36 | A |
| 132 | R1h | R2a | R3q | 74 | 5.50 | A |
| 133 | R1h | R2a | R3p | 91 | 3.78 | A |
| 134 | R1i | R2a | R3m | 79 | 4.05 | A |
| 135 | R1i | R2a | R3r | 77.5 | 1.50 | A |
| 136 | R1i | R2a | R3s | 69 | 3.77 | A |
| 137 | R1i | R2a | R3t | 100 | 5.26 | A |
| 138 | R1i | R2a | R3n | 93 | 5.38 | A |
| 139 | R1i | R2a | R3v | 71 | 3.83 | A |
| 140 | R1i | R2a | R3m | 87 | 4.79 | A |
| 141 | R1i | R2a | R3n | 95 | 5.65 | A |
| 142 | R1i | R2a | R3r | 78 | 5.08 | A |
| 143 | R1j | R2a | R3s | 81 | 5.65 | A |
| 144 | R1j | R2a | R3t | 98 | 5.27 | A |
| 145 | R1j | R2a | R3n | 93 | 5.08 | A |
| 146 | R1i | R2a | R3v | 99 | 4.92 | A |
| 147 | R1b | R2a | R3m | 90 | 4.92 | A |
| 148 | R1b | R2a | R3n | 45 | 5.10 | A |
| 149 | R1b | R2a | R3r | 97 | 5.17 | A |
| 150 | R1b | R2a | R3s | 89 | 5.19 | A |
| 151 | R1b | R2a | R3t | 82 | 5.54 | A |
| 152 | R1b | R2a | R3n | 95 | 5.63 | A |
| 153 | R1b | R2a | R3v | 62 | 6.39 | A |
| 154 | R1a | R2b | R3b | 95 | 6.73 | A |
| 155 | R1a | R2b | R3d | 100 | 7.49 | A |
| 156 | R1b | R2b | R3b | 97 | 6.37 | A |
| 157 | R1b | R2b | R3d | 97 | 5.00 | A |
| 158 | R1c | R2b | R3w | 16.5 | 7.47 | A |
| 159 | R1c | R2b | R3b | 98.5 | 5.27 | A |
| 160 | R1c | R2b | R3d | 99 | 5.01 | A |
| 161 | R1c | R2b | R3g | 40 | 4.09 | A |
| 162 | R1d | R2b | R3b | 70.5 | 4.72 | A |
| 163 | R1d | R2b | R3d | 69 | 5.74 | A |
| 164 | R1d | R2b | R3g | 95 | 5.19 | A |

TABLE 3-continued

Library of 1,5-Anhydro-galactitol Compounds

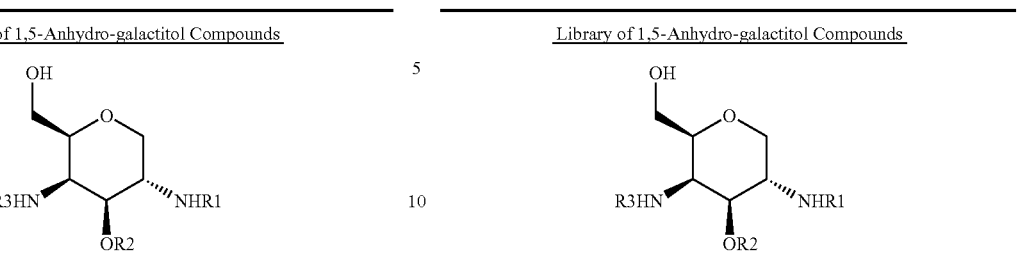

| Compound No. | R1 | R2 | R3 | Yield | Retention Time (mins) | HPLC Method |
|---|---|---|---|---|---|---|
| 165 | R1e | R2b | R3w | 80 | 4.62 | A |
| 166 | R1e | R2b | R3b | 100 | 4.28; | A |
| 167 | R1e | R2b | R3d | 100 | 4.62 | A |
| 168 | R1e | R2b | R3g | 63 | 4.28 | A |
| 169 | R1f | R2b | R3d | 97 | 4.44 | A |
| 170 | R1f | R2b | R3j | 100 | 4.37 | A |
| 171 | R1f | R2b | R3k | 91 | 4.62 | A |
| 172 | R1f | R2b | R3l | 97 | 4.18 | A |
| 173 | R1f | R2b | R3m | 65 | 4.07 | A |
| 174 | R1f | R2b | R3x | 91 | 4.64 | A |
| 175 | R1f | R2b | R3g | 54 | 4.99 | A |
| 176 | R1h | R2b | R3l | 85 | 6.94 | A |
| 177 | R1h | R2b | R3k | 100 | 6.09 | A |
| 178 | R1h | R2b | R3l | 100 | 4.92 | A |
| 179 | R1h | R2b | R3m | 92 | 4.53 | A |
| 180 | R1h | R2b | R3x | 90 | 5.19 | A |
| 181 | R1i | R2b | R3m | 83 | 4.61 | A |
| 182 | R1i | R2b | R3p | 15 | 1.69 | A |
| 183 | R1i | R2b | R3r | 100 | 4.09 | A |
| 184 | R1i | R2b | R3s | 100 | 1.69; | A |
| 185 | R1i | R2b | R3t | 96 | 4.18 | A |
| 186 | R1i | R2b | R3u | 100 | 4.46 | A |
| 187 | R1i | R2b | R3v | 100 | 4.94 | A |
| 188 | R1i | R2b | R3m | 97 | 1.71 | A |
| 189 | R1i | R2b | R3p | 98 | 1.69 | A |
| 190 | R1i | R2b | R3r | 84 | 2.07 | A |
| 191 | R1j | R2b | R3s | 100 | 2.26 | A |
| 192 | R1i | R2b | R3t | 100 | 1.69 | A |
| 193 | R1i | R2b | R3u | 70 | 2.26 | A |
| 194 | R1i | R2b | R3v | 100 | 1.6 | A |
| 195 | Ru | R2b | R3g | 100 | 3.00 | A |
| 196 | R1a | R2c | R3w | 100 | 4.41 | A |
| 197 | R1a | R2c | R3a | 50 | 0.55 | A |
| 198 | R1a | R2c | R3b | 96 | 1.78 | A |
| 199 | R1a | R2c | R3c | 58 | 1.69 | A |
| 200 | R1a | R2c | R3d | 95 | 2.35 | A |
| 201 | R1a | R2c | R3f | 32 | 2.26 | A |
| 202 | R1a | R2c | R3g | 6 | 4.14 | A |
| 203 | R1b | R2c | R3b | 100 | 3.94 | A |
| 204 | R1b | R2c | R3d | 100 | 4.75 | A |
| 205 | R1b | R2c | R3f | 32 | 4.9 | A |
| 206 | R1b | R2c | R3i | 83 | 1.8 | A |
| 207 | R1c | R2c | R3w | 77 | 1.69 | A |
| 208 | R1c | R2c | R3a | 44 | 2.17 | A |
| 209 | R1c | R2c | R3b | 99 | 4.33 | A |
| 210 | R1c | R2c | R3c | 43 | 2.26 | A |
| 211 | R1c | R2c | R3d | 93 | 3.34 | A |
| 212 | R1d | R2c | R3c | 94 | 4.18 | A |
| 213 | R1d | R2c | R3d | 90 | 5.36 | A |
| 214 | R1d | R2c | R3e | 15 | 2.17 | A |
| 215 | R1d | R2c | R3f | 91 | 1.89 | A |
| 216 | R1e | R2c | R3i | 100 | 1.78 | A |
| 217 | R1e | R2c | R3w | 97 | 4.55 | A |
| 218 | R1e | R2c | R3a | 80 | 6.20 | A |
| 219 | R1e | R2c | R3b | 94 | 3.25 | A |
| 220 | R1e | R2c | R3c | 62 | 4.09 | A |
| 221 | R1e | R2c | R3d | 91 | 4.35 | A |
| 222 | R1e | R2c | R3f | 37 | 4.48 | A |
| 223 | R1f | R2c | R3b | 100 | 4.83 | A |
| 224 | R1f | R2c | R3d | 96 | 5.28 | A |
| 225 | R1g | R2c | R3j | 100 | 1.78 | A |
| 226 | R1g | R2c | R3k | 100 | 4.00 | A |
| 227 | R1g | R2c | R3l | 100 | 4.00 | A |
| 228 | R1g | R2c | R3m | 100 | 5.74 | A |
| 229 | R1g | R2c | R3x | 100 | 3.73 | A |
| 230 | R1g | R2c | R3o | 100 | 5.10 | A |
| 231 | R1g | R2c | R3g | 100 | 4.09 | A |
| 232 | R1g | R2c | R3p | 98 | 5.56 | A |
| 233 | R1g | R2c | R3r | 95 | 6.55 | A |
| 234 | R1f | R2c | R3j | 88 | 6.39 | A |
| 235 | R1f | R2c | R3k | 85 | 5.13 | A |
| 236 | R1f | R2c | R3l | 89 | 4.78 | A |
| 237 | R1f | R2c | R3m | 94 | 3.82 | A |
| 238 | R1f | R2c | R3x | 84 | 4.09 | A |
| 239 | R1f | R2c | R3o | 98 | 3.08 | A |
| 240 | R1f | R2c | R3q | 98 | 3.54 | A |
| 241 | R1f | R2c | R3p | 94 | 3.73 | A |
| 242 | R1h | R2c | R3j | 100 | 3.91 | A |
| 243 | R1h | R2c | R3k | 86 | 5.36 | A |
| 244 | R1h | R2c | R3l | 98 | 4.83 | A |
| 245 | R1h | R2c | R3m | 96 | 2.35 | A |
| 246 | R1h | R2c | R3x | 100 | 5.28 | A |
| 247 | R1f | R2c | R3r | 88 | 5.13 | A |
| 248 | R1h | R2c | R3o | 97 | 4.78 | A |
| 249 | R1h | R2c | R3q | 98 | 4.88 | A |
| 250 | R1h | R2c | R3p | 98 | 4.53 | A |
| 251 | R1h | R2c | R3q | 100 | 4.68 | A |
| 252 | R1i | R2c | R3m | 91 | 4.73 | A |
| 253 | R1i | R2c | R3p | 100 | 4.88 | A |
| 254 | R1i | R2c | R3s | 98 | 4.73 | A |
| 255 | R1i | R2c | R3t | 82 | 5.37 | A |
| 256 | R1i | R2c | R3u | 100 | 6.50 | A |
| 257 | R1i | R2c | R3v | 52 | 5.18 | A |
| 258 | R1i | R2c | R3m | 92 | 5.23 | A |
| 259 | R1j | R2c | R3p | 98 | 5.03 | A |
| 260 | R1j | R2c | R3r | 4 | 5.18 | A |
| 261 | R1j | R2c | R3s | 100 | 5.28 | A |
| 262 | R1j | R2c | R3t | 94 | 5.13 | A |
| 263 | R1j | R2c | R3u | 100 | 5.0;0 | A |
| 264 | R1j | R2c | R3v | 100 | 6.39 | A |
| 265 | R1j | R2c | R3g | 71 | 4.99 | A |
| 266 | R1b | R2c | R3m | 100 | 4.83 | A |
| 267 | R1b | R2c | R3p | 98 | 6.50 | A |
| 268 | R1b | R2c | R3r | 100 | 4.92 | A |
| 269 | R1b | R2c | R3s | 63 | 5.14 | A |
| 270 | R1b | R2c | R3t | 95 | 6.84 | A |
| 271 | R1b | R2c | R3u | 91 | 7.19 | A |
| 272 | R1b | R2c | R3v | 95 | 6.48 | A |
| 273 | R1b | R2d | R3i | 55 | 2.60 | A |
| 274 | R1b | R2d | R3w | 11 | 3.52 | A |
| 275 | R1b | R2d | R3a | 48 | 3.75 | A |
| 276 | R1b | R2d | R3b | 48 | 5.36 | A |
| 277 | R1b | R2d | R3d | 85 | 5.50 | A |
| 278 | R1b | R2d | R3e | 11 | 3.78 | A |
| 279 | R1b | R2d | R3f | 46 | 4.05 | A |
| 280 | R1f | R2d | R3i | 73 | 1.50 | A |
| 281 | R1f | R2d | R3w | 21 | 3.77 | A |
| 282 | R1f | R2d | R3b | 81 | 5.26 | A |
| 283 | R1f | R2d | R3d | 91 | 5.38 | A |
| 284 | R1f | R2d | R3f | 78 | 3.83 | A |
| 285 | R1g | R2d | R3j | 100 | 4.79 | A |
| 286 | R1g | R2d | R3k | 100 | 5.65 | A |
| 287 | R1g | R2d | R3l | 100 | 5.08 | A |
| 288 | R1g | R2d | R3m | 100 | 5.65 | A |
| 289 | R1g | R2d | R3o | 100 | 5.27 | A |
| 290 | R1g | R2d | R3r | 100 | 5.08 | A |
| 291 | R1f | R2d | R3j | 72 | 4.92 | A |
| 292 | R1f | R2d | R3l | 100 | 5.08 | A |

TABLE 3-continued

Library of 1,5-Anhydro-galactitol Compounds

| Compound No. | R1 | R2 | R3 | Yield | Retention Time (mins) | HPLC Method |
|---|---|---|---|---|---|---|
| 293 | R1f | R2d | R3x | 28 | 5.10 | A |
| 294 | R1f | R2d | R3o | 25 | 5.17 | A |
| 295 | R1f | R2d | R3r | 100 | 5.19 | A |
| 296 | R1h | R2d | R3k | 72 | 5.54 | A |
| 297 | R1j | R2d | R3p | 56 | 5.63 | A |
| 298 | R1j | R2d | R3r | 66 | 5.10 | A |
| 299 | R1j | R2d | R3t | 42 | 6.73 | A |
| 300 | R1j | R2d | R3u | 100 | 7.49 | A |
| 301 | R1j | R2d | R3v | 100 | 6.37 | A |
| 302 | R1b | R2d | R3r | 5 | 5.00 | A |
| 303 | R1b | R2d | R3u | 100 | 7.47 | A |
| 304 | R1c | R2a | R3b | 100 | 5.27 | A |
| 305 | R1e | R2a | R3w | 88 | 4.72 | A |
| 306 | R1a | R2a | R3y | 64 | 4.61 | A |
| 307 | R1b | R2a | R3h | 95 | 1.69 | A |
| 308 | R1b | R2a | R3w | 13 | 4.09 | A |
| 309 | R1b | R2a | R3a | 76 | 1.69 | A |
| 310 | R1b | R2a | R3f | 59 | 4.18 | A |
| 311 | R1c | R2a | R3y | 90 | 4.46 | A |
| 312 | R1e | R2a | R3z | 84 | 4.94 | A |
| 313 | R1f | R2a | R3i | 100 | 1.71 | A |
| 314 | R1f | R2a | R3w | 72 | 1.69 | A |
| 315 | R1f | R2a | R3a | 64 | 2.07 | A |
| 316 | R1f | R2a | R3e | 82 | 2.26 | A |
| 317 | R1f | R2a | R3f | 98 | 1.69 | A |
| 318 | R1i | R2a | R31 | 42 | 2.26 | B |
| 319 | R1i | R2a | R32 | 78 | 1.60 | B |
| 320 | R1j | R2a | R32 | 56 | 3.00 | B |
| 321 | R1a | R2b | R33 | 70 | 4.41 | A |
| 322 | R1a | R2b | R3f | 90 | 0.55 | A |
| 323 | R1b | R2b | R3w | 94 | 1.78 | B |
| 324 | R1b | R2b | R3c | 69 | 1.69 | B |
| 325 | R1b | R2b | R3e | 12 | 2.35 | B |
| 326 | R1d | R2b | R3i | 98 | 2.26 | B |
| 327 | R1d | R2b | R3z | 78 | 4.14 | A |
| 328 | R1d | R2b | R3w | 82 | 2.33 | B |
| 329 | R1e | R2b | R3z | 66 | 4.75 | A |
| 330 | R1e | R2b | R3c | 81 | 4.9 | B |
| 331 | R1f | R2b | R3i | 100 | 1.8 | B |
| 332 | R1f | R2b | R3w | 91 | 1.69 | B |
| 333 | R1f | R2b | R3c | 93 | 2.17 | B |
| 334 | R1a | R2c | R3z | 52 | 4.33 | A |
| 335 | R1b | R2c | R3i | 98 | 2.26 | B |
| 336 | R1b | R2c | R3a | 28 | 3.34 | B |
| 337 | R1d | R2c | R3z | 60 | 4.18 | A |
| 338 | R1e | R2c | R3z | 23 | 4.73 | A |
| 339 | R1f | R2c | R3i | 100 | 2.17 | B |
| 340 | R1f | R2c | R3z | 87 | 1.89 | A |
| 341 | R1f | R2c | R3c | 100 | 2.35 | B |
| 342 | R1f | R2c | R3f | 48 | 4.55 | B |
| 343 | R1b | R2d | R3s | 50 | 6.20 | A |
| 344 | R1a | R2b | R3i | 22 | 3.25 | A |
| 345 | R1a | R2b | R3w | 100 | 4.09 | A |
| 346 | R1a | R2c | R3e | 34 | 4.35 | A |
| 347 | R1b | R2a | R3e | 53 | 4.48 | A |
| 348 | R1f | R2a | R3c | 76 | 1.78 | A |
| 349 | R1b | R2b | R3i | 85 | 1.48 | B |
| 350 | R1b | R2b | R3a | 19 | 1.78 | B |
| 351 | R1c | R2a | R3g | 41 | 5.74 | A |
| 352 | R1d | R2a | R3w | 80 | 3.73 | A |
| 353 | R1h | R2d | R3x | 46 | 5.13 | A |
| 354 | R1b | R2a | R3d | 62 | 5.00 | A |
| 355 | R1i | R2b | R32 | 53 | 1.41 | B |
| 356 | R1j | R2b | R32 | 75 | 1.67 | B |
| 357 | R1b | R2b | R32 | 41 | 1.72 | B |
| 358 | R1b | R2b | R3m | 52 | 4.88 | A |
| 359 | R1b | R2b | R3r | 84 | 4.49 | A |
| 360 | R1b | R2b | R3s | 64 | 5.57 | A |
| 361 | R1b | R2b | R3t | 63 | 6.87 | A |
| 362 | R1b | R2b | R3u | 100 | 7.13 | A |
| 363 | R1b | R2b | R3v | 51 | 6.44 | A |
| 364 | R1i | R2c | R32 | 100 | 59 | B |
| 365 | R1j | R2c | R32 | 42 | 3.36 | B |
| 366 | R1b | R2c | R32 | 60 | 4.1 | A |
| 367 | R1j | R2d | R32 | 7 | 4.14 | A |
| 368 | R1b | R2d | R32 | 25 | 4.53 | A |
| 369 | R1a | R2e | R3c | 87 | 4.26 | A |
| 370 | R1c | R2e | R3a | 85 | 4.46 | A |
| 371 | R1h | R2e | R3o | 53 | 4.73 | A |
| 372 | R1i | R2e | R3v | 100 | 5.57 | A |
| 373 | R1k | R2b | R3b | 25 | 5.19 | A |
| 374 | R1l | R2b | R3b | 95 | 5.28 | A |
| 375 | R1l | R2b | R3d | 100 | 5.38 | A |
| 376 | R1m | R2b | R3d | 50 | 4.73 | A |
| 377 | R1n | R2b | R3k | 53 | 4.55 | A |
| 378 | R1k | R2c | R3b | 72 | 5.36 | A |
| 379 | R1k | R2c | R3d | 54 | 5.56 | A |
| 380 | R1k | R2c | R3u | 74 | 7.68 | A |
| 381 | R1b | R2f | R3i | 47 | 4.48 | A |
| 382 | R1b | R2f | R3b | 90 | 5.68 | A |
| 383 | R1b | R2f | R3d | 84 | 5.78 | A |
| 384 | R1f | R2f | R3i | 69 | 4.28 | A |
| 385 | R1f | R2f | R3b | 83 | 5.58 | A |
| 386 | R1f | R2f | R3d | 89 | 5.68 | A |
| 387 | R1g | R2f | R3m | 45 | 5.68 | A |
| 388 | R1f | R2f | R3o | 66 | 5.48 | A |
| 389 | R1f | R2f | R3p | 32 | 5.27 | A |
| 390 | R1h | R2f | R3k | 59 | 6.28 | A |
| 391 | R1h | R2f | R31 | 91 | 5.65 | A |
| 392 | R1h | R2f | R3p | 97 | 5.82 | A |
| 393 | R1h | R2f | R3r | 97 | 5.01 | A |
| 394 | R1j | R2f | R3m | 81 | 5.28 | A |
| 395 | R1j | R2f | R3p | 91 | 5.78 | A |
| 396 | R1j | R2f | R3t | 92 | 6.78 | A |
| 397 | R1j | R2f | R3u | 99 | 7.33 | A |
| 398 | R1j | R2f | R3v | 100 | 6.63 | A |
| 399 | R1b | R2f | R3p | 89 | 5.91 | A |
| 400 | R1b | R2f | R3s | 82 | 6.18 | A |
| 401 | R1b | R2f | R3t | 100 | 7.03 | A |
| 402 | R1b | R2f | R3u | 88 | 7.83 | A |
| 403 | R1i | R2b | R3i | 54 | 4.4 | A |
| 404 | R1d | R2e | R31 | 70 | 3.82 | A |
| 405 | R1i | R2a | R3c | 39 | 4.46 | B |
| 406 | R1i | R2c | R3z | 69 | 4.18 | A |
| 407 | R1f | R2f | R33 | 21 | 10.48 | A |
| 408 | R1h | R2f | R3m | 58 | 5.58 | A |
| 409 | R1h | R2f | R3x | 92 | 5.60 | A |
| 410 | R1i | R2f | R3g | 73 | 6.2 | A |
| 411 | R1b | R2f | R3m | 46 | 5.68 | A |
| 412 | R1k | R2b | R3r | 50 | 5.14 | A |
| 413 | R1k | R2b | R3s | 54 | 6.05 | A |
| 414 | R1k | R2b | R3t | 88.5 | 7.15 | A |
| 415 | R1k | R2b | R3u | 100 | 7.35 | A |
| 416 | R1k | R2b | R3v | 100 | 6.79 | A |

Functional Groups for Table 3 Galactitol Library
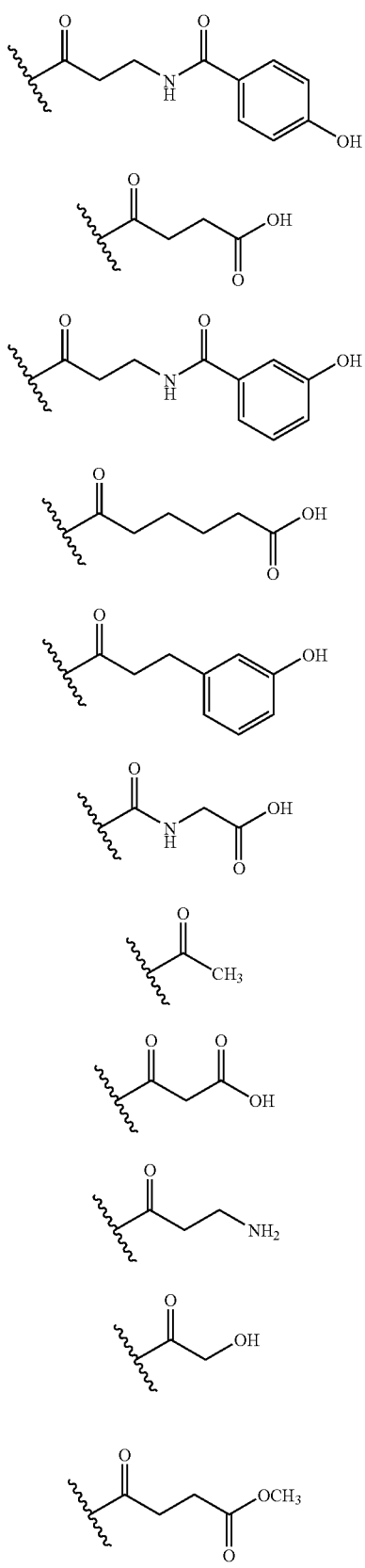
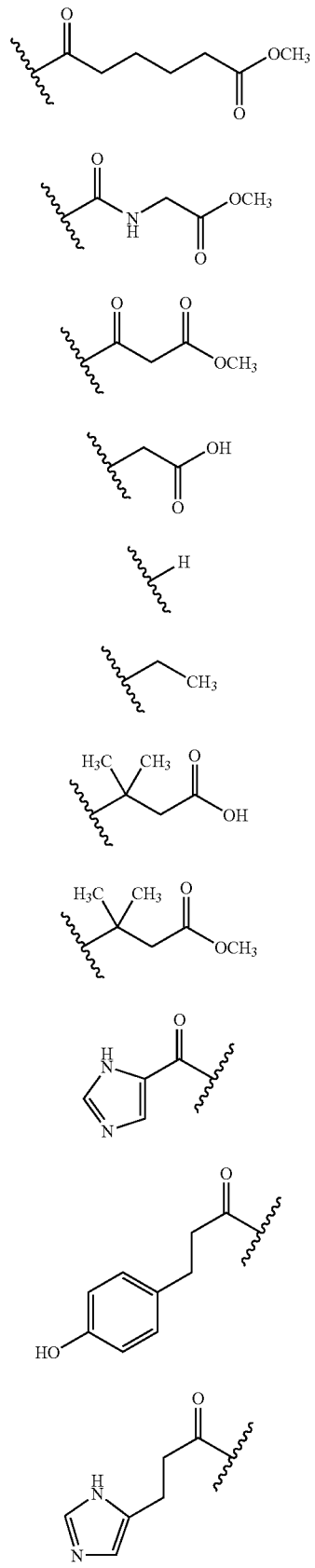

R3d = R1e
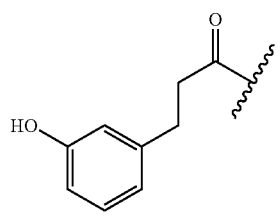
R3e
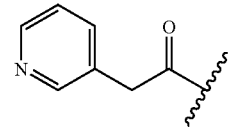
R3f
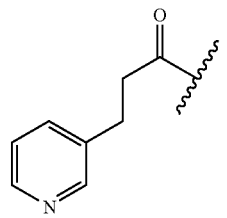
R3g
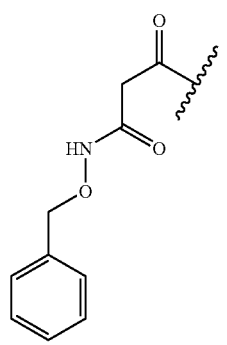
R3h = R1i
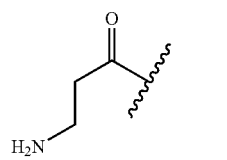
R3i
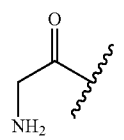
R3j
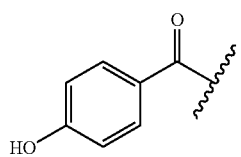
R3k
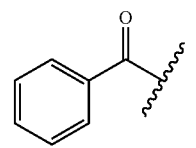
R3l
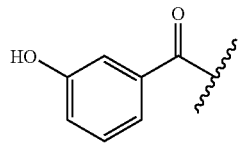
R3m
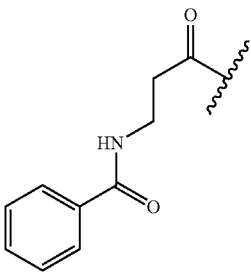
R3n = R1a
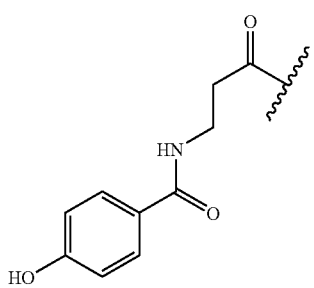
R3o
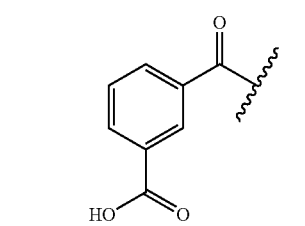
R3p
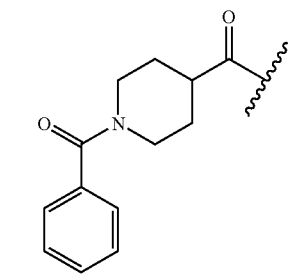
R3q = R1c
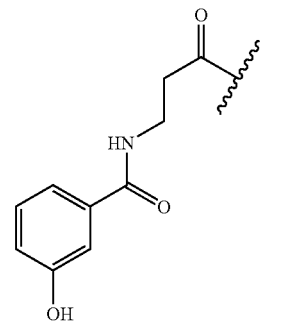

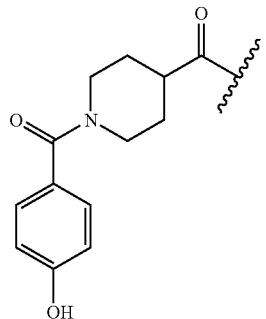 R3r
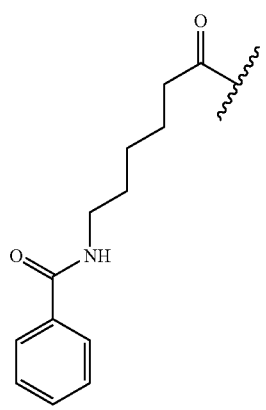 R3s
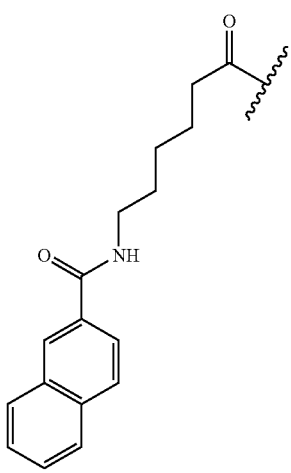 R3t
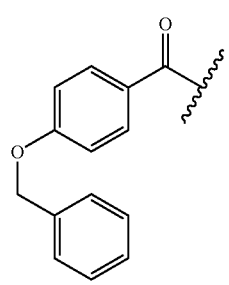 R3u
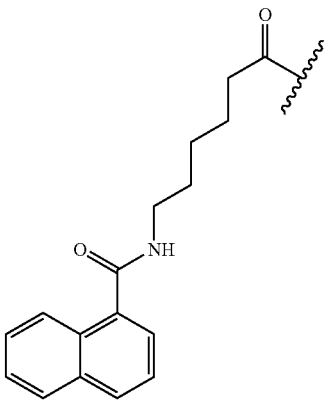 R3v
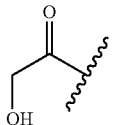 R3w = R1j
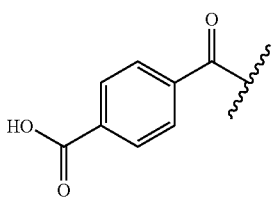 R3x
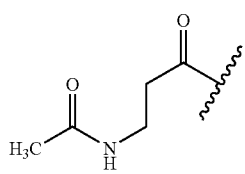 R3y
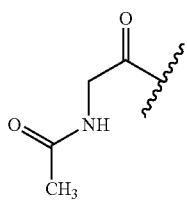 R3z
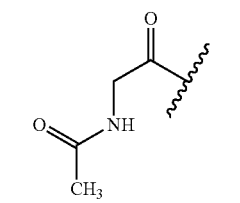 R3l
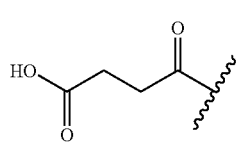 R32 = R1b -continued

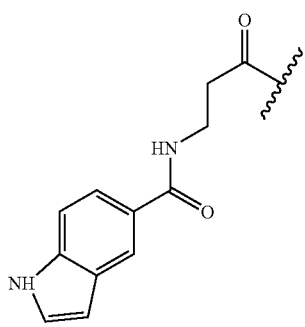

R33

HPLC Methods for Compounds in Table 3.

Method A

| Time | H₂O % | MeCN % | Flow rate ml/min |
|---|---|---|---|
| 0 | 100 | 0 | 2 |
| 2 | 100 | 0 | 2 |
| 10 | 40 | 60 | 2 |
| 12 | 0 | 100 | 2 |

Agilent SB Zorbax C18 4.6×50 mm (5 μm, 80 Å)
LC Mobile Phase: Acetonitrile: Water 0.1% formic acid Method B

| Time | H₂O % | MeCN % | Flow rate ml/min |
|---|---|---|---|
| 0 | 100 | 0 | 2 |
| 1 | 100 | 0 | 2 |
| 7 | 65 | 35 | 2 |
| 8 | 0 | 100 | 2 |
| 9 | 0 | 100 | 2 |

Agilent SB Zorbax Phenyl 4.6×150 mm (5 μm)
LC Mobile Phase: Acetonitrile: Water 0.1% formic acid
¹H-NMR Data for Three Compounds of Final Library.

Compound 238

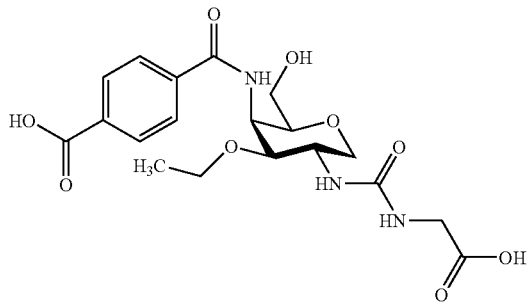

$\delta_H$ (400 MHz; CDCl₃) 1.01 (3 H, t, J 7.0 Hz), 2.49 (2H expected), 2.95 (1 H, t, J 10.9 Hz), 3.30-3.80 (6 H expected), 3.90 (1 H, m), 4.00 (1 H, dd, J 10.6 Hz and J 5.4 Hz), 4.63 (1 H, br. s), 4.75 (1 H, dd, J 9.4 Hz and J 3.4 Hz), 6.00 (1 H, d, J 6.4 Hz), 6.16 (1 H, t, J 5.8 Hz), 7.55 (1 H, t, J 7.8 Hz), 8.02 (2 H, t, J 6.4 Hz), 8.25 (1 H, d, J 10.0 Hz) and 8.33 (1 H, d, J 1.2 Hz).

Compound 200

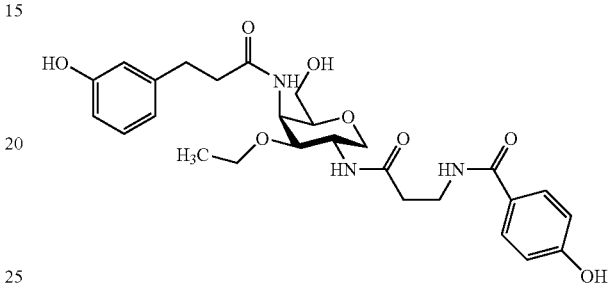

$\delta_H$ (400 MHz; CDCl₃) 0.94 (3 H, t, J 7.0 Hz), 1.07 (2 H, t, J 6.8 Hz), 2.30-2.40 (4 H expected), 2.49 (2 H expected), 2.60-3.00 (4 H expected), 3.30-3.85 (4 H expected), 3.91-4.10 (2 H, m), 4.44 (1 H, dd, J 9.8 Hz and J 4.2 Hz), 4.49 (1 H, br. s), 6.57 (2 H, m), 6.75 (2 H, dd, J 8.6 Hz and J 1.8 Hz), 7.02 (1 H, t, J 7.7 Hz), 7.66 (2 H, d, J 8.4 Hz), 7.78 (2 H, dd, J 14.8 Hz and J 8.4 Hz), 8.22 (1 H, q, J 11.6 Hz and J 5.6 Hz), 9.2 (1 H, s) and 9.94 (1 H, d, J 9.2 Hz).

Compound 159

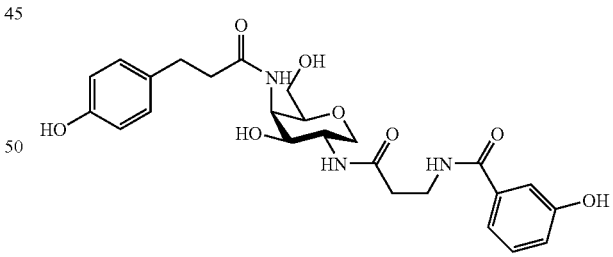

$\delta_H$ (400 MHz; CDCl₃) 2.30-2.90 (6 H expected), 3.05-3.46 (7 H expected), 3.59 (2 H, m), 3.80 (2 H, m), 3.93 (1 H, m), 4.21 (1 H, dd, J 8.8 Hz and J 4.4 Hz), 4.49 (1 H, t, J 6.0 Hz), 4.77 (1 H, d, J 4.8 Hz), 6.64 (1 H, dd, J 6.4 Hz and J 2.0 Hz), 6.87 (1 H, m), 6.98 (2 H, dd, J 8.6 Hz and J 2.6 Hz), 7.20 (2 H, dt, J 5.4 Hz and J 2.2 Hz), 7.74 (1 H, dd, J 20.4 Hz and J 9.2 Hz), 8.34 (1 H, t, J 5.6 Hz), 9.11 (1 H, d, J 11.6 Hz) and 9.60 (1 H, br. s).

EXAMPLE 3
Synthesis of a 1,5-anhydro-2-azido-3-O-benzoyl-6-O-(t-butyldiphenylsilyl)-2-deoxy-D-glucitol
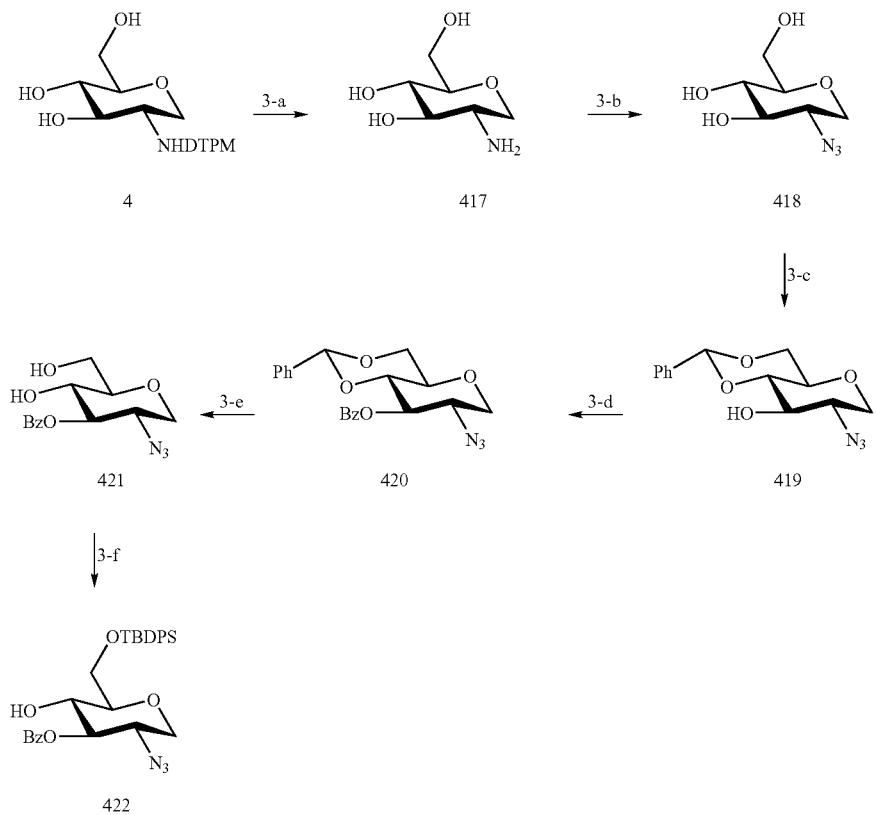
3-a. General Method 8; 3-b. General Method 17; 3-c. General Method 4; 3-d. General Method 5; 3-e. General method 18; 3-f. General Method 19.
EXAMPLE 4
Synthesis of a 1,5-anhydro-2-azido-3-O-benzoyl-6-O-(t-butyldiphenylsilyl)-2-deoxy-D-glucitol
-continued
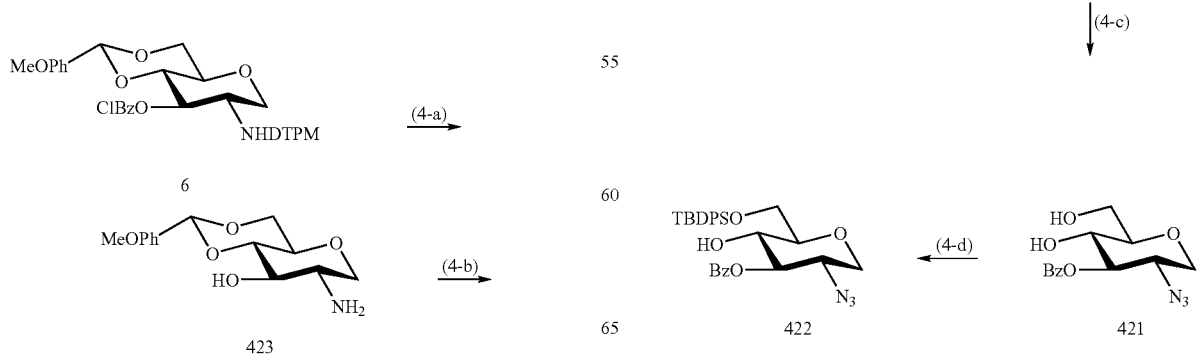

4-a. O— and N-Deprotection of Glucitol Building Block 6 to Form Glucitol 423

Compound 423 was synthesised according to General Method 16, 87.2% yield (0.837 g). [M+H]$^+$=282.30; 98% Purity by ELSD.

4-b. Formation of 2-Deoxy-2-Azido Glucitol Building Block 5 from Building Block 423

The formation of building block 5 was carried out according to the procedure described in General Method 17; [M+H]$^+$=308.1; 98% purity by ELSD. R$_t$=4.62 mins (Agilent SB Zorbax C18 4.6×50 mm (5 pm, 80 Å), LC Mobile Phase: Acetonitrile: Water 0.1% formic acid). Gradient as follows:

| Time (min) | water % | CH$_3$CN % | Flow ml/min |
|---|---|---|---|
| 0.00 | 90.0 | 10.0 | 1.500 |
| 1.00 | 90.0 | 10.0 | 1.500 |
| 7.00 | 0.0 | 100.0 | 1.500 |
| 12.00 | 0.0 | 100.0 | 1.500 |
| 20.00 | 0.0 | 100.0 | 1.500 |

4-c. Preparation of Building Block 421 from Building Block 5 in Three Steps

Compound 421 was subjected to conditions as described in General Method 18. Then the product of this reaction was directly subjected to the conditions as described in General Method 3. Finally the material was subjected to the conditions as described in General Method 19 to provide 5 as a white solid in 69% yield after purification; [M+H]$^+$=294.6. Rt=3.52 mins, (Agilent SB Zorbax C18 4.6×50 mm (5 μm, 80 Å) LC Mobile Phase: Acetonitrile: Water 0.1% formic acid) Gradient as follows;

| Time(min) | water % | CH$_3$CN % | Flow ml/min |
|---|---|---|---|
| 0.00 | 90.0 | 10.0 | 2.00 |
| 1.00 | 90.0 | 10.0 | 2.00 |
| 7.00 | 0.0 | 100.0 | 2.00 |
| 12.00 | 0.0 | 100.0 | 2.00 |
| 13.00 | 90.0 | 10.0 | 2.00 |
| 15.00 | 90.0 | 10.0 | 2.00 |

4-d. Silyl Protection of Building Block 421 to Form Building Block 422

Compound 422 was formed according to the procedure described in General Method 19 in 87% yield, [M+H]$^+$=532.3; 100% purity by ELSD Rt=6.84 mins, (Agilent SB Zorbax C18 4.6×50 mm (5 μm, 80 Å) LC Mobile Phase: Acetonitrile: Water 0.1% formic acid) Gradient as follows:

| Time(min) | water % | CH$_3$CN % | Flow ml/min |
|---|---|---|---|
| 0.00 | 90.0 | 10.0 | 2.00 |
| 1.00 | 90.0 | 10.0 | 2.00 |
| 7.00 | 0.0 | 100.0 | 2.00 |
| 14.00 | 0.0 | 100.0 | 2.00 |
| 15.00 | 90.0 | 10.0 | 2.00 |

Spectral analysis for compound 422; $^1$H-NMR (CDC3, 400 MHz): 0.99 (s, 9 H), 2.99 (d, J=3.76 Hz, 1 H), 3.21 (t, J=11.1, 11.5 Hz, 1 H), 3.31 -3.34 (m, 1 H), 3.65-3.72 (m, 1 H), 3.75-3.82 (m, 1 H), 3.82 - 3.89 (m, 2 H), 4.02 (dd, J=5.4, 11.5 Hz, 1 H), 5.11 (t, J=9.2, 9.7 Hz, 1 H), 7.28-7.43 (m, 8 H), 7.51-7.55 (m, 1 H), 7.58-7.56 (m, 2 H), 8.02-8.06 (m, 2 H).

EXAMPLE 5

General Synthetic Route for Preparation of a Library of Glucitol Peptide Mimetics

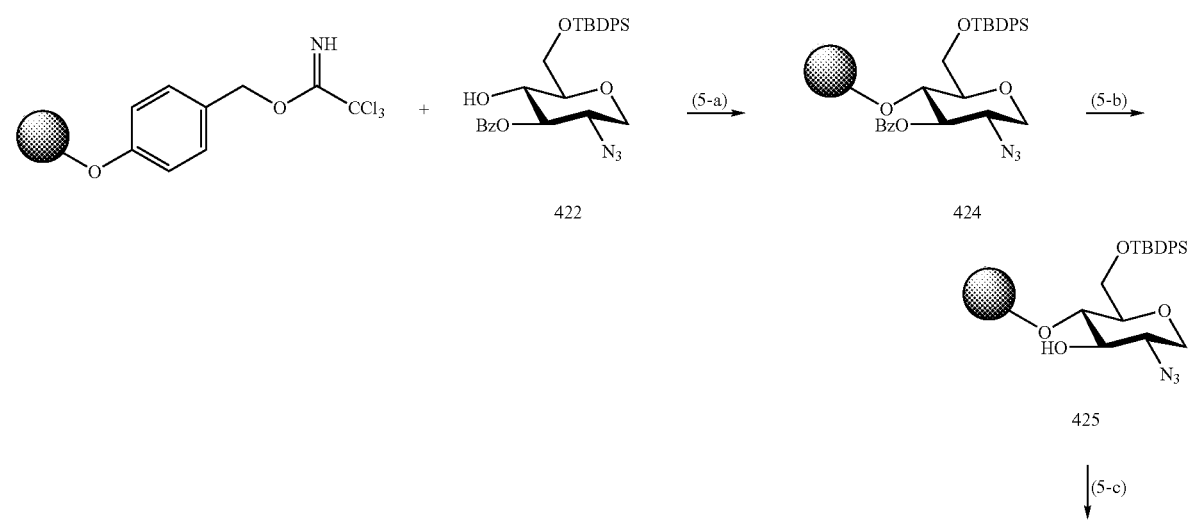

-continued

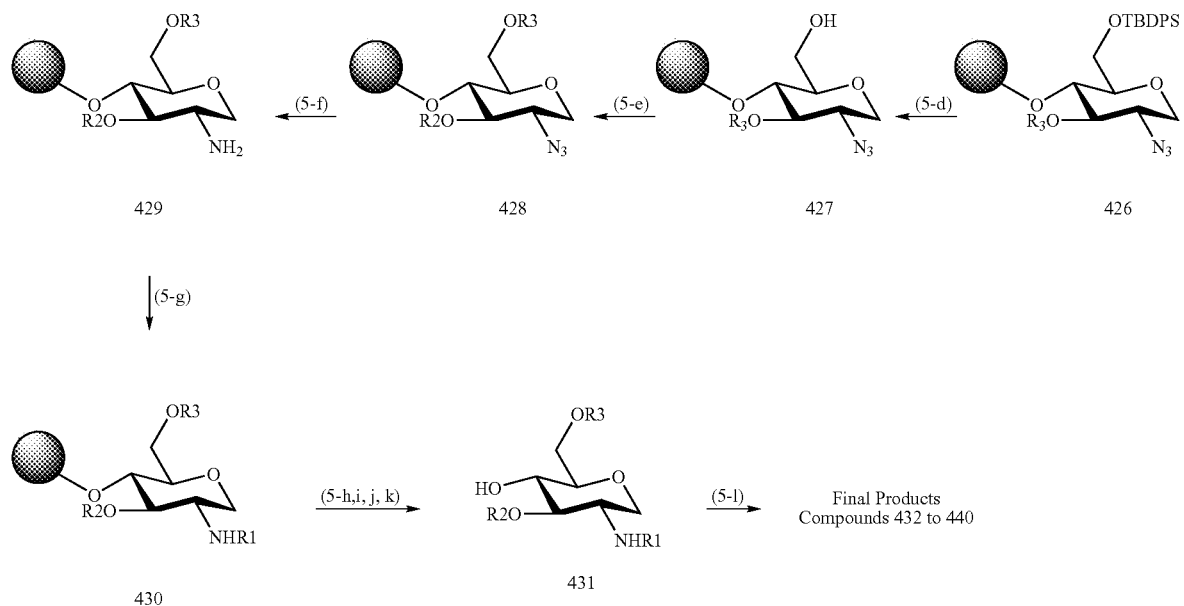

5-a. Coupling of Glucitol Building Block 422 to the Trichloroacetimidate Derivatised Wang Resin to Provide 424

Building Block-Resin Conjugate was prepared according to the procedure outlined in General Method 20.

5-b. Removal of the Benzoyl Group to Form 425

Compounds represented by no. 424 were prepared according to General Method 21.

5-c. Alkylation at Position 3 of Conjugate 425 to Provide Resin-Building Block 426

The compounds represented by no. 425 were subjected to the conditions as described in General Method 22 to provide compounds no. 426.

5-d. Removal of TBDPS Group

The resins designated by 426 were subjected to the conditions as described in General Method 23.

5-e. Alkylation at Position 6 to Provide

The resin bound compounds designated by 427 were alkylated in groups as described for General Method 22.

5-f. Reduction of Azido Group to Provide

The resin bound compounds designated by 428 were subjected to the conditions as described in General Method 24.

5-g. N-Acylations

The resins designated by 429 were either subjected to the conditions as described in General Method 25: Method 1, or, were subjected to the conditions as described in General Method 22: Method 2.

5-h. Reduction of the Nitro Group

If required, the substituent nitro group of a side-aim was reduced to the amine according to the procedure described in General Method 26.

5-i. Deprotection of the Fmoc Protecting Group

If required, the Fmoc protecting group on side-arms was deprotected according to the procedure described in General Method 27.

5-i. Guanylation of Amino Group

If required, amino group substituents of side-arms were guanylated according to the procedure described in General Method 28.

5-k. Cleavage of Final Products from the Resins

The final products were cleaved from resin according to the procedure described in General Methods 29. Final compounds were purified by HPLC-MS (See Table 4).

5-l. Hydrolysis of Me Ester

If required, the cleavage mixtures designated by 431 were individually treated with a solution of LIOH (0.5 molar) in MeOH/water (1/1) (ph~14) for a week. The solvents were removed in vacuo and the residue was purified by HPLC.

TABLE 4

Library of Glucitol compounds

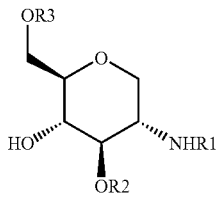

| Comp. No. | R1 | R2 | R3 | M + H | Purity[1] (%) | Rt | Yield mg | Yield[2] % |
|---|---|---|---|---|---|---|---|---|
| 432 | R1a | R2a | R3a | 509.1 | 85.8 ELSD | 3.71 | 14.1 | 53.9 |
| 433 | R1c | R2b | R3b | 507.2 | 63.6 UV | 3.38 | 4.9 | 18.7 |
| 434 | R1d | R2b | R3c | 555.2 | 77.9 UV | 4.04 | | 14.1 |
| 435 | R1d | R2b | R3d | 541.1 | | 3.62 | 8.6 | 30.9 |
| 436 | R1a | R2c | R3a | 369.1 | 73.2 ELSD | 0.86 | 9.6 | 50.5 |
| 437 | R1b | R2c | R3c | 453.2 | 80-UV | 3.18 | | |
| 438 | R1b | R2c | R3d | 439.1 | | 2.52 | 1.6 | 7.1 |
| 439 | R1e | R3b | R3a | 487.1 | 63.8-UV | 2.55 | 12.9 | 51.6 |
| 440 | R1f | R3b | R3a | 446.1 | 65-UV | 2.39 | 3.6 | 15.7 |

[1]UV implies purity by Ulta-Violet detection, ELSD implies purity by Electron Light Scattering Detection.
[2]Yield calculated for the whole solid phase sequence; 140 mg of resin was used for preparation of each compound; the substitution was 0.368 mmol/g, thus the amount of the starting material was 0.0515 mmol.

Side Chains for Table 4:

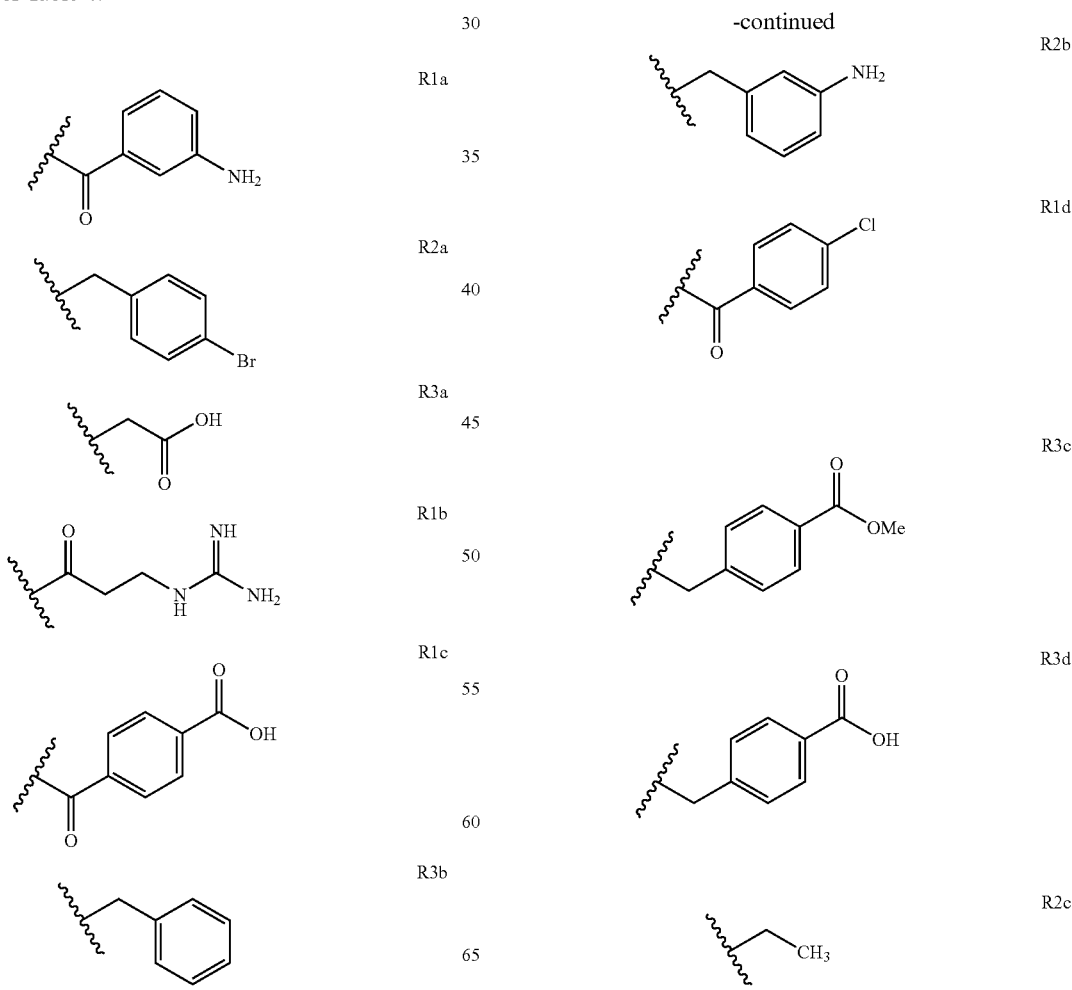

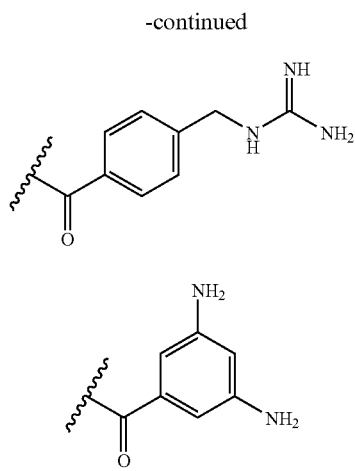

HPLC Method for Compounds in Table 4:

(Agilent SB Zorbax C18 4.6×50 mm (5 μm, 80 Å) LC Mobile Phase:

Acetonitrile: Water 0.1% formic acid) Gradient as follows:

| Time(min) | water % | CH3CN % | Flow ml/min |
|---|---|---|---|
| 0.00 | 95.0 | 5.0 | 2.00 |
| 1.00 | 95.0 | 5.0 | 2.00 |
| 7.00 | 0.0 | 100.0 | 2.00 |
| 12.00 | 0.0 | 100.0 | 2.00 |
| 13.00 | 95.0 | 5.0 | 2.00 |
| 15.00 | 95.0 | 5.0 | 2.00 |

EXAMPLE 7

Allitol Building Block Synthesis

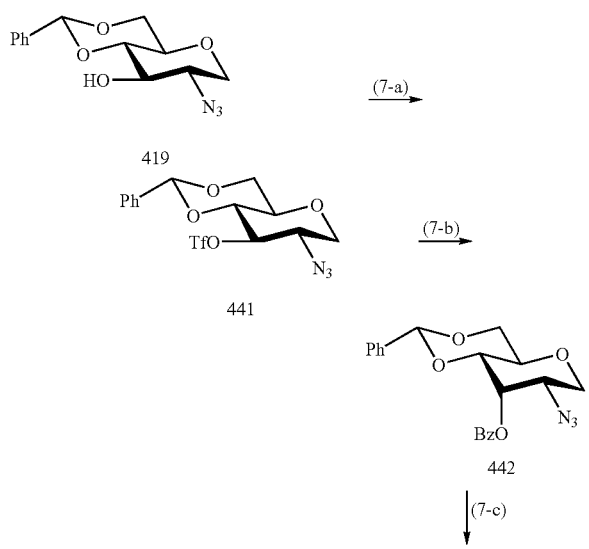

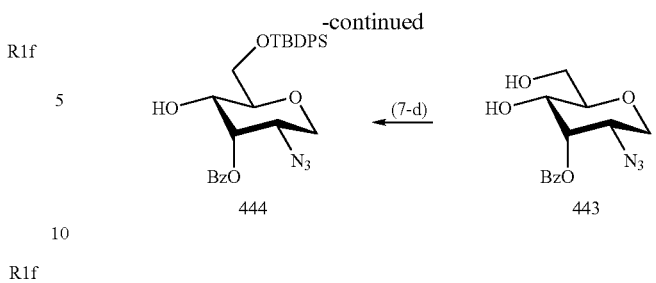

7-a. Synthesis of a 3-O-Triflate Glucitol 441

Compound 419 (300 mg, 1.08 mmol) and symmetric collidine (0.22 mL, 1.65 mmol) were dissolved in anhydrous DCM (7.0 mL) and the solution then cooled to −25° C. A solution of trifluoromethanesulphonic anhydride (0.27 ml, 1.65 mmol) in DCM (2.77 ml) was injected into the solution and the reaction allowed to proceed overnight. The Solution was reduced to dryness, the residue dissolved in DCM (15 ml) and then washed with 0.5 molar HCl. The organic phase was dried over MgSO$_4$, filtered and the solvent removed in vacuo to provide the product 441 (399 mg, 90.3%).

7b. Inversion at the C-3 Position of a Glucitol Block to Form Allitol Block 442

To a solution of compound 441 (4.089 mmol) in DMF (7 mL) was added a solution of LiOBz (1.794 mmol) in DMF (7 mL). The reaction was allowed to proceed at room temperature overnight. The solvent was removed in vacuo and the resulting residue redissolved in EtOAc. The solution was then washed with H$_2$O, the organic layer was collected, dried over MgSO$_4$, filtered and the solvent removed in vacuo to provide allitol block 442 (74.1% yield).

7c. Cleavage of the Benzylidene Ring System to Provide Allitol Block 443

Compound 443 was prepared according to the procedure as described in General Method 18.

7d. Formation of the Differentially Protected 1,5-Anhydro Allitol Building Block Compound 444 was prepared according to the procedure as described by General Method 19.

TABLE 5

Analytical Data for Intermediates and Final Compound in the Synthesis of Allitol Building Block 444.

| Comp. | R1 | R2 | R3 | R4 | R5 | Observed. Mass + H |
|---|---|---|---|---|---|---|
| 441 | N3 | H | OTf | Benzylidene | | 410.13 |
| 442 | N3 | OBz | H | Benzylidene | | 352.15 |
| 443 | N3 | OBz | H | H | H | 294.12 |
| 444 | N3 | OBz | H | H | TBDPS | 532.15 |

EXAMPLE 8

Prototype Library using H-Allose Building Block

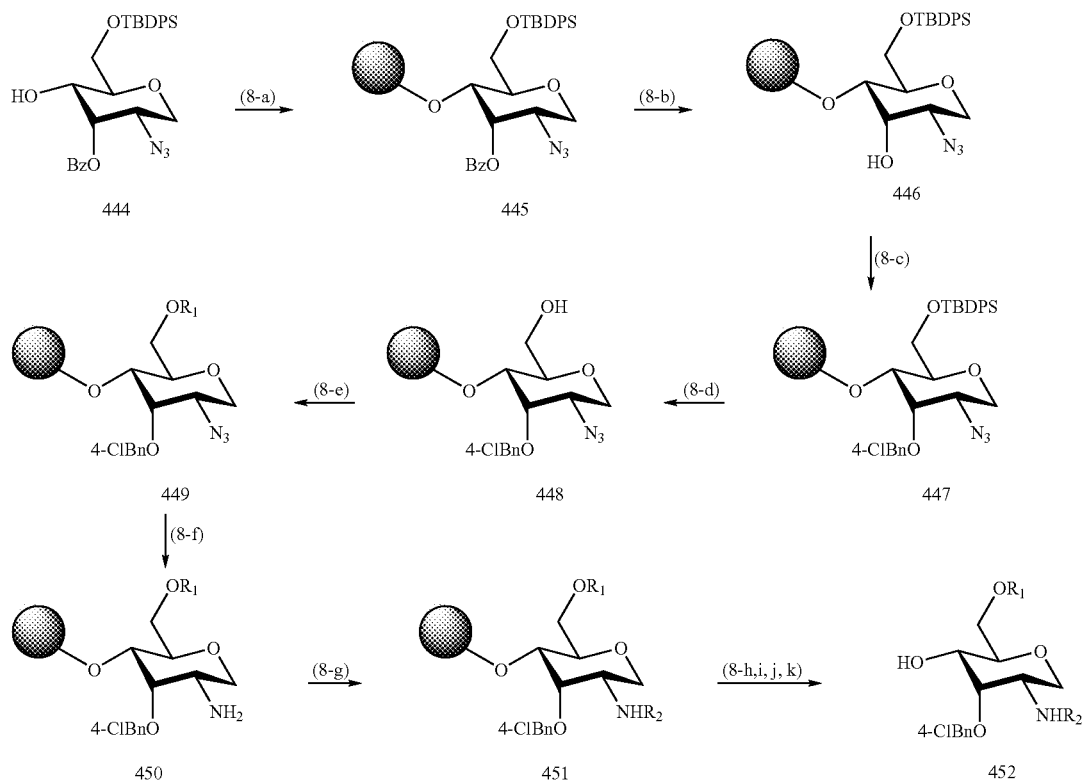

8-a. Coupling of Allitol Building Block 444 to the Trichloroacetimidate Derivatised Wang Resin to Provide 445

Building Block-Resin Conjugate was prepared according to the procedure outlined in General Method 20.

8-b. Removal of the Benzoyl Group to Form 446

Compound 446 was prepared from precursor 445 according to General Method 21.

8-c. Alkylation at Position 3 of Conjugate 446 to Provide Resin-Building Block 447

The compound represented by 446 were subjected to the conditions as described in General Method 22 to provide compounds no. 447.

8-d. Removal of TBDPS Group

The resins designated by 447 were subjected to the conditions as described in General Method 23.

8-e. Alkylation at Position 6

The resin bound compounds designated by 448 were alkylated in groups as described for General Method 22.

8-f. Reduction of Azido Group

The resin bound compounds designated by 449 were subjected to the conditions as described in General Method 24.

8-g. N-Acylations

The resins designated by 450 were either subjected to the conditions as described in General Method 25: Method 1, or, were subjected to the conditions as described in General Method 25: Method 2.

8-h. Reduction of the Nitro Group

If required, the substituent nitro group of a side-arm was reduced to the amine according to the procedure described in General Method 26.

8-i. Deprotection of the Fmoc Protecting Group

If required, the Fmoc protecting group on side-arms was deprotected according to the procedure described in General Method 27.

8-j. Guanylation of Amino Group

If required, amino group substituents of side-arms were guanylated according to the procedure described in General Method 28.

8-k. Cleavage of Final Products from the Resins (14-Final Product)

The final products were cleaved from resin according to the procedure described in General Methods 29 to provide compounds designated by no. 452. Final compounds were purified by HPLC-MS.

TABLE 6

Structural and Analytical Data for Allitol Based Building Block Intermediates and Final Products

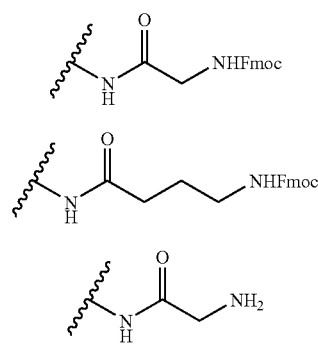

| Compound | R1 | R2 | R3 | R4 | Exp. Mol M + H |
|---|---|---|---|---|---|
| 453 | N3 | Bz | H | TBDPS | 532.27 |
| 454 | N3 | H | H | TBDPS | 428.20 |
| 455 | N3 | p-Clbenzyl | H | TBDPS | 552.25 |
| 456 | N3 | p-Clbenzyl | H | H | 314.1 |
| 457 | N3 | p-Clbenzyl | H | p-ClBenzyl | No Data |
| 458 | N3 | p-Clbenzyl | H | 2-Napthyl | 454.27 |
| 459 | NH2 | p-Clbenzyl | H | p-ClBn | 412.20 |
| 460 | NH2 | p-Clbenzyl | H | 2-Napthyl | 428.20 |
| 461 | R1a | p-Clbenzyl | H | p-ClBn | 691.40 |
| 462 | R1a | p-Clbenzyl | H | 2-Napthyl | 707.40 |
| 463 | R1a | p-Clbenzyl | H | 4-MeBiphenyl | 733.42 |
| 464 | R1b | p-Clbenzyl | H | p-ClBn | 719.40 |
| 465 | R1b | p-Clbenzyl | H | 2-Napthyl | 735.50 |
| 466 | R1b | p-Clbenzyl | H | 4-MeBiphenyl | 747.44 |
| 452a | R1c | p-Clbenzyl | H | p-ClBn | 469.26 |
| 452b | R1c | p-Clbenzyl | H | 2-Napthyl | 485.32 |
| 452c | R1d | p-Clbenzyl | H | p-ClBn | 497.26 |
| 452d | R1d | p-Clbenzyl | H | 2-Napthyl | 513.37 |
| 452f | R1e | p-Clbenzyl | H | p-ClBn | 511.28 |
| 452g | R1e | p-Clbenzyl | H | 2-Napthyl | 527.33 |
| 452h | R1f | p-Clbenzyl | H | p-ClBn | 539.31 |
| 452l | R1f | p-Clbenzyl | H | 2-Napthyl | 555.38 |
| 452j | R1g | p-Clbenzyl | H | 4-Mebiphenyl | 525.30 |
| 452k | R1c | p-Clbenzyl | H | 4-Mebiphenyl | 511.20 |

Sidearms for Table 6

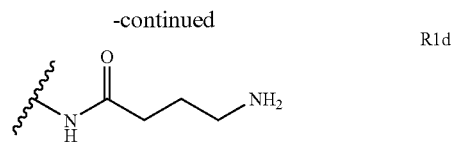
R1a

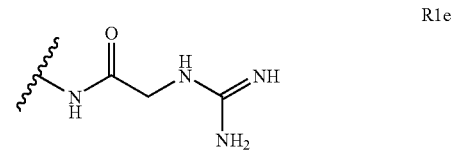
R1b

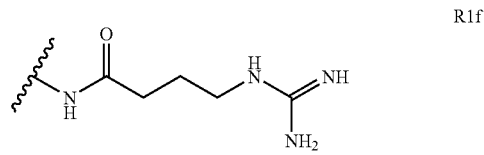
R1c

-continued

R1d

R1e

R1f

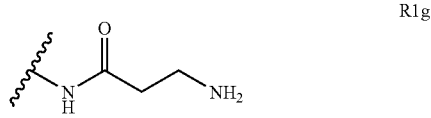
R1g

EXAMPLE 9

Synthesis of a 1,5-anhydro-3-azido-6-O-(t-butyldimethylsilyl)-2,3-dideoxy-2-[(1,3-dimethyl-2,4,6-(1H, 3H,5H)-troxopyrmidin-5-ylidene)methylamino]-D-allitol

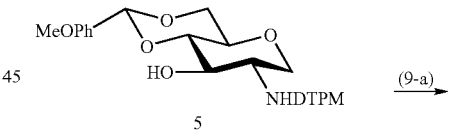

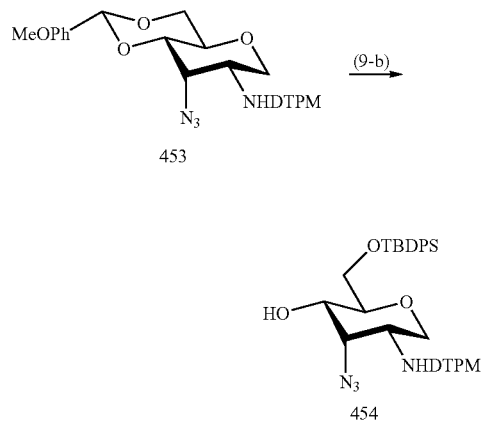

9-a. Formation of a Aminoallitol Building Block from a Glucitol Precursor

Compound 5 was reacted according to the procedure described in General Method 6.

9-b. Formation of a Silyl Protected Building Block

Compound 453 was reacted according to the procedure described in General Method 18. The product of this reaction was reacted according to the procedure described in General Method 19 to provide compound 454.

EXAMPLE 10

Synthesis of a 1,5-anhydro-3-azido-4-O-benzoyl-2, 3dideoxy-2-[(1,3-dimethyl-2,4,6-(1H,3H,5H)-trioxopyrimidin-5ylidene)methylaminol]-6-O-(4-methoxybenzyl)-D-gulitol

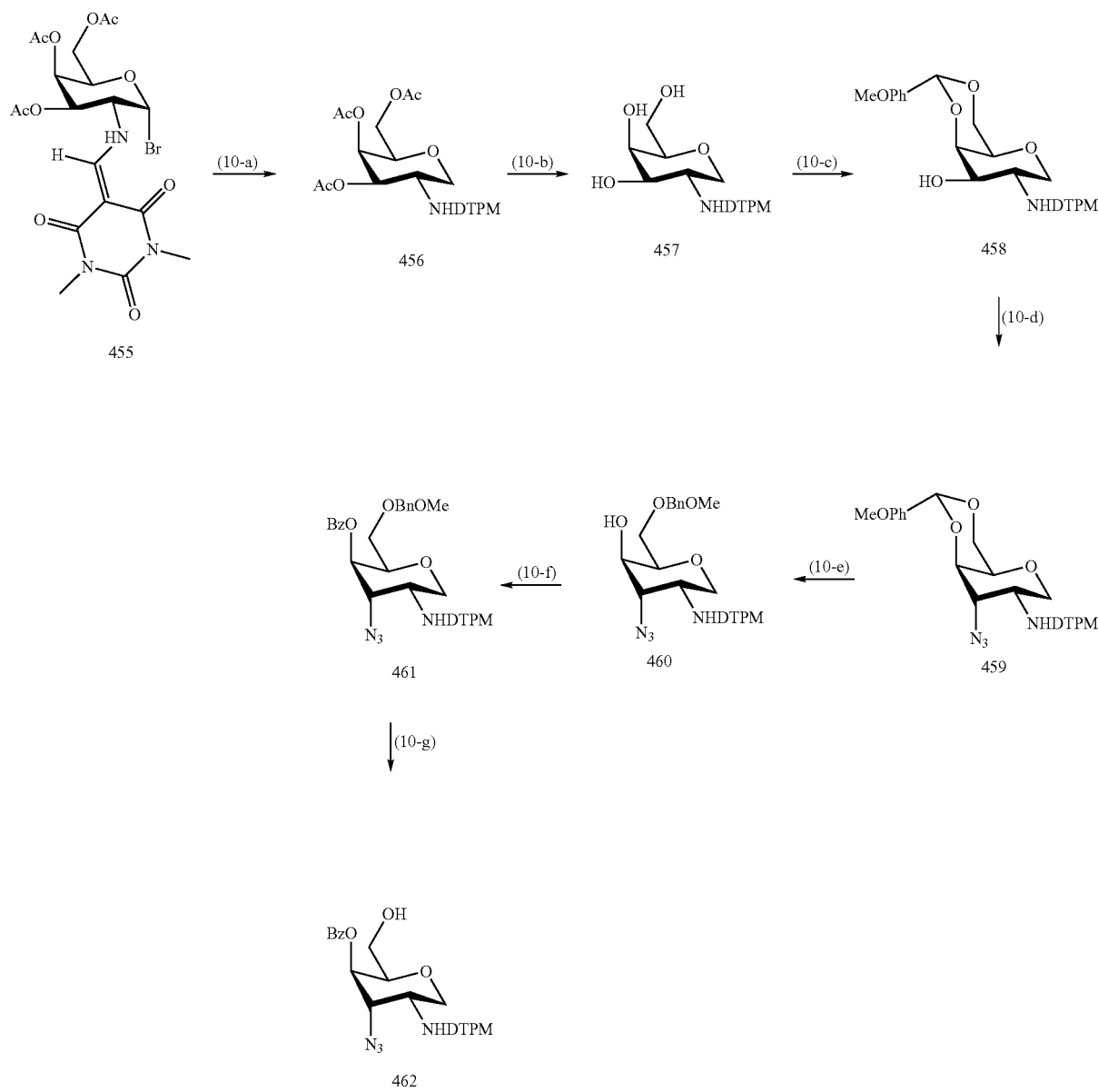

10-a. General Method 2; 10-b. General Method 3; 10-c. General Method 4; 10-d. General Method 6; 10-e. General Method 33; 10-f. General Method 5; 10-g. General Method 14.
EXAMPLE 11
Synthesis of a Library of Compounds by Solid Phase Techniques Using a Galactitol Building Block
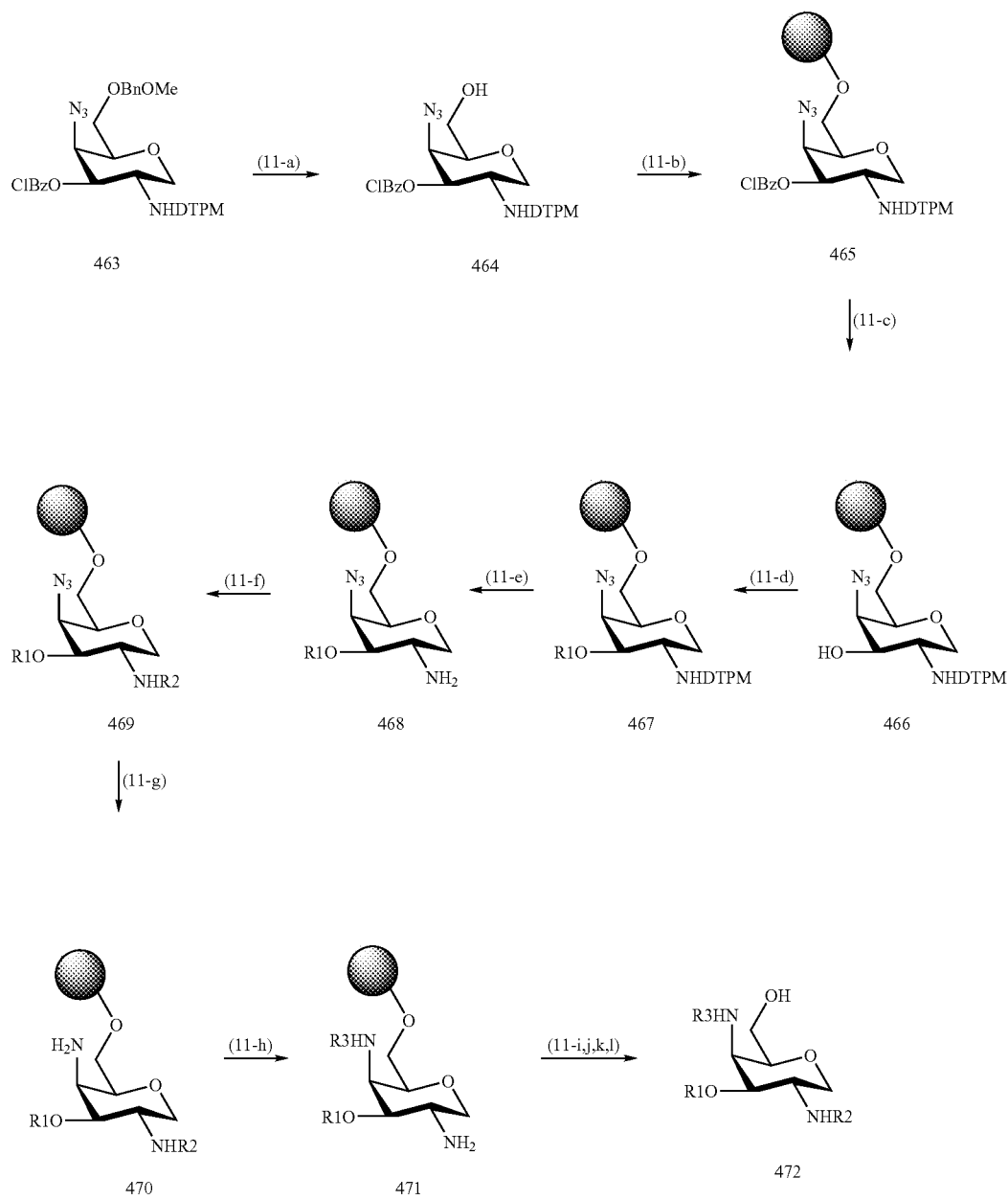

11-a. General Method 14; 11-b. General Method 20; 11-c. General Method 21; 11-d. General Method 22; 11-e. General Method 32; 11-f. General Method 25; 11-g. General Method 24; 11-h. General Method 25; 11-i to l selected from General Methods 26-29 (as appropriate).

EXAMPLE 12

Solid Phase Synthesis of a 2,5-Bis Amino-Allitol Library

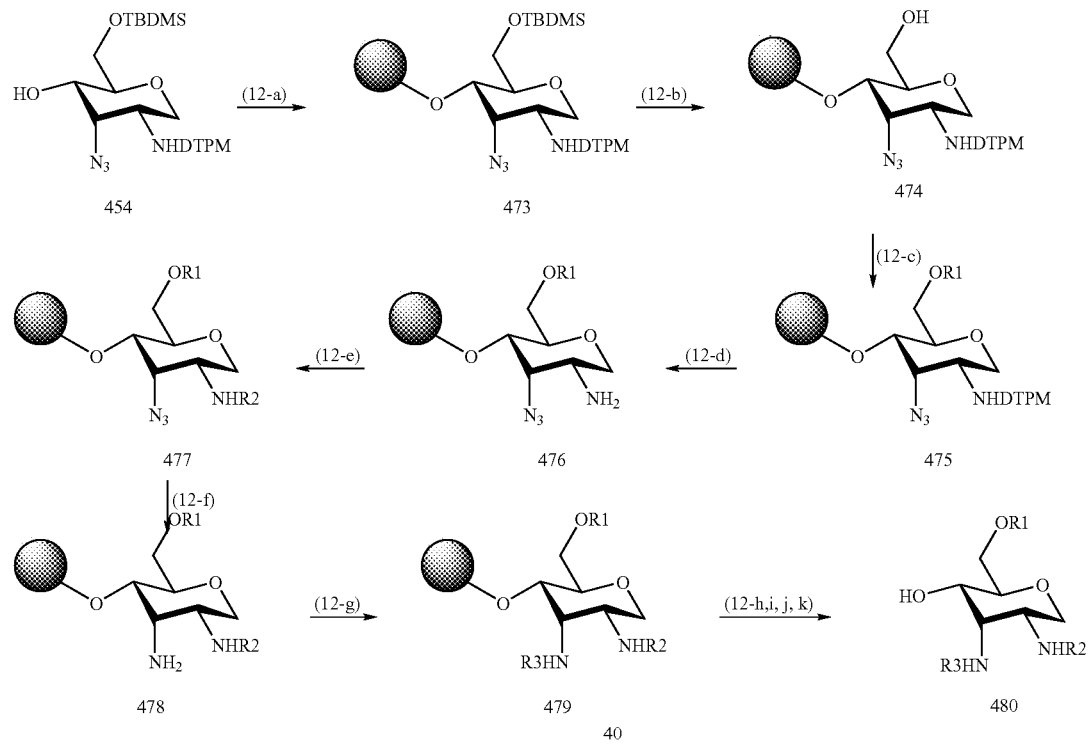

12-a. General Method 20; 12-b. General Method 23; 12-c. General Method 22; 12-d. General Method 32; 12-e. General Method 25; 12-f. General Method 24; 12-g. General Method 25; 12-h to k selected from General Methods 26-29 (as appropriate).

EXAMPLE 13

Synthesis of a Library of Compound by Solid Phase Techniques Using a Diamino Gulitol Based Building Block

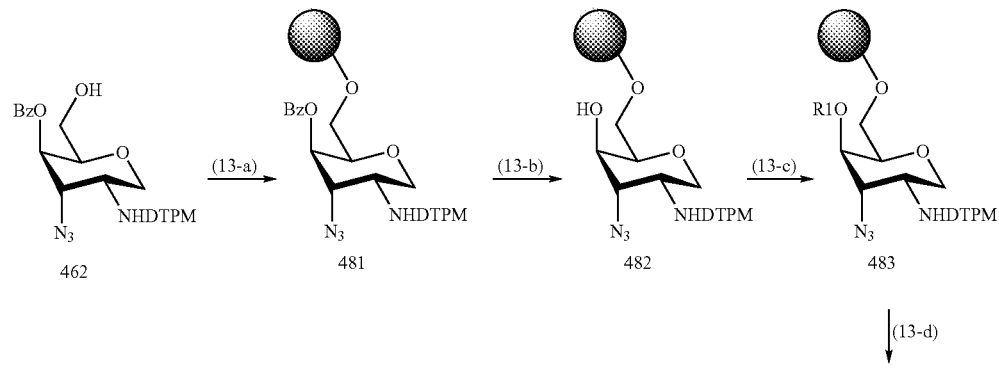

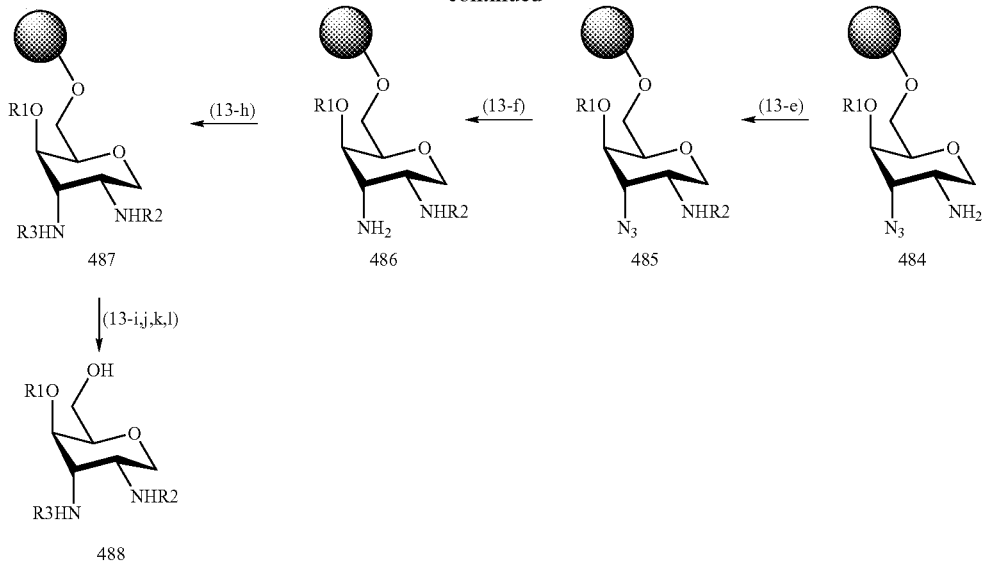

13-a. General Method 20; 13-b. General Method 21; 13-c. General Method 22; 13-d. General Method 31; 13-e. General Method 25; 13-f. General Method 24; 13-g. General Method 25; 13-h to k selected from General Methods 26-29 (as appropriate).

EXAMPLE 14

Synthesis of an Exemplary Library 1

PART 1: In this example three different mimetics of three different peptide residues (ie. Phe mimetic 1, 2 and 3, Lys mimetic 1, 2 and 3, and Trp mimetic 1, 2 and 3§) maintain their position on the scaffold (Phe=$R^1$, Lys=$R^2$, Trp=$R^3$), but the different mimetics are varied in relation to one another.

PART 2: further in this example, three different mimetics of three different peptide residues (ie. Phe mimetic 1, 2 and 3, Lys mimetic 1, 2 and 3, and Trp mimetic 1, 2 and 3§) are varied in their substitution point around the scaffold, ie. Phe mimetic 1 moves from $R^1$ to $R^2$ to $R^3$, and so on.

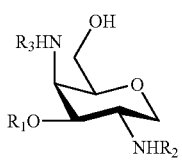

A

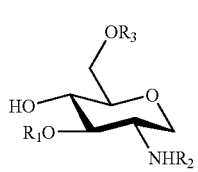

B

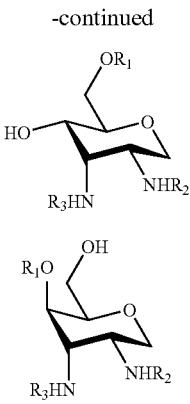

TABLE 8

| R1 | R2 | R3 |
|---|---|---|
| PART 1 | | |
| Phe mimetic 1 | Lys mimetic 1 | Trp mimetic 1 |
| Phe mimetic 2 | Lys mimetic 1 | Trp mimetic 1 |
| Phe mimetic 3 | Lys mimetic 1 | Trp mimetic 1 |
| Phe mimetic 1 | Lys mimetic 1 | Trp mimetic 2 |
| Phe mimetic 2 | Lys mimetic 1 | Trp mimetic 2 |
| Phe mimetic 3 | Lys mimetic 1 | Trp mimetic 2 |
| Phe mimetic 1 | Lys mimetic 1 | Trp mimetic 3 |
| Phe mimetic 2 | Lys mimetic 1 | Trp mimetic 3 |
| Phe mimetic 3 | Lys mimetic 1 | Trp mimetic 3 |
| Phe mimetic 1 | Lys mimetic 2 | Trp mimetic 1 |
| Phe mimetic 2 | Lys mimetic 2 | Trp mimetic 1 |
| Phe mimetic 3 | Lys mimetic 2 | Trp mimetic 1 |
| Phe mimetic 1 | Lys mimetic 2 | Trp mimetic 2 |
| Phe mimetic 2 | Lys mimetic 2 | Trp mimetic 2 |
| Phe mimetic 3 | Lys mimetic 2 | Trp mimetic 2 |
| Phe mimetic 1 | Lys mimetic 2 | Trp mimetic 3 |
| Phe mimetic 2 | Lys mimetic 2 | Trp mimetic 3 |
| Phe mimetic 3 | Lys mimetic 2 | Trp mimetic 3 |
| Phe mimetic 1 | Lys mimetic 3 | Trp mimetic 1 |
| Phe mimetic 2 | Lys mimetic 3 | Trp mimetic 1 |
| Phe mimetic 3 | Lys mimetic 3 | Trp mimetic 1 |

TABLE 8-continued

| R1 | R2 | R3 |
|---|---|---|
| Phe mimetic 1 | Lys mimetic 3 | Trp mimetic 2 |
| Phe mimetic 2 | Lys mimetic 3 | Trp mimetic 2 |
| Phe mimetic 3 | Lys mimetic 3 | Trp mimetic 2 |
| Phe mimetic 1 | Lys mimetic 3 | Trp mimetic 3 |
| Phe mimetic 2 | Lys mimetic 3 | Trp mimetic 3 |
| Phe mimetic 3 | Lys mimetic 3 | Trp mimetic 3 |
| PART 2 | | |
| Lys mimetic 1 | Trp mimetic 1 | Phe mimetic 1 |
| Trp mimetic 1 | Phe mimetic 1 | Lys mimetic 1 |
| Lys mimetic 2 | Trp mimetic 1 | Phe mimetic 1 |
| Trp mimetic 1 | Phe mimetic 1 | Lys mimetic 2 |
| Lys mimetic 3 | Trp mimetic 1 | Phe mimetic 1 |
| Trp mimetic 1 | Phe mimetic 1 | Lys mimetic 3 |
| Lys mimetic 1 | Trp mimetic 2 | Phe mimetic 2 |
| Trp mimetic 2 | Phe mimetic 2 | Lys mimetic 1 |
| Lys mimetic 2 | Trp mimetic 2 | Phe mimetic 2 |
| Trp mimetic 2 | Phe mimetic 2 | Lys mimetic 2 |
| Lys mimetic 3 | Trp mimetic 2 | Phe mimetic 2 |
| Trp mimetic 2 | Phe mimetic 2 | Lys mimetic 3 |

TABLE 8-continued

| R1 | R2 | R3 |
|---|---|---|
| Lys mimetic 1 | Trp mimetic 3 | Phe mimetic 3 |
| Trp mimetic 3 | Phe mimetic 3 | Lys mimetic 1 |
| Lys mimetic 2 | Trp mimetic 3 | Phe mimetic 3 |
| Trp mimetic 3 | Phe mimetic 3 | Lys mimetic 2 |
| Lys mimetic 3 | Trp mimetic 3 | Phe mimetic 3 |
| Trp mimetic 3 | Phe mimetic 3 | Lys mimetic 3 |

§The various scaffold substituents Lys, Phe, and Trp mimetics 1, 2 and 3, are listed in Table 3 below. It is noted that in some case amine protection is required, which is typically effected by Boc protection. It is further noted that in some cases an O-linked mimetic is required and in other cases an N-linked mimetic is required. In the cases of the O-linked Lys mimetics, the mimetic is coupled as either the para, ortho or meta nitrobenzyl derivative and subsequently reduced to the amine.

TABLE 9

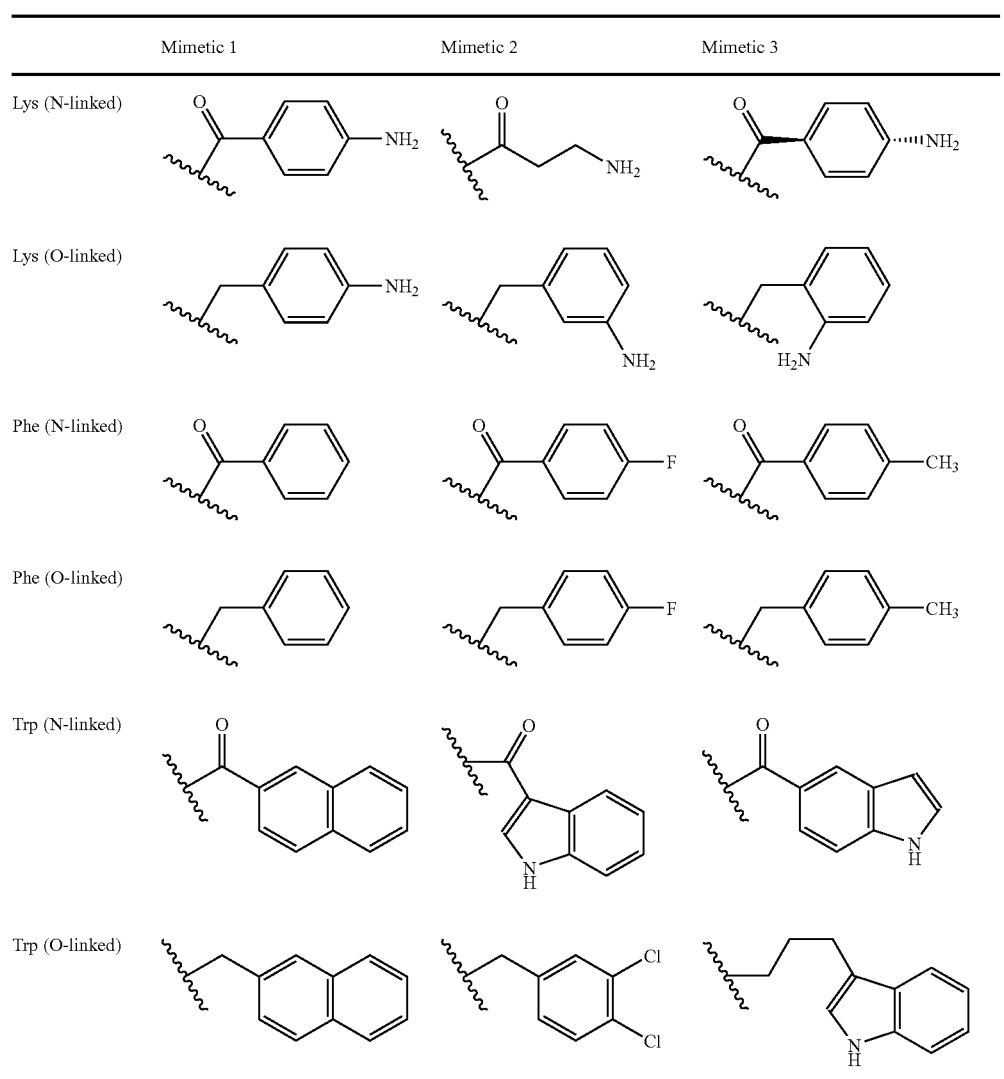

EXAMPLE 15
A Gulitol N-Glycoside Building Block
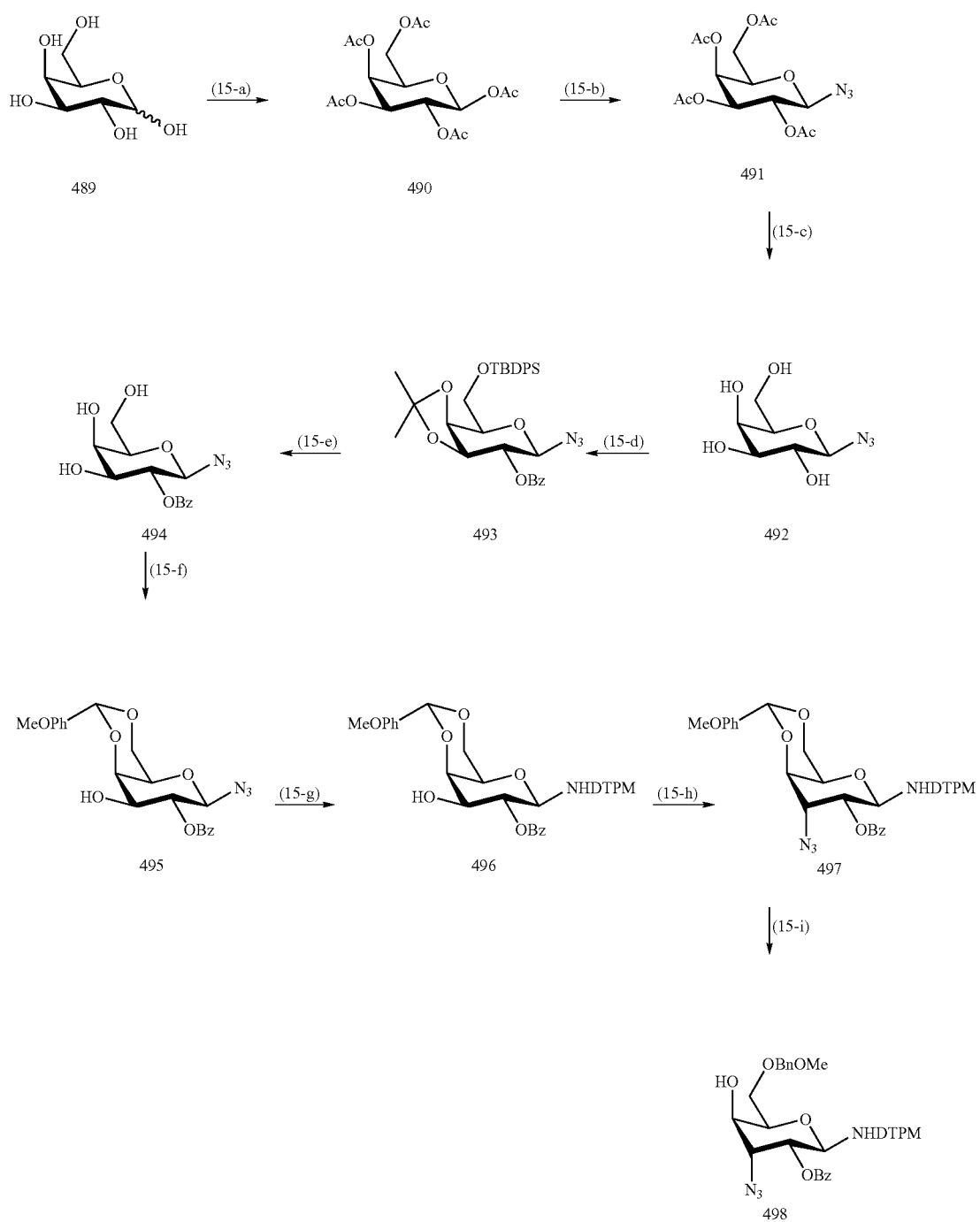

15-a. Ac$_2$O, NaOAc; 15-b. General Method 34; 15-c. General Method 3; 15-d. (a) TBDPS—Cl, 1,2-DCE, imidazole; (b) 2,2-dimethoxy-propane, TsOH, MeCN; 15-e. (a) Benzoylchloride, pyridine, 1,2-DCE, DMAP; (b) MeOH, TsOH, MeCN; 15-f. General Method 4; 15-g. General Methods 13 and 20; General Method 33.

EXAMPLE 16

Synthesis of Glucosyl N-Glycoside Building Block

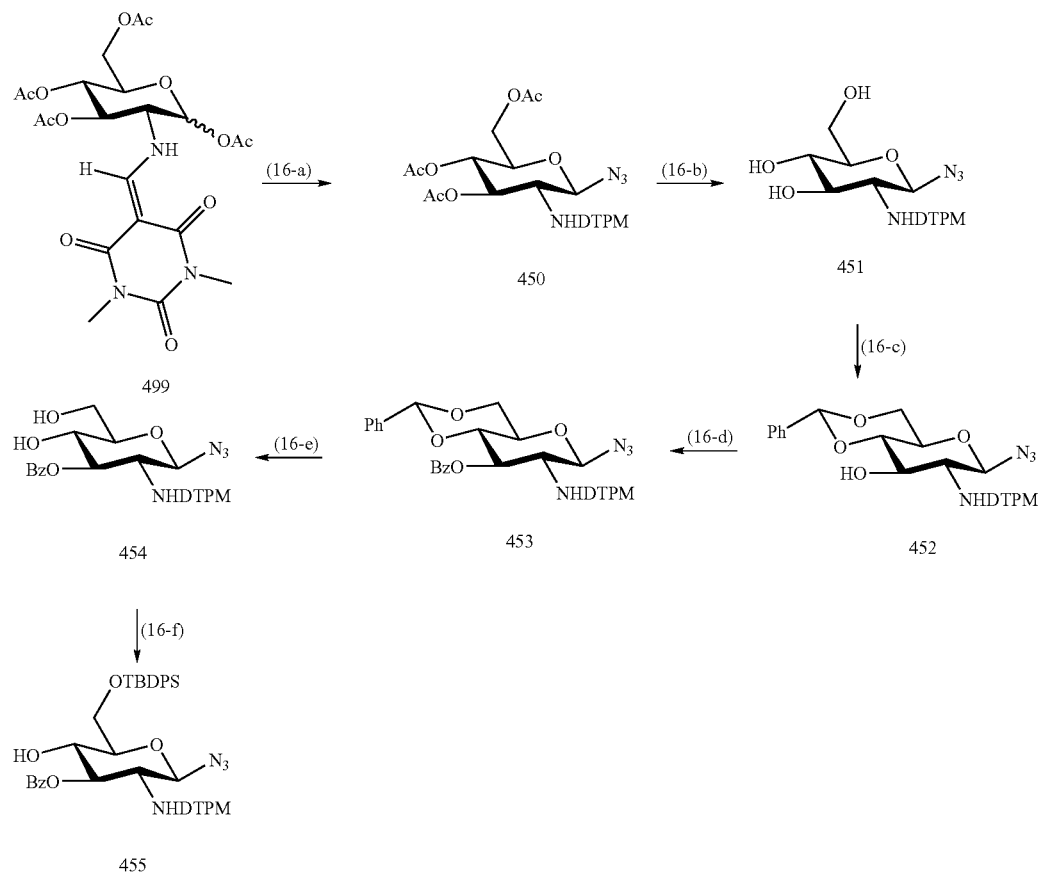

16-a. General Method 34; 16-b. General Method 3; 16-c. General Method 4; 16-d. General Method 5; 16-e. General Method 18; 16-f. General Method 19.

EXAMPLE 17

Synthesis of Glucosylamino 2-Deoxy-2-Amino Library

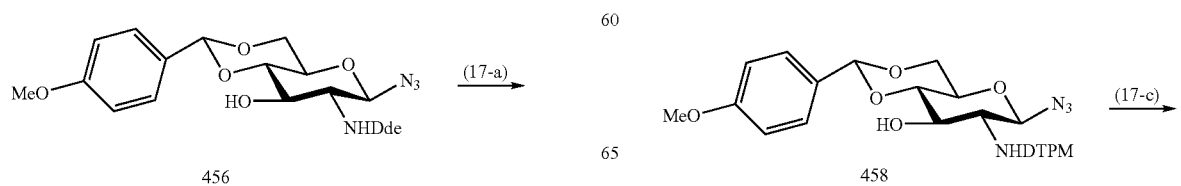

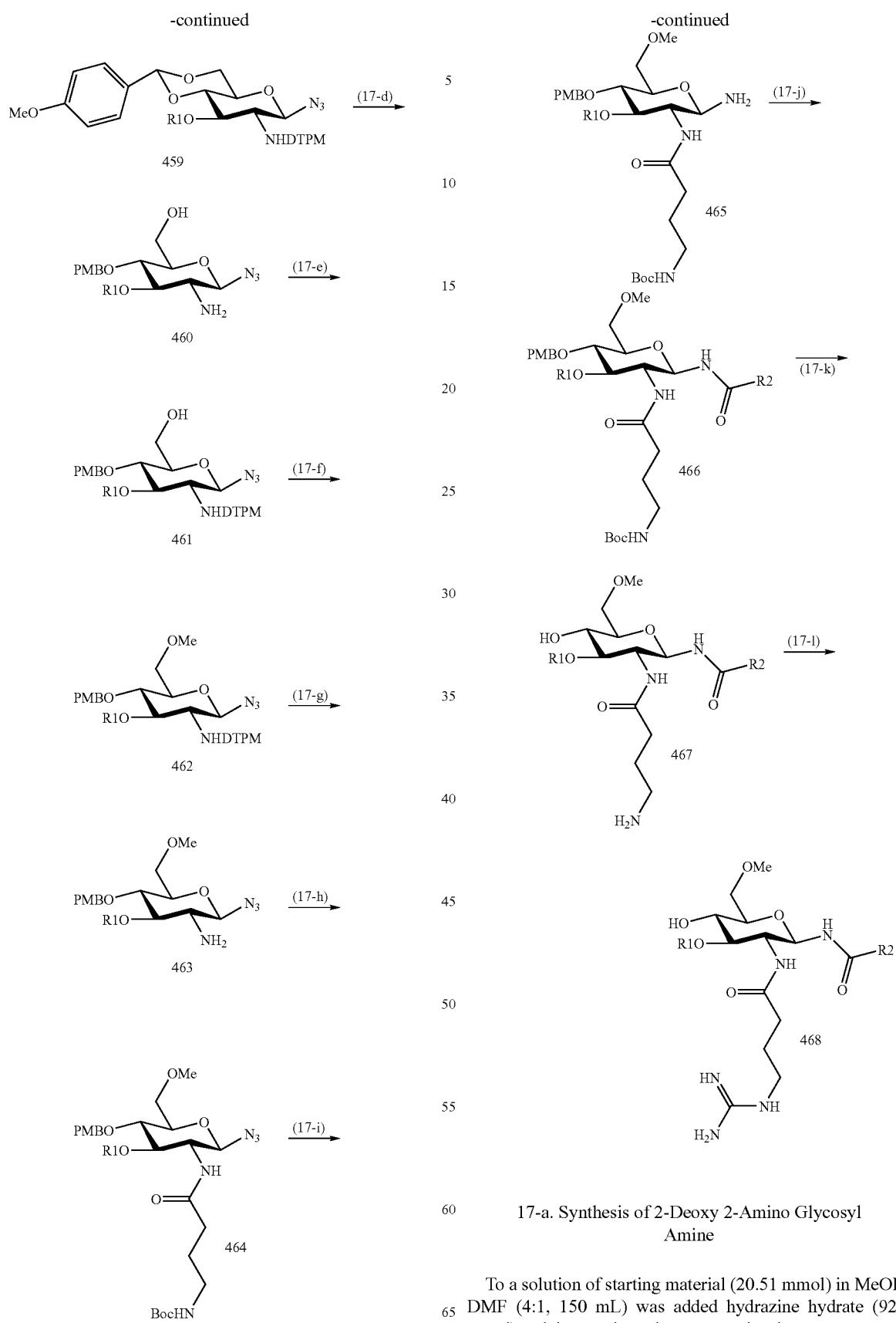
17-a. Synthesis of 2-Deoxy 2-Amino Glycosyl Amine
To a solution of starting material (20.51 mmol) in MeOH/DMF (4:1, 150 mL) was added hydrazine hydrate (92.2 mmol) and the reaction mixture was stirred at room temperature for 1.5 h. The solution was diluted with ~400 mL chloroform, washed with brine, dried over MgSO$_4$, filtered and the solvents evaporated. The crude product 457 was directly used for the next step.

17-b. Synthesis of 2-Deoxy 2-NHDTPM Protected Glycosyl Amine

Compound 458 was formed from reaction of 457 according to the procedure described in General Method 30.

17-c. Synthesis of 2-Deoxy 2-NHDTPM Protected Glycosyl Amine Alkylated in the 3-Position Compounds 459 were formed according to the procedure described in General Method 7.

17-d. Reductive Ring Opening of a 2-Deoxy 2-NHDTPM 3-O-Alkyl Glycosyl Amine

A solution of a derivative represented by 460 (4.37 mmol) in dry DCM (30 mL) was cooled to 0° C. and 44 ml of a 1 molar solution of BH$_3$ in THF (44 mmol) and 0.43 mL of a 1 molar solution of dibutylboron triflate in DCM (0.43 mmol) were added. The reaction mixture was stirred at 0° C. and 0.1 eq. of Bu$_2$BOTf repeatedly added at 1 h intervals until t.l.c. (toluene/EtOAc 1:1) showed complete conversion (total of 0.5 eq. BU$_2$BOTf. The reaction was quenched by the addition of 8 mL Et$_3$N and 15 mL MeOH at 0° C. After evaporation of the solvents the residue was taken up in 350 mL DCM, the solution washed with half saturated brine, filtered over cotton and the solvents evaporated to yield a residue containing the product that was directly used in the next step.

17-e. Re-amino Protection of 3-O-Alkyl Glycosyl Amine

Compounds 461 were formed according to the procedure described in General Method 30; 1H-NMR, (CDCl$_3$): δ 9.92 (dd, 1H, NH, J$_{NH,2}$=9.7 Hz, J$_{NH,=CH}$=13.8 Hz), 7.88 (d, 1H, =CH), 7.75-7.68 (m, 4H, Ar), 735-7.22 (m, 5H, Ar), 6.95-6.86 (m, 2H, Ar), 5.08 (d, 1H, NapCH$_2$, J$_{gem}$=12.1 Hz), 4.86 (d, 1H, PMPCH$_2$, J$_{gem}$=10.5 Hz), 4.72 (d, 1H, PMPCH$_2$), 4.71(d, 1H, H-1b, J$_{1,2}$=9.2 Hz), 4.69 (d, 1H, NapCH$_2$), 3.95 (dd, 1H, H-6a, J$_{gem}$=12.2 Hz, J$_{5,6a}$=1.7 Hz), 3.85-76 (m, 1H, H-6b), 3.81 (s, 3H, OMe), 3.74 (dd, 1H, H-4, J$_{3,4}$=8.9 Hz, J$_{4,5}$=9.4 Hz), 3.64 (dd, 1H, H-3, J$_{2,3}$=9.3 Hz), 3.49 (ddd, 1H, H-5), 3.22 (s, 3H, NMe), 3.11 (dd, 1H, H-2), 3.05 (s, 3H, NMe).

17-f. Methylation of the 6-Position of a Glycosylamine

Compounds 462 were formed according to the procedure described in General Method 7; 1H-NMR (CDCl3); δ 9.92 (dd, 1H, NH, J$_{NH2}$=9.7 Hz, J$_{NH=CH}$=13.8 Hz), 7.88 (d, 1H, =CH), 7.75-7.68 (m, 4H, Ar), 735-7.22 (m, 5H, Ar), 6.95-6.86 (m, 2H, Ar), 5.08 (d, 1H, NapCH$_2$, J$_{gem}$=12.1 Hz), 4.86 (d, 1H, PMPCH$_2$, Jg$_{em}$=10.5 Hz), 4.72-4.68 (m, 3H, NapCH$_2$, PMPCH$_2$, H-1), 3.80-3.74 (m, 3H, H-6a, H-6b, H-4), 3.81 (s, 3H, OMe), 3.64 (dd, 1H, H-3, J$_{2,3}$=9.3 Hz), 3.49 (ddd, 1H, H-5), 3.22 (s, 3H, NMe), 3.11 (dd, 1H, H-2), 3.05 (s, 3H, NMe).

17-g. Removal of the DTPM Group of 2-Deoxy-2-Amino Glycosylamine Compound

Compounds 463 were formed according to the procedure described in General Method 8; 1H-NMR, (CDCl$_3$) δ 7.78-7.66 (m, 4H, Ar), 7.43-7.32 (m, 5H, Ar), 6.86-6.69 (m, 2H, Ar), 5.48 (s, 1H, CH—PMP), 5.05 (d, 1H, NapCH$_2$, J$_{gem}$=11.3 Hz), 4.77 (d, 1H, NapCH$_2$), 4.47 (d, 1H, H-1b, J$_{1,2}$=8.9 Hz), 4.28 (dd, 1H, H-6a, J$_{gem}$=10.3 Hz, J$_{5,6a}$=5.5 Hz), 3.76-3.65 (m, 2H, H-6b, H-4), 3.72 (s, 3H, OMe), 3.49 (dd, 1H, H-3, J$_{2,3}$=9.0 Hz, J$_{3,4}$=9.0 Hz), 3.46 (ddd, 1H, H-5), 2.75 (dd, 1H, H-2).

17-h. Synthesis of a 2-Deoxy-2-N-Acyl Glycosyl Amine

The compounds 464 were synthesised according to the procedure described in General Method 31.

17-i. Solution Phase Reduction of an Anomeric Azide

The compounds 465 were synthesised according to the procedure described in General Method 13.

17-j. Formation of 1-N-Acyl Derivatives of a Glucosaminyl Derivative

The compounds 466 synthesised according to the procedure described in General Method 31.

17-k. Removal of a Boc Protecting Group from a 2-Deoxy-2—N-Acyl-Glycosylamine Derivative Dissolve crude 467 (~0.21mmol) in 10 mL 20% TFA in DCM and stir at room temperature for 10 min. Evaporate solvents and dry the remaining syrup under high vacuum. Redissolve in DCM and wash with 1M KOH, filter over cotton, evaporate and purify by column chromatography (eluent DCM/MeOH 10:1 1% Et$_3$N) to give the product (for the formation of compounds 469, 470, 471). Yield typically 35% over two steps.

17-l. Solution Phase Guanylation (only for the Formation of Compound 472)

To a solution of crude 467 (max. 0.22 mmol) in dry DMF were added 89 mg (0.44 mmol) 3,5-dimethylpyrazole-1-carboxamidine nitrate and 84 µL (0.48 mmol) DIPEA and the reaction mixture stirred for 3 h. The solvents were evaporated and the residue dried under high vacuum to give 280 mg of a mixture containing the desired product. The purification using preparative HPLC gave 8 mg of the pure product 472.

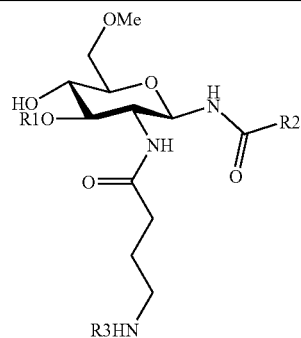
| Comp. | R1 | R2 | R3 | Molecular Ion |
|---|---|---|---|---|
| 469 | naphthyl | phenyl | H | $[M + H]^+ = 522.33$ |
| 470 | naphthyl | 4-Chlorophenyl | H | $[M + H]^+ = 556.1$ |
| 471 | naphthyl | benzyl | H | $[M + H]^+ = 536.36$ |
| 472 | 4-chlorobenzyl | α-naphthyl | C(NH)NH$_2$ | $[M + H]^+ = 598.39$ |
EXAMPLE 18
Synthesis of a Carboxamide C-Glycoside 1
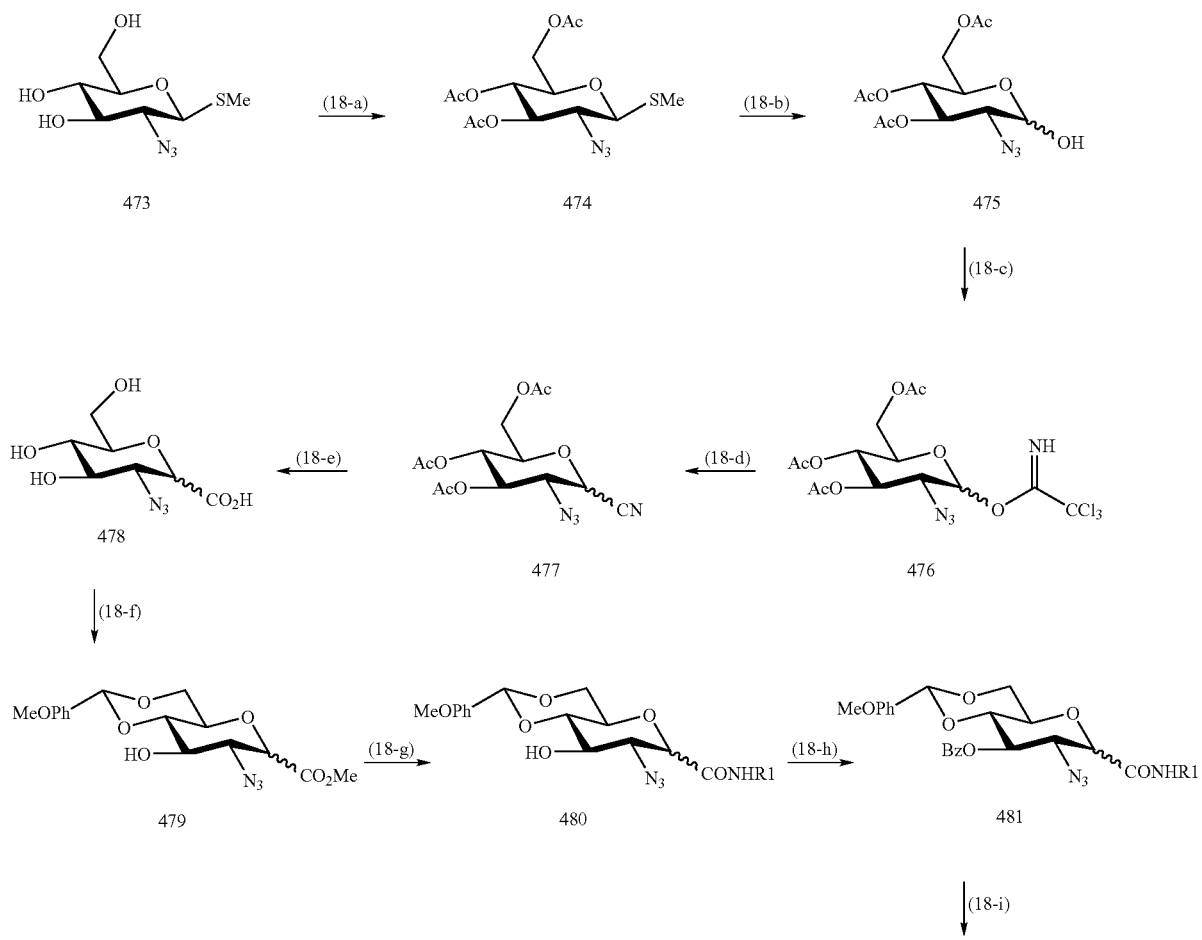

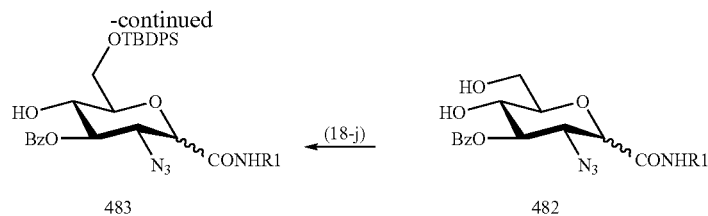
Conditions: NaOMe/MeOH; (ii) Acetone, NBS; (iii) trichloroacetonitrle, potassium carbonate, DCM; (iv) TMS-CN, TMS-Off, DCM; (v) NaOH/H₂O₂; (vi) (a) TMS-CH₂N₂; (b) p-methoxybenzaldehyde dimethylacetal, CSA, MeCn, DMF; (vii) (a) LiOH, H₂O, THF; (b) HBTU, DIPEA, DMF, R¹—NH₂; (viii) benzoylchloride, pyridine, 1,2-DCE, DMAP; (TsOH, MeOH, MeCN, H₂O; (x) TBDPS—Cl, imidazole, 1,2-DCE.
EXAMPLE 19
Synthesis of an Ally C-Glycoside
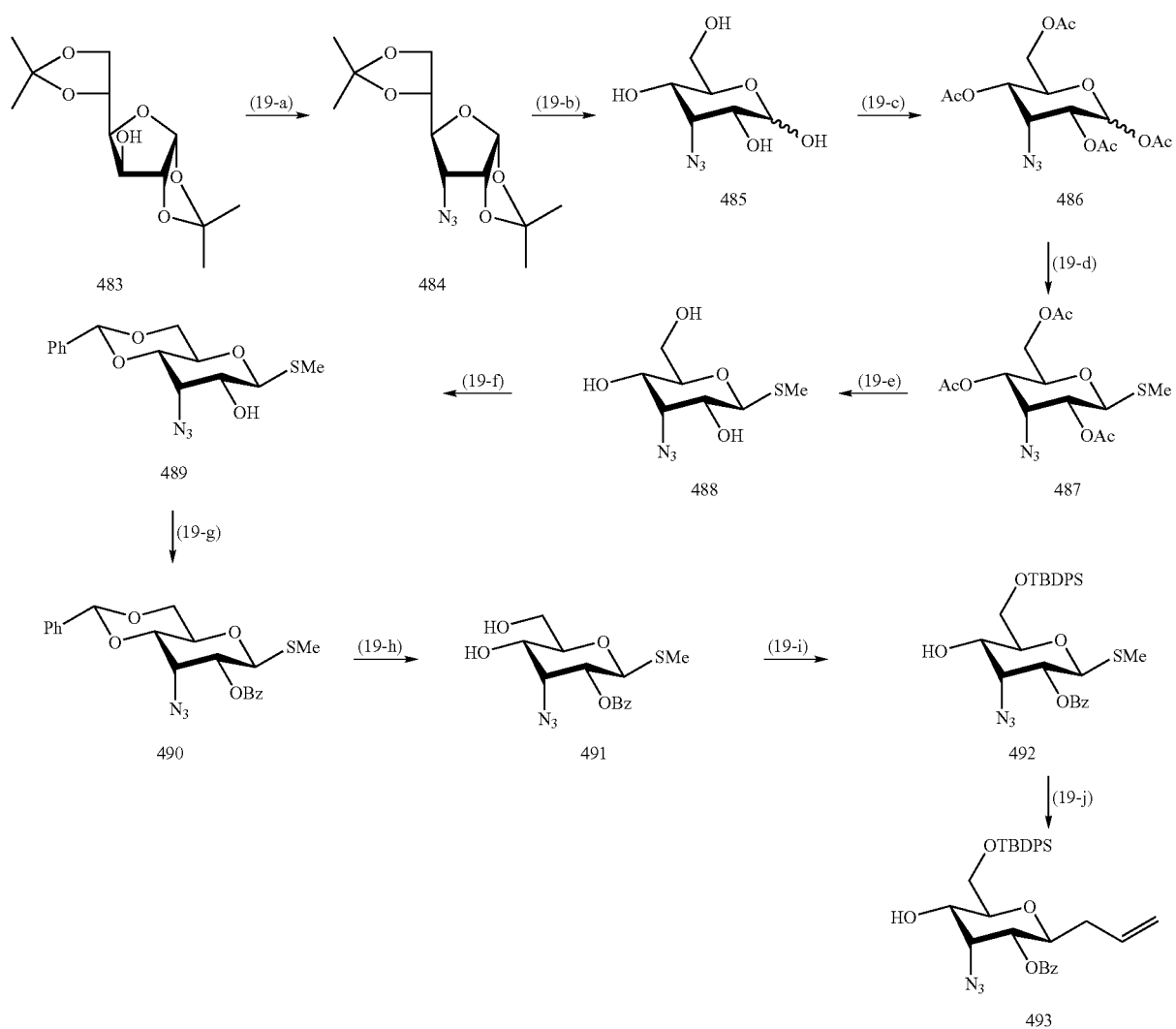

Conditions: (i) Tf$_2$O, pyridine, DCM; (b) NaN$_3$, DMF; (ii) acetone, H$^+$; (iii) Ac$_2$O, pyridine; (iv) hexamethyldisilazane, I$_2$, CH$_3$—S—S—CH$_3$; (v) NaOMe/MeOH; (vi) TsOH, α,α-dimethoxytoluene, MeCN; (vii) benzoylchloride, 1,2-DCE, pyridine, DMAP; (viii) TsOH, MeOH, H$_2$O, MeCN; (ix) TBDPS—Cl, imidazole, 1,2-DCE; (x) TMS-allyl, TMS—OTf, DCM.
EXAMPLE 20
Synthesis of a Range of C-Glycosides
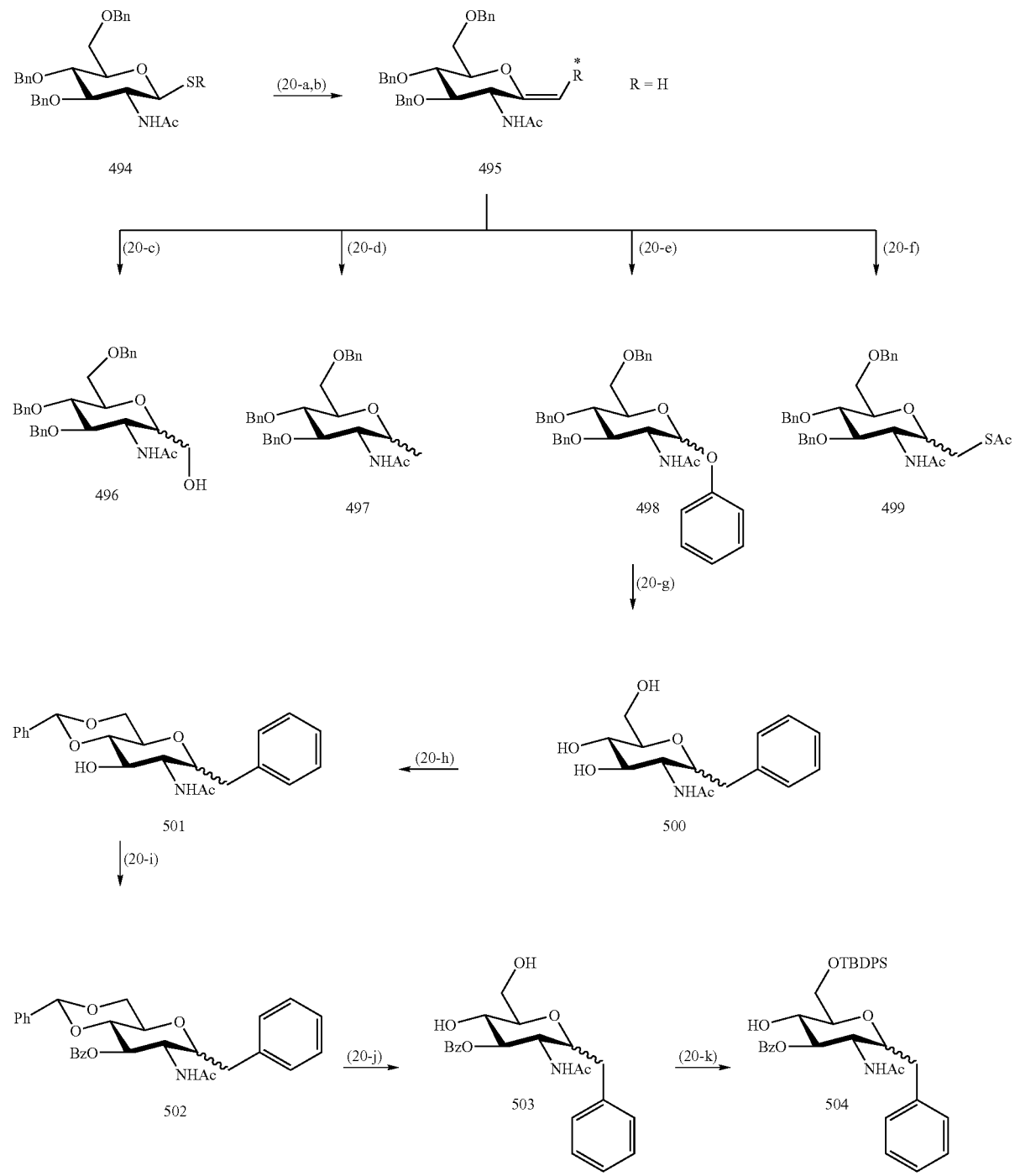

*Ramburg-Backlund rearrangement of phthalimido thioglycosides I to give an exo methylene compound II. The products can them be converted to a variety of C-glycosides which can be further elaborated to building blocks as exemplified by 28. The reaction pathway can furnish C-glycosides with a large number of alkyl or aromatic side-chains at the anomeric position. Conditions: (i) Oxone, (ii) KOH, $CCl_4$, (iii) $BH_3$, HOOH, $H_2$/Pd; (iv) $H_2$Pd; (v) ArX, Pd(0), $H_2$/Pd; (vi) AcSH, AIBN, $H_2$/Pd; (vii) (a) KOH, (b) $TfN_3$, RT, $CH_2Cl_2$, MeOH, $H_2$O/cat. $CUSO_4$, 90%; (viii) α,α-dimethoxytoluene, TsOH, MeCN/MeOH; (ix) BzCl, pyridine, (x) MeOH/MeCN/$H_2$O, TsOH; (xi) TBDPS—Cl, pyridine.

EXAMPLE 21

Synthesis of an Ribofuranosyl Azide Building Block bonate. The combined organic extracts were dried ($MgSO_4$) and the solvent was removed in vacuo to give a colourless oil, 100%.

21-b. 1-Azido ribose 507

The compound was synthesised according to the procedure described in General Method 1 (used directly in the following step).

21-c. 1-Azido-2,3-isopropylidene ribose 508

A solution of 1-azido ribose 507 (0.2 mol) in dry acetone (120 ml) and 2,2-dimethoxypropane (488 mmol) at room temperature and under nitrogen was treated with conc. sulfuric acid (16.9 mmol). The resulting solution was stirred at room temperature for 30 min. The reaction was quenched with pyridine and the solvent was removed in vacuo. The

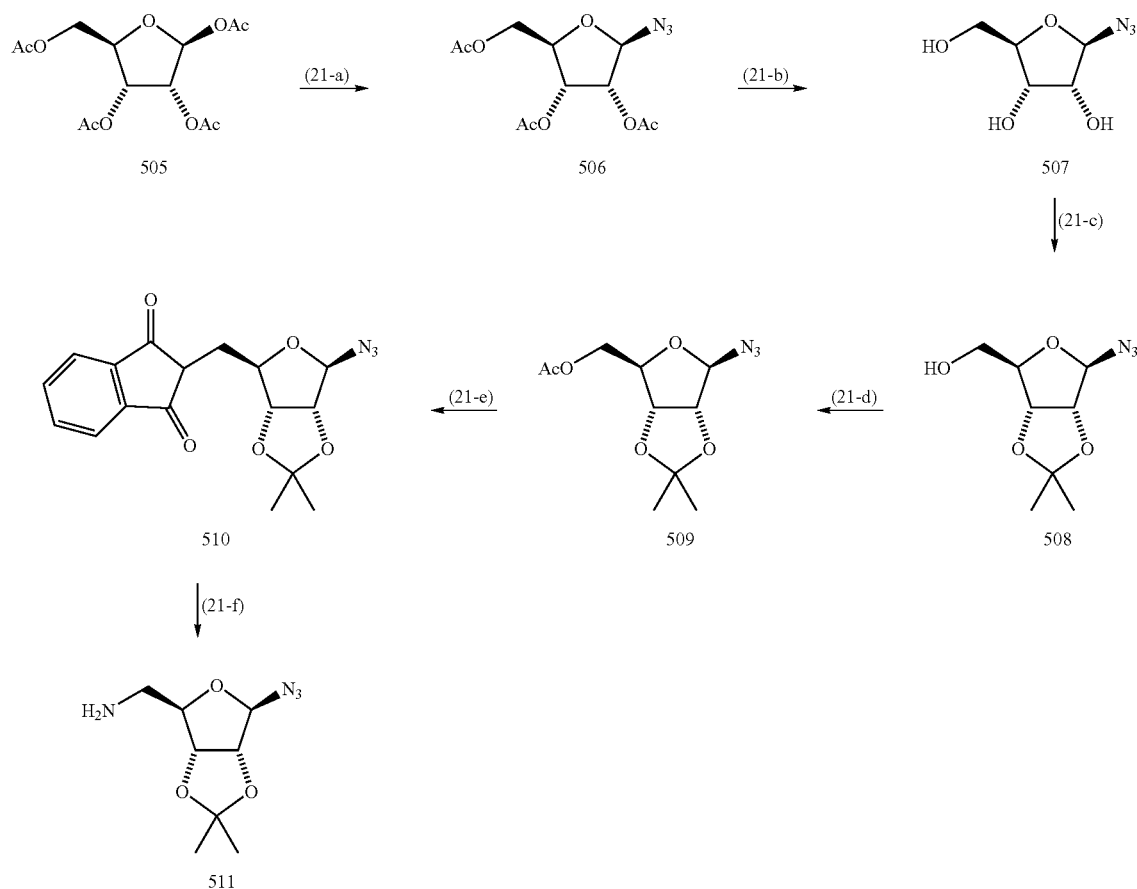

21-a. 1-Azido-2,3,5-triacetyl ribose 506

To a solution of 1,2,3,5-tetraacetyl ribose 505 (0.189 mol) in dry DCM (480 ml) at room temperature was added trimethylsilyl azide (0.211 mol) followed by a solution of anhydrous $SnCl_4$ (9.40 mmol) in dry DCM (60 ml). The resulting colourless solution was stirred at room temperature overnight. The solution was washed with saturated sodium bicarresidue was dissolved in DCM (500 ml), washed with 10% citric acid and saturated sodium bicarbonate, dried ($MgSO_4$) and the solvent was removed in vacuo to give a yellow oil which was purified by a squat column on silica gel (20-40% EtOAc/petrol) to give a yellow oil 508, 69 % from tetraacetate 505. $\delta_H$ (400 MHz: $CDCl_3$) 1.32 (s, 3H, $CH_3$), 1.50 (s, 3H, $CH_3$), 2.31 (dd, J 8.0, 5.2 Hz, 1H, OH), 3.67 (ddd, J 12.4, 7.6, 4.8 Hz, 1H, H5a), 3.77 (ddd, J 12.4, 6.2, 4.0 Hz, 1H, H5b), 4.41 (dd, J 5.2, 4.8 Hz, 1H, H4), 4.52 (d, J 6.0 Hz, 1H, H3), 4.77 (d, J 6.0 Hz, 1H, H2), 5.54 (s, 1H, H1).

21-d. 1-Azido-2,3-isopropylidene-5'-mesylate ribose 509

Methanesulfonyl chloride (18.1 mmol) was added over one min. to a suspension of the 2,3-isopropylidene ribose 508 (16.5 mmol) in dry pyridine (11 ml) at 0° C. and under $N_2$. The resulting suspension was stirred at 0° C. for 2.5 h, then quenched with water (20 ml) and extracted with ethyl acetate (2×20 ml). The combined organic extracts were washed with 10% citric acid and saturated $NaHCO_3$, dried ($MgSO_4$), and the solvent was removed in vacuo to give a pale yellow oil which was purified by a squat column on silica gel (20-40% EtOAc/petrol) to give a white solid, 88%. LCMS: >90% by ELSD, $(M-N_3)^+$ 251. $\delta_H$ (400 MHz: $CDCl_3$) 1.31 (s, 3H, $CH_3$), 1.49 (s, 3H, $CH_3$), 3.09 (s, 3H, $SO_2CH_3$), 4.28 (dd, J 10.6, 6.8 Hz, 1H, $H5_a$), 4.30 (dd, J 10.6, 6.0 Hz, 1H, $H5_b$), 4.50 (td, J 6.1, 1.2 Hz, 2H, H3, H4), 4.72 (dd, J 6.0, 1.3 Hz, 1H, H2), 5.56 (s, 1H, H1).

21-e. 1-Azido-2,3-isopropylidene-5'-phthalimido-ribose 510

A suspension of sugar derivative 509 (14.3 mmol), potassium phthalimide (18.8 mmol) and sodium iodide (2.86 mmol) in DMF (105 ml) was heated at 100° C. for 30 min., then cooled to room temperature and diluted with water (500 ml) and cooled in an ice-water bath. The resulting product were collected by vacuum filtration, washed with water and dried over $P_2O_5$ in a dessicator overnight as white crystals, 51%. LCMS: >95% by ELSD, $(2M+H)^+$ 711. $\delta_H$ (400 MHz: $CDCl_3$) 1.29 (s, 3H, $CH_3$), 1.45 (s, 3H, $CH_3$), 3.91 (dd, J 13.9, 8.4 Hz, 1H, $H5_a$), 3.95 (dd, J 13.9, 6.5 Hz, 1H, $H5_b$), 4.57 (t, J 6.4 Hz, 2H, H3, H4), 4.78 (d, J 5.8 Hz, 1H, H2), 5.57 (s, 1H, H1), 7.73 (d, J 3.2 Hz, 1H, ArH), 7.74 (d, J 3.2 Hz, 1H, ArH), 7.87 (d, J 3.2 Hz, 1H, ArH), 7.88 (d, J 3.2 Hz, 1H, ArH).

21-f. 1-Azido-2,3-isopropylidene-5'-amino-ribose 511

A suspension of sugar derivative 510 (8.13 mmol) in methanol (21 ml) was treated with hydrazine hydrate (12.0 mmol) to give a pale yellow solution which was heated at reflux for 2 h. The methanol was removed in vacuo from the resulting suspension and the residue was dissolved in water (40 ml) and acidified (to pH 1) with conc. HCl. The resulting precipitate was removed by vacuum filtration and washed with water. To the filtrate was added solid sodium hydroxide (to pH 10) and the product was extracted with $CHCl_3$ and dried ($MgSO_4$). The solvent was removed in vacuo to give a yellow oil, 93%. LCMS: $(M-N_3)^+$=172; $\delta$ (400 MHz: $CDCl_3$) 1.32 (bs, 5H, $CH_3$, $NH_2$), 1.50 (s, 3H, $CH_3$), 2.84 (dd, J 13.1, 6.0 Hz, 1H, $H5_a$), 2.90 (dd, J 13.0, 8.1 Hz, 1H, $H5_b$), 4.24 (t, J 7.0 Hz, 1H, H4), 4.48 (d, J 5.8 Hz, 1H, H3), 4.61 (d, J 4.8 Hz, 1H, H2), 5.53 (s, 1H, H1).

REFERENCES

1. K. C. Nicolaou; J. M. Salvino, K. Raynor; S. Pietranico; T. Reisine; R. M. Freidinger, R. Hirschmann, *Pept.: Chem., Struct Biol., Proc. Am. Pept. Symp.*, 11th, 1990
2. (a) H. Kunz, T. Wundberg, C. Kallus, T. Opatz, S. Henke, W. Schmidt, *Angew. Chem. Int. Ed.*, 1998, 37, No. 18, (b) K. Kallus, T. Wundberg, W. Schmidt, S. Henke, H. Kunz, *Tet. Lett.*, 40, 1999, 7783-7786, (c) U. Hünger, T. Maidhof, O. Knöll, H. Kunz, *Poster Presentation*, 20th *International Carbohydrate Symposium*, Hamburg-Germany, (d) T. Opatz, C. Kallus, T. Wundberg, W. Schmidt, S. Henke, H. Kunz, *Poster Presentation*, 20th *International Carbohydrate Symposium*, Hamburg-Germany.
3. R. Hirschmann, K. C. Nicolaou, S. Pietramico, J. Salvino, E. M. Lealy, W. C. Shakepeare, P. S. Spengler, P. Hamley, A. B. Smith, T. Reisine, K. Raynor, C. Donaldson, W. Vale, L. Maechler, R. M. Freidinger, C. D. Strader, *J. Am. Chem. Soc.*, 1993, 115, 12550

The invention claimed is:

1. A compound of formula I

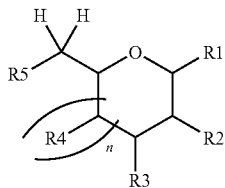

formula I

Being a modified monosaccharide, wherein, n is 0 or 1;

R1 is selected from the group consisting of hydrogen or —N(Z)Y wherein;

Y is selected from the following, where G denotes the point of connection to the nitrogen atom in N(Z)Y;

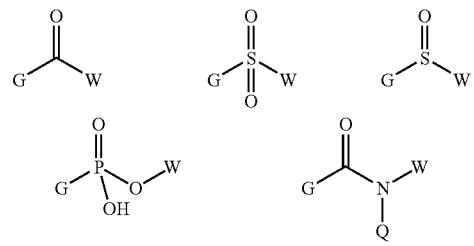

Z is selected from hydrogen or W;

Q is selected from hydrogen or W;

the groups W are independently selected from the group consisting of:

a) a substituted or unsubstituted alkyl moiety of 1 to 20 atoms;

b) a substituted or unsubstituted alkenyl, or alkynyl moiety of 2 to 20 atoms;

c) a substituted or unsubstituted heteroalkyl moiety of 2 to 20 atoms in which the hetero atoms are selected from the group consisting of N, O and S;

d) a substituted or unsubstituted monocyclic or bicyclic aryl moiety of 6 to 12 carbon atoms;

e) a substituted or unsubstituted monocyclic or bicyclic heteroaryl moiety of 5 to 20 atoms, containing 1 to 4 hetero atoms selected from the group N, O and S;

f) an arylalkyl moiety of 6 to 20 atoms comprising at least 1 substituted or unsubstituted monocyclic or bicyclic aryl moiety and a substituted or unsubstituted alkyl moiety;

g) an heteroarylalkyl moiety of 5 to 20 atoms comprising a substituted or unsubstituted monocyclic or bicyclic heteroaryl moiety containing 1 to 4 hetero atoms selected from the group N, O and S, and a substituted or unsubstituted alkyl moiety;

the groups R2, R3, R4 and R5 are independently selected from —OH, —OW and —N(Z)Y wherein at least one of the groups R2, R3, and R4 is —N(Z)Y, and at least one of the groups R2, R3, R4 and R5 is —OW and at least one of the groups R2, R3, R4 and R5 is —OH, Z and Y optionally combine with N to form a ring, such that where more than one of the groups R2, R3, R4 and R5 is OW, each instance of OW is different.

2. The compound of claim 1, wherein the groups Z and Y are combined to form a monocyclic or bicyclic ring structure of 4 to 10 atoms.

3. The compound of claim 2, wherein the ring structure is further substituted with W groups.

4. The compound of claim 1 wherein W is substituted with a moiety selected from the group consisting of OH, NO, $NO_2$, $NH_2$, $N_3$, halogen, $CF_3$, $CHF_2$, $CH_2F$, nitrile, alkoxy, aryloxy, amidine, guanidiniums, carboxylic acid, carboxylic acid ester, carboxylic acid amide, aryl, cycloalkyl, heteroalkyl, heteroaryl, aminoalkyl, aminodialkyl, aminotrialkyl, aminoacyl, carbonyl, substituted or unsubstituted imine, sulfate, sulfonamide, phosphate, phosphoramide, hydrazide, hydroxamate, hydroxamic acid; wherein the terms alkyl, aryl, heteroalkyl and heteroaryl are as defined in claim 1.

5. The compound of claim 1, wherein Z is hydrogen.

6. The compound of claim 1 wherein at least three of the groups R2, R3, R4 and R5 are selected from —OW or —N(Z)Y;

7. The compound of claim 1 wherein R1 is hydrogen.

8. The compound of claim 7 wherein independently at least two of R2, R3, R4, or R5 are —OW.

9. The compound of claim 7 wherein at least two of R2, R3, R4, or R5 is —N(Z)Y.

10. The compound of claim 1 wherein R1 is —N(Z)Y.

11. The compound of claim 10 wherein at least one of R2, R3, R4, or R5 is —N(Z)Y.

12. The compound of claim 10 wherein at least two of R2, R3, R4, or R5 is —N(Z)Y.

13. The compound of claim 10 wherein at least two of R2, R3, R4, or R5 are —OW.

14. A method of synthesis of compounds of claim 7, wherein n is 1, comprising the step of reducing a synthetic intermediate of formula III, in which V is bromine or chlorine, R5, R4, R3, and R2 are selected from the group consisting of OH, O-acyl, $N_3$, NHDde, NHDTPM, NHZ, NHBOC, phthalimide, OW, N(Z)Y and an O-protecting group, Y is selected from the following, where G denotes the point of connection to the nitrogen atom in N(Z)Y;

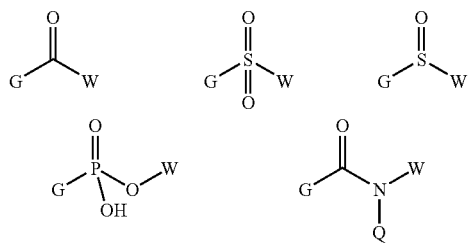

Z is selected from hydrogen or W;

Q is selected from hydrogen or W;

the groups W are independently selected from the group consisting of:

a) a substituted or unsubstituted alkyl moiety of 1 to 20 atoms;

b) a substituted or unsubstituted alkenyl, or alkynyl moiety of 2 to 20 atoms;

c) a substituted or unsubstituted heteroalkyl moiety of 2 to 20 atoms in which the hetero atoms are selected from the group consisting of N, O and S;

d) a substituted or unsubstituted monocyclic or bicyclic aryl moiety of 6 to 12 carbon atoms;

e) a substituted or unsubstituted monocyclic or bicyclic heteroaryl moiety of 5 to 20 atoms, containing 1 to 4 hetero atoms selected from the group N, O and S;

f) an arylalkyl moiety of 6 to 20 atoms comprising at least 1 substituted or unsubstituted monocyclic or bicyclic aryl moiety and a substituted or unsubstituted alkyl moiety;

g) an heteroarylalkyl moiety of 5 to 20 atoms comprising a substituted or unsubstituted monocyclic or bicyclic heteroaryl moiety containing 1 to 4 hetero atoms selected from the group N, O and S, and a substituted or unsubstituted alkyl moiety;

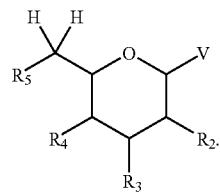

general formula III

15. The method of claim 14, wherein the O-protecting groups comprise a benzylidene acetal which protects two adjacent oxygens.

16. A method of synthesis of compounds according to claim 10, in which n is 1, comprising the step of reacting a compound of formula III with an azide nucleophile, to form an anomeric azide and reduction of the anomeric azide to form an anomeric amine and reaction of the anomeric amine with an electrophile.

17. A method of combinatorial synthesis of compounds of claim 1, wherein n is 1, comprising the steps of:

(a) immobilizing a compound of formula IV onto a support, through a free hydroxyl or amino function;

(b) selectively removing a protecting group from a protected hydroxyl functionality to provide a free hydroxyl function; and (c) alkylating said free hydroxyl function;

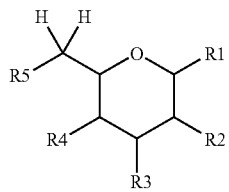

general formula IV wherein

R1 is selected from the group consisting of hydrogen and —N(Z)Y wherein;

When R1 is —N(Z)Y, then:

Y is selected from the following, where G denotes the point of connection to the nitrogen atom in N(Z)Y;

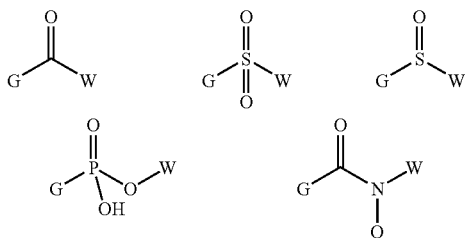

Z is selected from hydrogen or W;
Q is selected from hydrogen or W;
the groups W are independently selected from the group consisting of:
a) a substituted or unsubstituted alkyl moiety of 1 to 20 atoms;
b) a substituted or unsubstituted alkenyl, or alkynyl moiety of 2 to 20 atoms;
c) a substituted or unsubstituted heteroalkyl moiety of 2 to 20 atoms in which the hetero atoms are selected from the group consisting of N, O and S;
d) a substituted or unsubstituted monocyclic or bicyclic aryl moiety of 6 to 12 carbon atoms;
e) a substituted or unsubstituted monocyclic or bicyclic heteroaryl moiety of 5 to 20 atoms, containing 1 to 4 hetero atoms selected from the group N, O and S;
f) an arylalkyl moiety of 6 to 20 atoms comprising at least 1 substituted or unsubstituted monocyclic or bicyclic aryl moiety and a substituted or unsubstituted alkyl moiety;
g) an heteroarylalkyl moiety of 5 to 20 atoms comprising a substituted or unsubstituted monocyclic or bicyclic heteroaryl moiety containing 1 to 4 hetero atoms selected from the group N, O and S, and a substituted or unsubstituted alkyl moiety;
R5, R4, R3, and R2 are selected from the group consisting of OH, O-acyl, $N_3$, NHDde, NHDTPM, NHZ, NHBOC, phthalimide, OW, N(Z)Y and an O-protecting group.

18. The method of claim 17 wherein the support is selected from the group consisting of tentagel, wang resin, MBHA resin, aminomethylpolystyrene, rink amide resin DOX-mpeg, and polyethylene glycol.

19. A method of synthesis of compounds according to claim 9, in which n is 0, comprising the step of reacting a compound of formula V in the presence of a lewis acid with an azide source to form an anomeric azide, reduction of the anomeric azide to form an anomeric amine and reaction of the anomeric amine with an electrophile;

general formula V

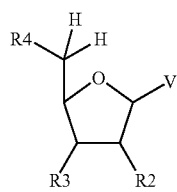

in which V is —OAcyl,
R4, R3, and R2 are selected from the group consisting of OH, O-acyl, $N_3$, NHDde, NHDTPM, NHZ, NHBOC, phthalimide, OW, N(Z)Y and O-protecting group, the groups W are independently selected from the group consisting of:
a) a substituted or unsubstituted alkyl moiety of 1 to 20 atoms;
b) a substituted or unsubstituted alkenyl, or alkynyl moiety of 2 to 20 atoms;
c) a substituted or unsubstituted heteroalkyl moiety of 2 to 20 atoms in which the hetero atoms are selected from the group consisting of N, O and S;
d) a substituted or unsubstituted monocyclic or bicyclic aryl moiety of 6 to 12 carbon atoms;
e) a substituted or unsubstituted monocyclic or bicyclic heteroaryl moiety of 5 to 20 atoms, containing 1 to 4 hetero atoms selected from the group N, O and S;
f) an arylalkyl moiety of 6 to 20 atoms comprising at least 1 substituted or unsubstituted monocyclic or bicyclic aryl moiety and a substituted or unsubstituted alkyl moiety;
g) an heteroarylalkyl moiety of 5 to 20 atoms comprising a substituted or unsubstituted monocyclic or bicyclic heteroaryl moiety containing 1 to 4 hetero atoms selected from the group N, O and S, and a substituted or unsubstituted alkyl moiety;
Y is selected from the following, where G denotes the point of connection to the nitrogen atom in N(Z)Y;

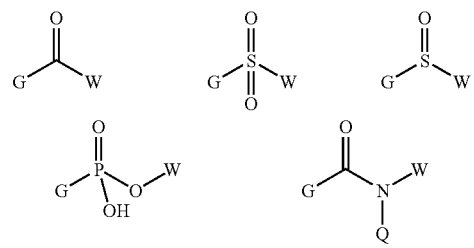

Z is selected from hydrogen or W; and
Q is selected from hydrogen or W.

20. A method of combinatorial synthesis of compounds of claim 1, wherein n is 0, comprising the steps of
(a) immobilizing a compound of formula VI onto a support, through a free hydroxyl or amino function;
(b) selectively removing a protecting group from a protected hydroxyl functionality to provide a free hydroxyl function; and
(c) alkylating said free hydroxyl function;

general formula VI

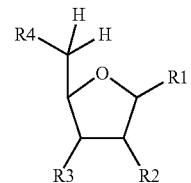

Wherein R1 is selected from the group consisting of hydrogen and —N(Z)Y
wherein;
When R1 is —N(Z)Y, then:
Y is selected from the following, where G denotes the point of connection to the nitrogen atom in N(Z)Y;

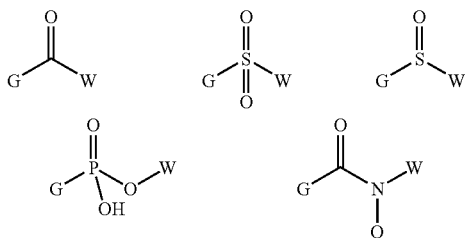

Z is selected from hydrogen or W;
Q is selected from hydrogen or W;
the groups W are independently selected from the group consisting of:
a) a substituted or unsubstituted alkyl moiety of 1 to 20 atoms;
b) a substituted or unsubstituted alkenyl, or alkynyl moiety of 2 to 20 atoms;
c) a substituted or unsubstituted heteroalkyl moiety of 2 to 20 atoms in which the hetero atoms are selected from the group consisting of N, O and S;
d) a substituted or unsubstituted monocyclic or bicyclic aryl moiety of 6 to 12 carbon atoms;
e) a substituted or unsubstituted monocyclic or bicyclic heteroaryl moiety of 5 to 20 atoms, containing 1 to 4 hetero atoms selected from the group N, O and S;
f) an arylalkyl moiety of 6 to 20 atoms comprising at least 1 substituted or unsubstituted monocyclic or bicyclic aryl moiety and a substituted or unsubstituted alkyl moiety;
g) an heteroarylalkyl moiety of 5 to 20 atoms comprising a substituted or unsubstituted monocyclic or bicyclic heteroaryl moiety containing 1 to 4 hetero atoms selected from the group N, O and S, and a substituted or unsubstituted alkyl moiety; and
R4, R3, and R2 are selected from the group consisting of OH, O-acyl, $N_3$, NHDde, NHDTPM, NHZ, NHBOC, phthalimide, OX2, N(T)Y and O-protecting group.

21. The method of claim 20, wherein the support is selected from the group consisting of tentagel, wang resin, MBHA resin, aminomethylpolystyrene, rink amide resin DOX-mpeg, and polyethylene glycol.

22. A method of solution phase combinatorial synthesis of compounds of formula I
Being a modified monosaccharide, wherein,
n is 0 or 1;
R1 is selected from the group consisting of hydrogen or —N(Z)Y wherein;
Y is selected from the following, where G denotes the point of connection to the nitrogen atom in N(Z)Y;
Z is selected from hydrogen or W;
Q is selected from hydrogen or W; the groups W are independently selected from the group consisting of:
a) a substituted or unsubstituted alkyl moiety of 1 to 20 atoms;
b) a substituted or unsubstituted alkenyl, or alkynyl moiety of 2 to 20 atoms;
c) a substituted or unsubstituted heteroalkyl moiety of 2 to 20 atoms in which the hetero atoms are selected from the group consisting of N, O and S;
d) a substituted or unsubstituted monocyclic or bicyclic aryl moiety of 6 to 12 carbon atoms;
e) a substituted or unsubstituted monocyclic or bicyclic heteroaryl moiety of 5 to 20 atoms, containing 1 to 4 hetero atoms selected from the group N, O and S;
f) an arylalkyl moiety of 6 to 20 atoms comprising at least 1 substituted or unsubstituted monocyclic or bicyclic aryl moiety and a substituted or unsubstituted alkyl moiety;
g) an heteroarylalkyl moiety of 5 to 20 atoms comprising a substituted or unsubstituted monocyclic or bicyclic heteroaryl moiety containing 1 to 4 hetero atoms selected from the group N, O and S, and a substituted or unsubstituted alkyl moiety;
the groups R2, R3, R4 and R5 are independently selected from —OH, —OW and —N(Z)Y wherein at least one of the groups R2, R3, and R4 is —N(Z)Y, and at least one of the groups R2, R3, R4 and R5 is —OW and at least one of the groups R2, R3, R4 and R5 is —OH,
Z and Y optionally combine with N to form a ring, such that where more than one of the groups R2, R3, R4 and R5 is OW, each instance of OW is different, comprising the step of alkylating a free hydroxyl on a compound of formula IV
formula IV
wherein
R1 is selected from the group consisting of hydrogen and —N(Z)Y wherein;
When R1 is —N(Z)Y, then:
Y is selected from the following, where G denotes the point of connection to the nitrogen atom in N(Z)Y;
Z is selected from hydrogen or W;
Q is selected from hydrogen or W;
the groups W are independently selected from the group consisting of:
a) a substituted or unsubstituted alkyl moiety of 1 to 20 atoms;
b) a substituted or unsubstituted alkenyl, or alkynyl moiety of 2 to 20 atoms;
c) a substituted or unsubstituted heteroalkyl moiety of 2 to 20 atoms in which the hetero atoms are selected from the group consisting of N, O and S;
d) a substituted or unsubstituted monocyclic or bicyclic aryl moiety of 6 to 12 carbon atoms;
e) a substituted or unsubstituted monocyclic or bicyclic heteroaryl moiety of 5 to 20 atoms, containing 1 to 4 hetero atoms selected from the group N, O and S;
f) an arylalkyl moiety of 6 to 20 atoms comprising at least 1 substituted or unsubstituted monocyclic or bicyclic aryl moiety and a substituted or unsubstituted alkyl moiety;
g) an heteroarylalkyl moiety of 5 to 20 atoms comprising a substituted or unsubstituted monocyclic or bicyclic heteroaryl moiety containing 1 to 4 hetero atoms selected from the group N, O and S, and a substituted or unsubstituted alkyl moiety;
R5, R4, R3, and R2 are selected from the group consisting of OH, O-acyl, N3, NHDde, NHDTPM, NHZ, NHBOC, phthalimide, N(Z)Y and an O-protecting group.
or formula VI
Wherein R1 is selected from the group consisting of hydrogen and —N(Z)Y wherein;
When R1 is —N(Z)Y, then:
Y is selected from the following, where G denotes the point of connection to the nitrogen atom in N(Z)Y;

Wherein R1 is selected from the group consisting of hydrogen and —N(Z)Y wherein;

When R1 is—N(Z)Y, then:

Y is selected from the following, where G denotes the point of connection to the nitrogen atom in N(Z)Y;

Z is selected from hydrogen or W; and

Q is selected from hydrogen or W.

the groups W are independently selected from the group consisting of:
a) a substituted or unsubstituted alkyl moiety of 1 to 20 atoms;
b) a substituted or unsubstituted alkenyl, or alkynyl moiety of 2 to 20 atoms;
c) a substituted or unsubstituted heteroalkyl moiety of 2 to 20 atoms in which the hetero atoms are selected from the group consisting of N, O and S;
d) a substituted or unsubstituted monocyclic or bicyclic aryl moiety of 6 to 12 carbon atoms;
e) a substituted or unsubstituted monocyclic or bicyclic heteroaryl moiety of 5 to 20 atoms, containing 1 to 4 hetero atoms selected from the group N, O and S;
f) an arylalkyl moiety of 6 to 20 atoms comprising at least 1 substituted or unsubstituted monocyclic or bicyclic aryl moiety and a substituted or unsubstituted alkyl moiety;
g) an heteroarylalkyl moiety of 5 to 20 atoms comprising a substituted or unsubstituted monocyclic or bicyclic heteroaryl moiety containing 1 to 4 hetero atoms selected from the group N, O and S, and a substituted or unsubstituted alkyl moiety; and R4, R3, and R2 are selected from the group consisting of OH, O-acyl, N3, NHDde, NHDTPM, NHZ, NHBOC, phthalimide, OX2, N(T)Y and O-protecting group.

23. A compound of formula 2 formula 2

Wherein, n is 0;

R1 is selected from the group consisting of hydrogen or —N(Z)Y wherein;

Y is selected from the following, where G denotes the point of connection to the nitrogen atom in N(Z)Y;

Z is selected from hydrogen or W;

Q is selected from hydrogen or W;

the groups W are independently selected from the group consisting of:
a) a substituted or unsubstituted alkyl moiety of 1 to 20 atoms;
b) a substituted or unsubstituted alkenyl, or alkynyl moiety of 2 to 20 atoms;
c) a substituted or unsubstituted heteroalkyl moiety of 2 to 20 atoms in which the hetero atoms are selected from the group consisting of N, O and S;
d) a substituted or unsubstituted monocyclic or bicyclic aryl moiety of 6 to 12 carbon atoms;
e) a substituted or unsubstituted monocyclic or bicyclic heteroaryl moiety of 5 to 20 atoms, containing 1 to 4 hetero atoms selected from the group N, O and S;
f) an arylalkyl moiety of 6 to 20 atoms comprising at least 1 substituted or unsubstituted monocyclic or bicyclic aryl moiety and a substituted or unsubstituted alkyl moiety;
g) an heteroarylalkyl moiety of 5 to 20 atoms comprising a substituted or unsubstituted monocyclic or bicyclic heteroaryl moiety containing 1 to 4 hetero atoms selected from the group N, O and S, and a substituted or unsubstituted alkyl moiety;

When R1 is —N(Z)Y, then at least one of the groups R2, R3, R4 and R5 is —N(Z)Y, and the others of the groups R2, R3, R4 and R5 are independently selected from hydrogen, —OH, —OW, —N(Z)Y, When R1 is H, then at least one of the groups R2, R3, R4 and R5 is —OW and at least one of the groups R2, R3, R4 or R5 is —N(Z)Y, and the others of the groups R2, R3, R4 and R5 are independently selected from hydrogen, —OH, —OW, —N(Z)Y, Z and Y optionally combine with N to form a ring, With the provisos that:

W may not be another carbohydrate ring, a cyclitol ring or contain another carbohydrate ring, and all of the W substituents may not be the same.

24. A compound of formula 3 formula 3

Wherein, n is 1;

R1 is selected from the group consisting of hydrogen or —N(Z)Y wherein;

Y is selected from the following, where G denotes the point of connection to the nitrogen atom in N(Z)Y;

-continued

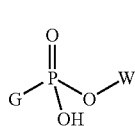 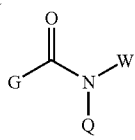

Z is selected from hydrogen or W;
Q is selected from hydrogen or W;
the groups W are independently selected from the group consisting of:
a) a substituted or unsubstituted alkyl moiety of 1 to 20 atoms;
b) a substituted or unsubstituted alkenyl, or alkynyl moiety of 2 to 20 atoms;
c) a substituted or unsubstituted heteroalkyl moiety of 2 to 20 atoms in which the hetero atoms are selected from the group consisting of N, O and S;
d) a substituted or unsubstituted monocyclic or bicyclic aryl moiety of 6 to 12 carbon atoms;
e) a substituted or unsubstituted monocyclic or bicyclic heteroaryl moiety of 5 to 20 atoms, containing 1 to 4 hetero atoms selected from the group N, O and S;
f) an arylalkyl moiety of 6 to 20 atoms comprising at least 1 substituted or unsubstituted monocyclic or bicyclic aryl moiety and a substituted or unsubstituted alkyl moiety;
g) an heteroarylalkyl moiety of 5 to 20 atoms comprising a substituted or unsubstituted monocyclic or bicyclic heteroaryl moiety containing 1 to 4 hetero atoms selected from the group N, O and S, and a substituted or unsubstituted alkyl moiety;

When R1 is —N(Z)Y, then at least one of the groups R2, R3, R4 and R5 is —N(Z)Y, and the others of the groups R2, R3, R4 and R5 are independently selected from hydrogen, —OH, —OW, —N(Z)Y, When R1 is H, then at least one of the groups R2, R3, R4 and R5 is —OW and at least one of the groups R2, R3, R4 or R5 is —N(Z)Y, and the others of the groups R2, R3, R4 and R5 are independently selected from hydrogen, —OH, —OW, —N(Z)Y, Z and Y optionally combine with N to form a ring,
With the provisos that:
a. W may not be another carbohydrate ring, a cyclitol ring or contain another carbohydrate ring; and
b. all of the W substituents may not be the same.

* * * * *